US008241846B1

(12) United States Patent
Charron et al.

(10) Patent No.: US 8,241,846 B1
(45) Date of Patent: Aug. 14, 2012

(54) HEDGEHOG PATHWAY MODULATION AND USES THEREOF FOR TREATING, PREVENTING AND/OR DIAGNOSING CANCER

(75) Inventors: Frédéric Charron, Montréal (CA); Cynthia Hawkins, Toronto (CA); Martin Lévesque, Québec (CA)

(73) Assignees: Institut de Recherches Cliniques de Montreal, Montreal (CA); The Hospital for Sick Children, Toronto (CA)

( * ) Notice: Subject to any disclaimer, the term of this patent is extended or adjusted under 35 U.S.C. 154(b) by 0 days.

(21) Appl. No.: 12/555,077

(22) Filed: Sep. 8, 2009

Related U.S. Application Data

(60) Provisional application No. 61/095,155, filed on Sep. 8, 2008.

(51) Int. Cl.
*C12Q 1/68* (2006.01)
(52) U.S. Cl. .............................. 435/6; 435/325; 435/375
(58) Field of Classification Search .................. None
See application file for complete search history.

(56) References Cited

U.S. PATENT DOCUMENTS

| | | | |
|---|---|---|---|
| 4,736,866 | A | 4/1988 | Leder et al. |
| 5,087,571 | A | 2/1992 | Leder et al. |
| 5,175,383 | A | 12/1992 | Leder et al. |
| 5,175,384 | A | 12/1992 | Krimpenfort et al. |
| 5,175,385 | A | 12/1992 | Wagner et al. |
| 6,025,155 | A | 2/2000 | Hadlaczky et al. |
| 6,077,677 | A | 6/2000 | Hodgson et al. |
| 6,204,023 | B1 | 3/2001 | Robinson et al. |
| 7,625,759 | B2 * | 12/2009 | de Sauvage et al. ............ 436/86 |
| 2002/0160970 | A1 | 10/2002 | Hadlaczky et al. |
| 2003/0083293 | A1 | 5/2003 | Hadlaczky et al. |

OTHER PUBLICATIONS

Rubin et al. (Nature Reviews: Drug Discovery 2006).*
Berman et al. (Science 297: 1559-1561: 2002).*
Tenzen et al. (Developmental Cell 10: 647-656, 2006).*
Binz et al., "Engineered proteins as specific binding reagents", Current Opinion in Biotechnology (2005) 16: 459-469.
Ericson et al., "Two Critical Periods of Sonic Hedgehog Signaling Required for the Specification of Motor Neuron Identity", Cell (1996), 87: 661-673.
Friedel et al., "Gene targeting using a promoterless gene trap vector ("targeted trapping") is an efficient method to mutate a large fraction of genes", PNAS (2005), 102 (37): 13188-13193.
Goodrich et al., "Altered Neural Cell Fates and Medulloblastoma in Mouse patched Mutants", Science (1997) 277: 1109-1113.
Hormigo et al., "YKL-40 and Matrix Metalloproteinase-9 as Potential Serum Biomarkers for Patients with High-Grade Gliomas", Clin Cancer Res (2006) 12(19): 5698-5704.
Kohler et al., "Continuous cultures of fused cells secreting antibody of predefined specificity", Nature (1975) 256: 495-497.
Lash et al., "SAGEmap: A Public Gene Expression Resource", Genome Res. (2000) 10: 1051-1060.
McMahon et al., "Developmental Roles and Clinical Significance of Hedgehog Signaling", Developmental Biology (2000) 53: 1-114.
Mosmann Tim, "Rapid Colorimetric Assay for Cellular Growth and Survival: Application to Proliferation and Cytotoxicity Assays", Journal of Immunological Methods (1983) 65:55-63.
Okada et al., "Boc is a receptor for sonic hedgehog in the guidance of commissural axons", Nature (2006) 444: 369-373.
Oliver et al., "Loss of patched and disruption of granule cell development in a pre-neoplastic stage of medulloblastoma", Development and disease (2005) 132: 2425-2439.
Ray et al., "A Clinicobiological Model Predicting Survival in Medulloblastoma", Clinical Cancer Research (2004) 10: 7613-7620.
Rossi et al., "Medulloblastoma: From Molecular Pathology to Therapy", Clin Cancer Res (2008) 14(4): 971-976.
Tanwar et al., "Gene Expression Microarray Analysis Reveals YKL-40 to Be a Potential Serum Marker for Malignant Character in Human Glioma", Cancer Res (2002) 62: 4364-4368.
Theunissen et al., "Paracrine Hedgehog Signaling in Cancer", Cancer Res (2009) 69(15): 6007-6010.
Tian et al., "Hedgehog signaling is restricted to the stromal compartment during pancreatic carcinogenesis"., PNAS (2009) 106(11): 4254-4259.
Yao et al., "The Ihog Cell-Surface Proteins Bind Hedgehog and Mediate Pathway Activation", Cell (2006) 125: 343-357.
Yauch et al., "A paracrine requirement for hedgehog signalling in cancer", Nature (2008) 455: 406-411.
Kean, "Disrupting Hedgehog may reverse advanced cancer, if only temporarily", Science (2009) 325:1188.
Kool et al., "Integrated genomics identifies five medulloblastoma subtypes with distinct genetic profiles, pathway signatures and clinicopathological features", PLoS ONE (2008) 3(8): e3088 1-14.
Scales et al., "Mechanisms of Hedgehog pathway activation in cancer and implications for therapy", Trends in Pharmacological Sciences (Jun. 30, 2009), 30(6): 303-312, Epublished on May 13, 2009.

* cited by examiner

*Primary Examiner* — Kimberly Chong
(74) *Attorney, Agent, or Firm* — Coudreau Gage Dubuc; Julie Gauvreau

(57) ABSTRACT

Methods, uses, agents and compositions useful for the diagnosis, prevention and/or treatment of invasive diseases such as cancer based on the modulation of the expression and/or activity of brother of CDON (BOC) are disclosed.

23 Claims, 30 Drawing Sheets

| TMA | Total N | % |
|---|---|---|
| Boc positive | 38 | 52.1 |
| Boc negative | 35 | 47.9 |
| Total: | 73 | 100 |

| SAGE total | Total N | % |
|---|---|---|
| Boc positive | 6 | 31.6 |
| Boc negative | 13 | 68.4 |
| Total: | 19 | 100 |

| SAGE MB Shh | Total N | % |
|---|---|---|
| Boc positive | 4 | 80.0 |
| Boc negative | 1 | 20.0 |
| Total: | 5 | 100 |

| SAGE MB Wnt | Total N | % |
|---|---|---|
| Boc positive | 2 | 100.0 |
| Boc negative | 0 | 0.0 |
| Total: | 2 | 100 |

Nucleotide sequence of human BOC (SEQ ID NO: 1, RefSeq accession No.
NM_033254) - Coding sequence: residues 340-3684

```
   1 gtttctcata gttggcgtct tctaaaggaa aaacactaaa atgaggaact cagcggaccg
  61 ggagcgacgc agcttgaggg aagcatccct agctgttggc gcagagggc gaggctgaag
 121 ccgagtggcc cgaggtgtct gagggctgg ggcaaaggtg aaagagtttc agaacaagct
 181 tcctggaacc catgacccat gaagtcttgt cgacatttat accgtctgag ggtagcagct
 241 cgaaagtaga agaagtggag tgttgccagg gacggcagta tctctttgtg tgaccctggc
 301 ggcttatggg acgttggctt cagacctttg tgatacacca tgctgcgtgg gacgatgacg
 361 gcgtggagag gaatgaggcc tgaggtcaca ctggcttgcc tcctcctagc cacagcaggc
 421 tgctttgctg acttgaacga ggtccctcag gtcaccgtcc agcctgcgtc caccgtccag
 481 aagcccggag gcactgtgat cttgggctgc gtggtggaac ctccaaggat gaatgtaacc
 541 tggcgcctga atggaaagga gctgaatggc tcggatgatg ctctgggtgt cctcatcacc
 601 cacgggaccc tcgtcatcac tgcccttaac aaccacactg tgggacggta ccagtgtgtg
 661 gcccggatgc ctgcggggc tgtggccagc gtgccagcca ctgtgacact agccaatctc
 721 caggacttca agttagatgt gcagcacgtg attgaagtgg atgagggaaa cacagcagtc
 781 attgcctgcc acctgcctga gagccacccc aaagcccagg tccggtacag cgtcaaacaa
 841 gagtggctgg aggcctccag aggtaactac ctgatcatgc cctcagggaa cctccagatt
 901 gtgaatgcca gccaggagga cgagggcatg tacaagtgtg cagcctacaa cccagtgacc
 961 caggaagtga aaacctccgg ctccagcgac aggctacgtg tgcgccgctc caccgctgag
1021 gctgcccgca tcatctaccc cccagaggcc caaaccatca tcgtcaccaa aggccagagt
1081 ctcattctgg agtgtgtggc cagtggaatc ccaccccac gggtcacctg gccaaggat
1141 gggtccagtg tcaccggcta caacaagacg cgcttcctgc tgagcaacct cctcatcgac
1201 accaccagcg aggaggactc aggcacctac cgctgcatgg ccgacaatgg ggtttgggcag
1261 cccggggcag cggtcatcct ctacaatgtc caggtgttg aaccccctga ggtcaccatg
1321 gagctatccc agctggtcat ccctgggc cagagtgcca agcttacctg tgaggtgcgt
1381 gggaacccc cgccctccgt gctgtggctg aggaatgctg tgcccctcat ctccagccag
1441 cgcctccggc tctcccgcag ggccctgcgc gtgctcagca tggggcctga ggacgaaggc
1501 gtctaccagt gcatggccga gaacgaggtt gggagcgccc atgccgtagt ccagctgcgg
1561 acctccaggc caagcataac cccaaggcta tggcaggatg ctgagctggc tactggcaca
1621 cctcctgtat caccctccaa actcggcaac cctgagcaga tgctgagggg caaccggcg
1681 ctccccagac ccccaacgtc agtgggcct gcttcccgc agtgtccagg agagaagggg
1741 cagggggctc ccgccgaggc tccatcatc ctcagctcgc ccgcacctc caagacagac
1801 tcatatgaac tggtgtggcg gcctcggcat gagggcagtg gccgggcgcc aatcctctac
1861 tatgtggtga acaccgcaa ggtcacaaat tcctctgacg attggaccat ctctggcatt
1921 ccagccaacc agcaccgcct gacccctcac agacttgacc ccgggagctt gtatgaagtg
1981 gagatggcag cttacaactg tgcgggagag ggccagacag ccatggtcac cttccgaact
2041 ggacgcggc ccaaacccga gatcatggcc agcaaagagc agcagatcca gagagacgac
2101 cctggagcca gtccccagag cagcagccag ccagaccacg gccgcctctc cccccagaa
2161 gctcccgaca ggcccaccat ctccacggcc tccgagacct cagtgtacgt gacctggatt
2221 ccccgtggga atggtgggtt cccaatccag tccttccgtg tggagtacaa gaagctaaag
2281 aaagtgggag actggattct ggccaccagc gccatcccc atcgcggct gtccgtggag
2341 atcacgggcc tagagaaagg cacctcctac aagtttcgag tccgggctct gaacatgctg
2401 ggggagagcg agccagcgc cccctctcgg ccctacgtgg tgtcgggcta cagcggtcgc
2461 gtgtacgaga ggcccgtggc aggtccttat atcaccttca cggatgcggt caatgagacc
2521 accatcatgc tcaagtggat gtacatccca gcaagtaaca acaacacccc aatccatggc
2581 tttatatct attatcgacc cacagacagt gacaatgata gtgactacaa gaaggatatg
2641 gtggaagggg acaagtactg gcactccatc agccacctgc agccagagac ctcctacgac
2701 attaagatgc agtgcttcaa tgaaggaggg gagagcgagt tcagcaacgt gatgatctgt
2761 gagaccaaag ctcggaagtc ttctggccag cctggtcgac tgccaccccc aactctggcc
2821 ccaccacagc cgccccttcc tgaaaccata gagcggccgg tgggcactgg gccatggtg
2881 gctcgctcca cgacctgcc ctatctgatt gtcggggtcg tcctgggctc catcgttctc
2941 atcatcgtca ccttcatccc cttctgcttg tggagggcct ggtctaagca aaacataca
3001 acagacctgg gttttcctcg aagtgccctt ccaccctcct gcccgtatac tatggtgcca
```

FIG. 15A

```
3061 ttgggaggac tcccaggcca ccaggccagt ggacagccct acctcagtgg catcagtgga
3121 cgggcctgtg ctaatgggat ccacatgaat aggggctgcc cctcggctgc agtgggctac
3181 ccgggcatga agccccagca gcactgccca ggcgagcttc agcagcagag tgacaccagc
3241 agcctgctga ggcagaccca tcttggcaat ggatatgacc cccaaagtca ccagatcacg
3301 aggggtccca agtctagccc ggacgagggc tctttcttat acacactgcc cgacgactcc
3361 actcaccagc tgctgcagcc ccatcacgac tgctgccaac gccaggagca gcctgctgct
3421 gtgggccagt caggggtgag gagagccccc gacagtcctg tcctggaagc agtgtgggac
3481 cctccatttc actcagggcc cccatgctgc ttgggccttg tgccagttga agaggtggac
3541 agtcctgact cctgccaagt gagtggagga gactggtgtc cccagcaccc cgtagggcc
3601 tacgtaggac aggaacctgg aatgcagctc tccccggggc cactggtgcg tgtgtctttt
3661 gaaacaccac ctctcacaat ttaggcagaa gctgatatcc cagaaagact atatattgtt
3721 ttttttttaa aaaaaaaag aagaaaaag agacagagaa aattggtatt tattttcta
3781 ttatagccat atttatatat ttatgcactt gtaaataaat gtatatgttt tataattctg
3841 gagagacata aggagtccta cccgttgagg ttggagaggg aaaataaaga agctgccacc
3901 taacaggagt cacccaggaa agcaccgcac aggctggcgc gggacagact cctaacctgg
3961 ggcctctgca gtggcaggcg aggctgcagg aggcccacag ataagctggc aagaggaagg
4021 atcccaggca catggttcat cacgagcatg agggaacagc aaggggcacg gtatcacagc
4081 ctggagacac ccacacagat ggctggatcc ggtgctacgg gaaacatttt cctaagatgc
4141 ccatgagaac agaccaagat gtgtacagca ctatgagcat taaaaaacct tccagaatca
4201 ataatccgtg gcaacatatc tctgtaaaaa caaacactgt aacttctaaa taaatgttta
4261 gtcttccctg taaccttcaa aaaaaaaaaa aaa
```

FIG. 15B

Amino acid sequence of human BOC (SEQ ID NO: 2, RefSeq accession No. NP_150279)

```
   1 mlrgtmtawr gmrpevtlac lllatagcfa dlnevpqvtv qpastvqkpg gtvilgcvve
  61 pprmnvtwrl ngkelngsdd algvlithgt lvitalnnht vgryqcvarm pagavasvpa
 121 tvtlanlqdf kldvqhviev degntaviac hlpeshpkaq vrysvkqewl easrgnylim
 181 psgnlqivna sqedegmykc aaynpvtqev ktsgssdrlr vrrstaeaar iiyppeaqti
 241 ivtkgqslil ecvasgippp rvtwakdgss vtgynktrfl lsnllidtts eedsgtyrcm
 301 adngvgqpga avilynvqvf eppevtmels qlvipwgqsa kltcevrgnp ppsvlwlrna
 361 vplissqrlr lsrralrvls mgpedegvyq cmaenevgsa havvqlrtsr psitprlwqd
 421 aelatgtppv spsklgnpeq mlrgqpalpr pptsvgpasp qcpgekgqga paeapiilss
 481 prtsktdsye lvwrprhegs grapilyyvv khrkvtnssd dwtisgipan qhrltltrld
 541 pgslyevema ayncagegqt amvtfrtgrr pkpeimaske qqiqrddpga spqsssqpdh
 601 grlsppeapd rptistaset svyvtwiprg nggfpiqsfr veykklkkvg dwilatsaip
 661 psrlsveitg lekgtsykfr vralnmlges epsapsrpyv vsgysgrvye rpvagpyitf
 721 tdavnettim lkwmyipasn nntpihgfyi yyrptdsdnd sdykkdmveg dkywhsishl
 781 qpetsydikm qcfneggese fsnvmicetk arkssgqpgr lppptlappq pplpetierp
 841 vgtgamvars sdlpylivgv vlgsivliiv tfipfclwra wskqkhttdl gfprsalpps
 901 cpytmvplgg lpghqasgqp ylsgisgrac angihmnrgc psaavgypgm kpqqhcpgel
 961 qqqsdtssll rqthlgngyd pqshqitrgp ksspdegsfl ytlpddsthq llqphhdccq
1021 rqeqpaavgq sgvrrapdsp vleavwdppf hsgppcclgl vpveevdspd scqvsggdwc
1081 pqhpvgayvg qepgmqlspg plvrvsfetp plti
```

FIG. 15C

Nucleotide sequence of human SHH (SEQ ID NO: 3, RefSeq accession No. NM_000193)
Coding sequence: 152-1540

```
   1 gcgaggcagc cagcgaggga gagagcgagc gggcgagccg gagcgaggaa gggaaagcgc
  61 aagagagagc gcacacgcac acacccgccg cgcgcactcg cgcacggacc cgcacgggga
 121 cagctcggaa gtcatcagtt ccatgggcga gatgctgctg ctggcgagat gtctgctgct
 181 agtcctcgtc tcctcgctgc tggtatgctc gggactggcg tgcggaccgg gcaggggqtt
 241 cgggaagagg aggcacccca aaaagctgac ccctttagcc tacaagcagt ttatccccaa
 301 tgtggccgag aagaccctag gcgccagcgg aagtatgaa gggaagatct ccagaaactc
 361 cgagcgattt aaggaactca ccccaatta caacccgac atcatattta aggatgaaga
 421 aaacaccgga gcggacaggc tgatgactca gaggtgtaag acaagttga acgctttggc
 481 catctcggtg atgaaccagt ggccaggagt gaaactgcgg gtgaccgagg gctgggacga
 541 agatggccac cactcagagg agtctctgca ctacgagggc cgcgcagtgg acatcaccac
 601 gtctgaccgc gaccgcagca gtacggcat gctggcccgc ctggcggtgg aggccggctt
 661 cgactgggtg tactacgagt ccaaggcaca tatccactgc tcggtgaaag cagagaactc
 721 ggtggcggcc aaatcgggag gctgcttccc gggctcggcc acggtgcacc tggagcaggg
 781 cggcaccaag ctggtgaagg acctgagccc cggggaccgc gtgctggcgg cggacgacca
 841 gggccggctg ctctacagcg acttcctcac tttcctggac cgcgacgacg gcgccaagaa
 901 ggtcttctac gtgatcgaga cgcgggagcc gcgcgagcgc ctgctgctca ccgccgcgca
 961 cctgctcttt gtggcgccgc acaacgactc ggccaccggg gagcccgagg cgtcctcggg
1021 ctcggggccg ccttccgggg gcgcactggg gcctcgggcg ctgttcgcca gccgcgtgcg
1081 cccgggccag cgcgtgtacg tggtggccga gcgtgacggg gaccgccggc tcctgcccgc
1141 cgctgtgcac agcgtgaccc taagcgagga ggccgcgggc gcctacgcgc cgctcacggc
1201 ccagggcacc attctcatca accgggtgct ggcctcgtgc tacgcggtca tcgaggagca
1261 cagctgggcg caccgggcct tcgcgccctt ccgcctggcg cacgcgctcc tggctgcact
1321 ggcgcccgcg cgcacggacc gcggcgggga cagcggcggc ggggaccgcg ggggcggcgg
1381 cggcagagta gccctaaccg ctccaggtgc tgccgacgct ccgggtgcgg gggccaccgc
1441 gggcatccac tggtactcgc agctgctcta ccaaataggc acctggctcc tggacagcga
1501 ggccctgcac ccgctgggca tggcggtcaa gtccagctga agccgggggg ccgggggagg
1561 ggcgcgggag ggggcg
```

FIG. 16A

Amino acid sequence of human SHH (SEQ ID NO: 4, RefSeq accession No. NP_000184)

```
   1 mlllarclll vlvssllvcs glacgpgrgf gkrrhpkklt playkqfipn vaektlgasg
  61 ryegkisrns erfkeltpny npdiifkdee ntgadrlmtq rckdklnala isvmnqwpgv
 121 klrvtegwde dghhseeslh yegravditt sdrdrskygm larlaveagf dwvyyeskah
 181 ihcsvkaens vaaksggcfp gsatvhleqg gtklvkdlsp gdrvlaaddq grllysdflt
 241 fldrddgakk vfyvietrep rerllltaah llfvaphnds atgepeassg sgppsggalg
 301 pralfasrvr pgqrvyvvae rdgdrrllpa avhsvtlsee aagayaplta qqgtilinrvl
 361 ascyavieeh swahrafapf rlahallaal apartdrggd sgggdrgggg grvaltapga
 421 adapgagata gihwysqlly qigtwlldse alhplgmavk ss
```

FIG. 16B

Coding sequence of murine BOC (SEQ ID NO: 9, derived from RefSeq accession No. NM_172506)

```
atgacgacgtgc cgaagagagc ggcctatact tacactgctt tggattctca tggccacagc aggctgcctt
gctgatttga atgaggttcc tcaggtcaca gtccagccca tgtccactgt ccagaagctg ggaggaactg
tgatcctggg ctgtgtggtg gagccaccat ggatgaacgt gacttggcgc ttcaacggaa aggagctaaa
tggctctgat gatgctctgg gtgtcttcat cacccgtggg acccttgtca ttgctgccct caacaaccac
actgtgggac ggtaccagtg tgtggcacgg atgcctgcag gagctgtggc cagtgtgcca gccacagtga
cgctagccaa tctccaggac tttaaattag atgtgcagca tgtgattgaa gtagacgagg ggaacacagc
cgtcattgcc tgccacctgc ctgagagcca cccaaaagcc caggtccggt acagtgtcaa acaggagtgg
ctggaggcct ctagagacaa ctacctgatc atgccatccg ggaatctcca aattgtcaat gccagccaag
aggacgaagg catgtacaag tgtgccgcct acaaccccgt gacccaggaa gtgaaaacct ccggctccgg
cgacaggctg cgcgtgcgcc ggtccactgc tgaggctgcc cgcatcatct cccactgga agcccagacc
gtcattgtca ccaaaggcca gagtctcata ctggagtgtg tggccagtgg aatcccacca cctcgagtca
catgggccaa ggatgggtcc agcattgctg cctataacaa gactcgcttc ctgctgagta atttgcttat
tgacaccacc agcgaggagg actcaggcac ctaccgatgt atggccagca atggggttgg ggatcctggg
gcagcagtca tcctctacaa tgtccaggtg ttcgaacccc tgaggtcac ggtggagctg tcccagctgg
tcatcccatg gggccagagt gcaaagctca cctgtgaggt tcgaggaaac cccccaccct ctgtactatg
gctgaggaat gcagtgcccc tcacctccag ccagcgcctc cggctgtcac gtagagccct gcgggtggtc
agtgttgggc cagaggacga aggcgtgtac cagtgcatgg ctgagaatgc ggttggcagt gcccacgctg
tggtccaact gaggaccgcc cggccagaca caacccctgag acccggggagg gataccaagc cgattgctgc
cacacccccc atgccaccct ccagacccag cagacctgac cagatgcttc gggaacaacc ggggcttgtt
aagcccccaa cgtcgtcggt acagcctact tccctgaagt gcccgggaga agagcaggta gccctgcag
aggcacctat catcctcagc tcacccgga cctccaagac ggactcctat gagctgtgt ggcggcctcg
ccatgagggg agcagccgga cacccatcct gtactacgta gtgaagcatc gtaaggtcac gaactcctct
gacgactgga ccatttctgg cattccagcc aaccagcacc gcctcaccct gaccaggctt gaccctggaa
gcttgtacga agtggagatg gcagcctaca actgtgctgg cgagggccag acagctatgg tcaccttccg
aacaggacgg cggcccaaac ctgagatcgt ggccagtaag gagcagcaga tccagagaga tgaccctggt
gccagtctcc agagcagcag ccagcctgac catggccgcc tctccccccc agaagctcca gacagaccca
ccatctccac agcttctgag acctccgtgt acgtaacctg gattccccga gggaacgcg gcttcccgat
tcagtctttc cgtgtagagt acaagaagct aaaaaaagtg ggagattgga tactggctac cagtgccata
cctccctcga ggctctctgt ggagatcaca ggcctagaga aaggtatttc ttacaagttc cgagttcgtg
ctttgaacat gttagggagg agtgagccca gtgctccctc ccggcccctac gtgtgtcag gctacagtgg
ccgtgtatat gagaggcccg tggcaggacc ttacatcacc ttcactgatg cagtcaatga gaccactatt
atgctcaagt ggatgtatat cccagccagt aacaacaaca cccaatcca tggcttctat atctactacc
gacccacaga cagtgacaat gacagtgact acaagaagga catggtagaa ggggacaggt actggcactc
catcagccac ctgcagccag agacttccta tgacattaaa atgcagtgct caatgaagg aggggagagc
gagttcagca atgtcatgat ctgcgagacc aaagctcgga aattttctgg tcagcctgga agacccccac
ccttgactct agctccacca cagcctccgc cctagaaac catggaacgg ccgtgggca ctggagccat
ggtggcacgg gccagcgacc tgcctatct gattgtcggg gttgttctgg gtctatagt cctcatcatc
gtcaccttca tcccttctg cctatggagg gcctggtcta agcagaaaca cacaacagat ctgggttttc
ctcggagtgc cctcctgtct tcttcgtgcc agtacacaat ggtgccattg gagggactc caggtcacca
agccaacggg cagccctacc ttggtggcgt cagtggcgg gcctgtgtca gtcgagtgca cggaagcagg
ggctgccctg ctgctacagt gggctgtcca ggcaggaagc ctcagcagca ctgcccaggg agcttgccc
    agcggga agacaccaac agccaactga ggcagcccat tgttagcaac ggatatgacc tccagaacca
gcaggttgcc agaggtcccc agtgtgcctc aggagtagga gctttcttat acacgctgcc tgatgactca
actcaccagc tgctccaacc tcaagactgc tgtcacctcc agaagcaacc cgtcaccaca tgccaaacag
cagtgaggcg aacgtctgaa agtcctggac tagaatcttc atgggaccct ccatatcatt cagggcccca
gtgctgtttta ggtcttgtac cagttgaaga agtagacagt tctgactcct gccaagtggg tggaggagac
tggagttccc agcatccatc agggacctac acaggacagg aacgtgggat gcggttctcg cctagcccat
    cagttcatgt gtcctttgaa acaccacctc ccacaattgg accggtcgccaccatggtgagctag
```

FIG. 17A

Amino acid sequence of murine BOC (SEQ ID NO: 10)

MTTCRRERPILTLLWILMATAGCLADLNEVPQVTVQPMSTVQKLGGTVILGCVVEPPWMN
VTWRFNGKELNGSDDALGVFITRGTLVIAALNNHTVGRYQCVARMPAGAVASVPATVTLA
NLQDFKLDVQHVIEVDEGNTAVIACHLPESHPKAQVRYSVKQEWLEASRDNYLIMPSGNL
QIVNASQEDEGMYKCAAYNPVTQEVKTSGSGDRLRVRRSTAEAARIIYPLEAQTVIVTKG
QSLILECVASGIPPPRVTWAKDGSSIAAYNKTRFLLSNLLIDTTSEEDSGTYRCMASNGV
GDPGAAVILYNVQVFEPPEVTVELSQLVIPWGQSAKLTCEVRGNPPPSVLWLRNAVPLTS
SQRLRLSRRALRVVSVGPEDEGVYQCMAENAVGSAHAVVQLRTARPDTTLRPGRDTKPIA
ATPPMPPSRPSRPDQMLREQPGLVKPPTSSVQPTSLKCPGEEQVAPAEAPIILSSPRTSK
TDSYELVWRPRHEGSSRTPILYYVVKHRKVTNSSDDWTISGIPANQHRLTLTRLDPGSLY
EVEMAAYNCAGEGQTAMVTFRTGRRPKPEIVASKEQQIQRDDPGASLQSSSQPDHGRLSP
PEAPDRPTISTASETSVYVTWIPRGNGGFPIQSFRVEYKKLKKVGDWILATSAIPPSRLS
VEITGLEKGISYKFRVRALNMLGESEPSAPSRPYVVSGYSGRVYERPVAGPYITFTDAVN
ETTIMLKWMYIPASNNNTPIHGFYIYYRPTDSDNDSDYKKDMVEGDRYWHSISHLQPETS
YDIKMQCFNEGGESEFSNVMICETKARKFSGQPGRPPPLTLAPPQPPPLETMERPVGTGA
MVARASDLPYLIVGVVLGSIVLIIVTFIPFCLWRAWSKQKHTTDLGFPRSALLSSSCQYT
MVPLEGLPGHQANGQPYLGGVSGRACVSRVHGSRGCPAATVGCPGRKPQQHCPGELAQRE
DTNSQLRQPIVSNGYDLQNQQVARGPQCASGVGAFLYTLPDDSTHQLLQPQDCCHLQKQP
VTTCQTAVRRTSESPGLESSWDPPYHSGPQCCLGLVPVEEVDSSDSCQVGGGDWSSQHPS
GTYTGQERGMRFSPSPSVHVSFETPPPTIGPVATMVS

FIG. 17B

Alignment of the human (top) and mouse (bottom) BOC amino acid sequences

ID (including gaps) 86.6%, coverage (of both) 99.8%, score 95589

```
0006 MTAWRGMRPEVTLACLLLATAGCFADLNEVPQVTVQPASTVQKPGGTVILGCVVEPPRMN 0065
     ||  |  || +||  +|+|||||  ||||||||||||| |||||  ||||||||||||| ||
0001 MTTCRRERPILTLLWILMATAGCLADLNEVPQVTVQPMSTVQKLGGTVILGCVVEPPWMN 0060

0066 VTWRLNGKELNGSDDALGVLITHGTLVITALNNHTVGRYQCVARMPAGAVASVPATVTLA 0125
     ||||  ||||||||||||||  ||  |||||  ||||||||||||||||||||||||||
0061 VTWRFNGKELNGSDDALGVFITRGTLVIAALNNHTVGRYQCVARMPAGAVASVPATVTLA 0120

0126 NLQDFKLDVQHVIEVDEGNTAVIACHLPESHPKAQVRYSVKQEWLEASRGNYLIMPSGNL 0185
     |||||||||||||||||||||||||||||||||||||||||||||||| |||||||||||
0121 NLQDFKLDVQHVIEVDEGNTAVIACHLPESHPKAQVRYSVKQEWLEASRDNYLIMPSGNL 0180

0186 QIVNASQEDEGMYKCAAYNPVTQEVKTSGSSDRLRVRRSTAEAARIIYPPEAQTIIVTKG 0245
     ||||||||||||||||||||||||||||||  ||||||||||||||||  ||||+||||| 
0181 QIVNASQEDEGMYKCAAYNPVTQEVKTSGSGDRLRVRRSTAEAARIIYPLEAQTVIVTKG 0240

0246 QSLILECVASGIPPPRVTWAKDGSSVTGYNKTRFLLSNLLIDTTSEEDSGTYRCMADNGV 0305
     ||||||||||||||||||||||||+  |||||||||||||||||||||||||||||  |||
0241 QSLILECVASGIPPPRVTWAKDGSSIAAYNKTRFLLSNLLIDTTSEEDSGTYRCMASNGV 0300

0306 GQPGAAVILYNVQVFEPPEVTMELSQLVIPWGQSAKLTCEVRGNPPPSVLWLRNAVPLIS 0365
     |  |||||||||||||||||+||||||||||||||||||||||||||||||||||||| |
0301 GDPGAAVILYNVQVFEPPEVTVELSQLVIPWGQSAKLTCEVRGNPPPSVLWLRNAVPLTS 0360

0366 SQRLRLSRRALRVLSMGPEDEGVYQCMAENEVGSAHAVVQLRTSRPSITPRLWQDAELAT 0425
     ||||||||||+|+||||||||||||||||| |||||||||||||+||  |  |  +|  +
0361 SQRLRLSRRALRVVSVGPEDEGVYQCMAENAVGSAHAVVQLRTARPDTTLRPGRDTKPIA 0420

0426 GTPPVSPSKLGNPEQMLRGQPALPRPPT-SVGPASPQCPGEKGQGAPAEAPIILSSPRTS 0484
      |||+ ||+   |+|||| ||  |  +|||  ||  |  |  +||||+ | |||||||||||
0421 ATPPMPPSRPSRPDQMLREQPGLVKPPTSSVQPTSLKCPGEE-QVAPAEAPIILSSPRTS 0479

0485 KTDSYELVWRPRHEGSGRAPILYYVVKHRKVTNSSDDWTISGIPANQHRLTLTRLDPGSL 0544
     |||||||||||||||| |  ||||||||||||||||||||||||||||||||||||||||
0480 KTDSYELVWRPRHEGSSRTPILYYVVKHRKVTNSSDDWTISGIPANQHRLTLTRLDPGSL 0539

0545 YEVEMAAYNCAGEGQTAMVTFRTGRRPKPEIMASKEQQIQRDDPGASPQSSSQPDHGRLS 0604
     |||||||||||||||||||||||||||||||+||||||||||||||| |||||||||||||
0540 YEVEMAAYNCAGEGQTAMVTFRTGRRPKPEIVASKEQQIQRDDPGASLQSSSQPDHGRLS 0599

0605 PPEAPDRPTISTASETSVYVTWIPRGNGGFPIQSFRVEYKKLKKVGDWILATSAIPPSRL 0664
     ||||||||||||||||||||||||||||||||||||||||||||||||||||||||||||
0600 PPEAPDRPTISTASETSVYVTWIPRGNGGFPIQSFRVEYKKLKKVGDWILATSAIPPSRL 0659

0665 SVEITGLEKGTSYKFRVRALNMLGESEPSAPSRPYVVSGYSGRVYERPVAGPYITFTDAV 0724
     ||||||||||| ||||||||||||||||||||||||||||||||||||||||||||||||
0660 SVEITGLEKGISYKFRVRALNMLGESEPSAPSRPYVVSGYSGRVYERPVAGPYITFTDAV 0719
```

FIG. 18A

```
0725 NETTIMLKWMYIPASNNNTPIHGFYIYYRPTDSDNDSDYKKDMVEGDKYWHSISHLQPET 0784
     |||||||||||||||||||||||||||||||||||||||||||||+||||||||||||
0720 NETTIMLKWMYIPASNNNTPIHGFYIYYRPTDSDNDSDYKKDMVEGDRYWHSISHLQPET 0779

0785 SYDIKMQCFNEGGESEFSNVMICETKARKSSGQPGRLPPPTLAPPQPPLPETIERPVTG 0844
     |||||||||||||||||||||||||||||| |||||| || |||||||| ||+|||||||
0780 SYDIKMQCFNEGGESEFSNVMICETKARKFSGQPGRPPPLTLAPPQPPPLETMERPVGTG 0839

0845 AMVARSSDLPYLIVGVVLGSIVLIIVTFIPFCLWRAWSKQKHTTDLGFPRSA-LPPSCPY 0903
     |||||+|||||||||||||||||||||||||||||||||||||||||||||| |  || |
0840 AMVARASDLPYLIVGVVLGSIVLIIVTFIPFCLWRAWSKQKHTTDLGFPRSALLSSSCQY 0899

0904 TMVPLGGLPGHQASGQPYLSGISGRACANGIHMNRGCPSAAVGYPGMKPQQHCPGELQQQ 0963
     ||||| ||||||+||||| |+||||| + +| +||||+| || ||  ||||||||||| |+
0900 TMVPLEGLPGHQANGQPYLGGVSGRACVSRVHGSRGCPAATVGCPGRKPQQHCPGELAQR 0959

0964 SDTSSLLRQTHLGNGYDPQSHQITRGPKSSPDEGSFLYTLPDDSTHQLLQPHHDCCQRQE 1023
      ||+| |||   + |||| |+ |+ |||+ +    |+|||||||||||||||| |||   |+
0960 EDTNSQLRQPIVSNGYDLQNQQVARGPQCASGVGAFLYTLPDDSTHQLLQP-QDCCHLQK 1018

1024 QPAAVGQSGVRRAPDSPVLEAVWDPPFHSGPPCCLGLVPVEEVDSPDSCQVSGGDWCPQH 1083
     ||       |+ ||| +|| ||+ ||||+|||| ||||||||||||| |||| ||||  ||
1019 QPVTTCQTAVRRTSESPGLESSWDPPYHSGPQCCLGLVPVEEVDSSDSCQVGGGDWSSQH 1078

1084 PVGAYVGQEPGMQLSPGPLVRVSFETPPLTI 1114
     | | ||| ||+ || | | |||||||| ||
1079 PSGTYTGQERGMRFSPSPSVHVSFETPPPTI 1109
```

FIG. 18B

Lack of detection of soluble mBoc in tissue-culture media using an anti-Boc (intracellular) antibody

FIG. 21C

Detection of soluble mBoc in tissue-culture media using an anti-Boc (extracellular) antibody

FIG. 21D

SEQUENCE LISTING

```
<160> NUMBER OF SEQ ID NOS: 15

<210> SEQ ID NO 1
<211> LENGTH: 4293
<212> TYPE: DNA
<213> ORGANISM: Homo sapiens
<220> FEATURE:
<221> NAME/KEY: CDS
<222> LOCATION: (340)..(3684)

<400> SEQUENCE: 1
gtttctcata gttggcgtct tctaaaggaa aaacactaaa atgaggaact cagcggaccg        60
ggagcgacgc agcttgaggg aagcatccct agctgttggc gcagaggggc gaggctgaag       120
ccgagtggcc cgaggtgtct gaggggctgg ggcaaaggtg aaagagtttc agaacaagct       180
tcctggaacc catgacccat gaagtcttgt cgacatttat accgtctgag ggtagcagct       240
cgaaagtaga agaagtggag tgttgccagg gacggcagta tctctttgtg tgaccctggc       300
ggcttatggg acgttggctt cagacctttg tgatacacc atg ctg cgt ggg acg        354
                                            Met Leu Arg Gly Thr
                                             1               5 atg acg gcg tgg aga gga atg agg cct gag gtc aca ctg gct tgc ctc        402
Met Thr Ala Trp Arg Gly Met Arg Pro Glu Val Thr Leu Ala Cys Leu
             10                  15                  20 ctc cta gcc aca gca ggc tgc ttt gct gac ttg aac gag gtc cct cag        450
Leu Leu Ala Thr Ala Gly Cys Phe Ala Asp Leu Asn Glu Val Pro Gln
         25                  30                  35 gtc acc gtc cag cct gcg tcc acc gtc cag aag ccc gga ggc act gtg        498
Val Thr Val Gln Pro Ala Ser Thr Val Gln Lys Pro Gly Gly Thr Val
     40                  45                  50 atc ttg ggc tgc gtg gtg gaa cct cca agg atg aat gta acc tgg cgc        546
Ile Leu Gly Cys Val Val Glu Pro Pro Arg Met Asn Val Thr Trp Arg
 55                  60                  65 ctg aat gga aag gag ctg aat ggc tcg gat gat gct ctg ggt gtc ctc        594
Leu Asn Gly Lys Glu Leu Asn Gly Ser Asp Asp Ala Leu Gly Val Leu
 70                  75                  80                  85 atc acc cac ggg acc ctc gtc atc act gcc ctt aac aac cac act gtg        642
Ile Thr His Gly Thr Leu Val Ile Thr Ala Leu Asn Asn His Thr Val
             90                  95                 100
```

-continued

| | |
|---|---|
| gga cgg tac cag tgt gtg gcc cgg atg cct gcg ggg gct gtg gcc agc<br>Gly Arg Tyr Gln Cys Val Ala Arg Met Pro Ala Gly Ala Val Ala Ser<br>              105                  110                115 | 690 |
| gtg cca gcc act gtg aca cta gcc aat ctc cag gac ttc aag tta gat<br>Val Pro Ala Thr Val Thr Leu Ala Asn Leu Gln Asp Phe Lys Leu Asp<br>120                  125                  130 | 738 |
| gtg cag cac gtg att gaa gtg gat gag gga aac aca gca gtc att gcc<br>Val Gln His Val Ile Glu Val Asp Glu Gly Asn Thr Ala Val Ile Ala<br>              135                  140                145 | 786 |
| tgc cac ctg cct gag agc cac ccc aaa gcc cag gtc cgg tac agc gtc<br>Cys His Leu Pro Glu Ser His Pro Lys Ala Gln Val Arg Tyr Ser Val<br>150                  155                  160                165 | 834 |
| aaa caa gag tgg ctg gag gcc tcc aga ggt aac tac ctg atc atg ccc<br>Lys Gln Glu Trp Leu Glu Ala Ser Arg Gly Asn Tyr Leu Ile Met Pro<br>              170                  175                180 | 882 |
| tca ggg aac ctc cag att gtg aat gcc agc cag gag gac gag ggc atg<br>Ser Gly Asn Leu Gln Ile Val Asn Ala Ser Gln Glu Asp Glu Gly Met<br>                  185                  190                195 | 930 |
| tac aag tgt gca gcc tac aac cca gtg acc cag gaa gtg aaa acc tcc<br>Tyr Lys Cys Ala Ala Tyr Asn Pro Val Thr Gln Glu Val Lys Thr Ser<br>200                  205                  210 | 978 |
| ggc tcc agc gac agg cta cgt gtg cgc cgc tcc acc gct gag gct gcc<br>Gly Ser Ser Asp Arg Leu Arg Val Arg Arg Ser Thr Ala Glu Ala Ala<br>              215                  220                225 | 1026 |
| cgc atc atc tac ccc cca gag gcc caa acc atc atc gtc acc aaa ggc<br>Arg Ile Ile Tyr Pro Pro Glu Ala Gln Thr Ile Ile Val Thr Lys Gly<br>230                  235                  240                245 | 1074 |
| cag agt ctc att ctg gag tgt gtg gcc agt gga atc cca ccc cca cgg<br>Gln Ser Leu Ile Leu Glu Cys Val Ala Ser Gly Ile Pro Pro Pro Arg<br>                  250                  255                260 | 1122 |
| gtc acc tgg gcc aag gat ggg tcc agt gtc acc ggc tac aac aag acg<br>Val Thr Trp Ala Lys Asp Gly Ser Ser Val Thr Gly Tyr Asn Lys Thr<br>              265                  270                275 | 1170 |
| cgc ttc ctg ctg agc aac ctc ctc atc gac acc acc agc gag gag gac<br>Arg Phe Leu Leu Ser Asn Leu Leu Ile Asp Thr Thr Ser Glu Glu Asp<br>                  280                  285                290 | 1218 |
| tca ggc acc tac cgc tgc atg gcc gac aat ggg gtt ggg cag ccc ggg<br>Ser Gly Thr Tyr Arg Cys Met Ala Asp Asn Gly Val Gly Gln Pro Gly<br>              295                  300                305 | 1266 |
| gca gcg gtc atc ctc tac aat gtc cag gtg ttt gaa ccc cct gag gtc<br>Ala Ala Val Ile Leu Tyr Asn Val Gln Val Phe Glu Pro Pro Glu Val<br>310                  315                  320                325 | 1314 |
| acc atg gag cta tcc cag ctg gtc atc ccc tgg ggc cag agt gcc aag<br>Thr Met Glu Leu Ser Gln Leu Val Ile Pro Trp Gly Gln Ser Ala Lys<br>                  330                  335                340 | 1362 |
| ctt acc tgt gag gtg cgt ggg aac ccc ccg ccc tcc gtg ctg tgg ctg<br>Leu Thr Cys Glu Val Arg Gly Asn Pro Pro Pro Ser Val Leu Trp Leu<br>              345                  350                355 | 1410 |
| agg aat gct gtg ccc ctc atc tcc agc cag cgc ctc cgg ctc tcc cgc<br>Arg Asn Ala Val Pro Leu Ile Ser Ser Gln Arg Leu Arg Leu Ser Arg<br>                  360                  365                370 | 1458 |
| agg gcc ctg cgc gtg ctc agc atg ggg cct gag gac gaa ggc gtc tac<br>Arg Ala Leu Arg Val Leu Ser Met Gly Pro Glu Asp Glu Gly Val Tyr<br>375                  380                  385 | 1506 |
| cag tgc atg gcc gag aac gag gtt ggg agc gcc cat gcc gta gtc cag<br>Gln Cys Met Ala Glu Asn Glu Val Gly Ser Ala His Ala Val Val Gln<br>390                  395                  400                405 | 1554 |
| ctg cgg acc tcc agg cca agc ata acc cca agg cta tgg cag gat gct<br>Leu Arg Thr Ser Arg Pro Ser Ile Thr Pro Arg Leu Trp Gln Asp Ala<br>                  410                  415                420 | 1602 |

```
gag ctg gct act ggc aca cct cct gta tca ccc tcc aaa ctc ggc aac      1650
Glu Leu Ala Thr Gly Thr Pro Pro Val Ser Pro Ser Lys Leu Gly Asn
            425                 430                 435 cct gag cag atg ctg agg ggg caa ccg gcg ctc ccc aga ccc cca acg      1698
Pro Glu Gln Met Leu Arg Gly Gln Pro Ala Leu Pro Arg Pro Pro Thr
        440                 445                 450 tca gtg ggg cct gct tcc ccg cag tgt cca gga gag aag ggg cag ggg      1746
Ser Val Gly Pro Ala Ser Pro Gln Cys Pro Gly Glu Lys Gly Gln Gly
    455                 460                 465 gct ccc gcc gag gct ccc atc atc ctc agc tcg ccc cgc acc tcc aag      1794
Ala Pro Ala Glu Ala Pro Ile Ile Leu Ser Ser Pro Arg Thr Ser Lys
470                 475                 480                 485 aca gac tca tat gaa ctg gtg tgg cgg cct cgg cat gag ggc agt ggc      1842
Thr Asp Ser Tyr Glu Leu Val Trp Arg Pro Arg His Glu Gly Ser Gly
                490                 495                 500 cgg gcg cca atc ctc tac tat gtg gtg aaa cac cgc aag gtc aca aat      1890
Arg Ala Pro Ile Leu Tyr Tyr Val Val Lys His Arg Lys Val Thr Asn
            505                 510                 515 tcc tct gac gat tgg acc atc tct ggc att cca gcc aac cag cac cgc      1938
Ser Ser Asp Asp Trp Thr Ile Ser Gly Ile Pro Ala Asn Gln His Arg
        520                 525                 530 ctg acc ctc acc aga ctt gac ccc ggg agc ttg tat gaa gtg gag atg      1986
Leu Thr Leu Thr Arg Leu Asp Pro Gly Ser Leu Tyr Glu Val Glu Met
    535                 540                 545 gca gct tac aac tgt gcg gga gag ggc cag aca gcc atg gtc acc ttc      2034
Ala Ala Tyr Asn Cys Ala Gly Glu Gly Gln Thr Ala Met Val Thr Phe
550                 555                 560                 565 cga act gga cgg cgg ccc aaa ccc gag atc atg gcc agc aaa gag cag      2082
Arg Thr Gly Arg Arg Pro Lys Pro Glu Ile Met Ala Ser Lys Glu Gln
                570                 575                 580 cag atc cag aga gac gac cct gga gcc agt ccc cag agc agc agc cag      2130
Gln Ile Gln Arg Asp Asp Pro Gly Ala Ser Pro Gln Ser Ser Ser Gln
            585                 590                 595 cca gac cac ggc cgc ctc tcc ccc cca gaa gct ccc gac agg ccc acc      2178
Pro Asp His Gly Arg Leu Ser Pro Pro Glu Ala Pro Asp Arg Pro Thr
        600                 605                 610 atc tcc acg gcc tcc gag acc tca gtg tac gtg acc tgg att ccc cgt      2226
Ile Ser Thr Ala Ser Glu Thr Ser Val Tyr Val Thr Trp Ile Pro Arg
    615                 620                 625 ggg aat ggt ggg ttc cca atc cag tcc ttc cgt gtg gag tac aag aag      2274
Gly Asn Gly Gly Phe Pro Ile Gln Ser Phe Arg Val Glu Tyr Lys Lys
630                 635                 640                 645 cta aag aaa gtg gga gac tgg att ctg gcc acc agc gcc atc ccc cca      2322
Leu Lys Lys Val Gly Asp Trp Ile Leu Ala Thr Ser Ala Ile Pro Pro
                650                 655                 660 tcg cgg ctg tcc gtg gag atc acg ggc cta gag aaa ggc acc tcc tac      2370
Ser Arg Leu Ser Val Glu Ile Thr Gly Leu Glu Lys Gly Thr Ser Tyr
            665                 670                 675 aag ttt cga gtc cgg gct ctg aac atg ctg ggg gag agc gag ccc agc      2418
Lys Phe Arg Val Arg Ala Leu Asn Met Leu Gly Glu Ser Glu Pro Ser
        680                 685                 690 gcc ccc tct cgg ccc tac gtg gtg tcg ggc tac agc ggt cgc gtg tac      2466
Ala Pro Ser Arg Pro Tyr Val Val Ser Gly Tyr Ser Gly Arg Val Tyr
    695                 700                 705 gag agg ccc gtg gca ggt cct tat atc acc ttc acg gat gcg gtc aat      2514
Glu Arg Pro Val Ala Gly Pro Tyr Ile Thr Phe Thr Asp Ala Val Asn
710                 715                 720                 725 gag acc acc atc atg ctc aag tgg atg tac atc cca gca agt aac aac      2562
Glu Thr Thr Ile Met Leu Lys Trp Met Tyr Ile Pro Ala Ser Asn Asn
                730                 735                 740
```

```
aac acc cca atc cat ggc ttt tat atc tat tat cga ccc aca gac agt         2610
Asn Thr Pro Ile His Gly Phe Tyr Ile Tyr Tyr Arg Pro Thr Asp Ser
            745                 750                 755 gac aat gat agt gac tac aag aag gat atg gtg gaa ggg gac aag tac         2658
Asp Asn Asp Ser Asp Tyr Lys Lys Asp Met Val Glu Gly Asp Lys Tyr
        760                 765                 770 tgg cac tcc atc agc cac ctg cag cca gag acc tcc tac gac att aag         2706
Trp His Ser Ile Ser His Leu Gln Pro Glu Thr Ser Tyr Asp Ile Lys
    775                 780                 785 atg cag tgc ttc aat gaa gga ggg gag agc gag ttc agc aac gtg atg         2754
Met Gln Cys Phe Asn Glu Gly Gly Glu Ser Glu Phe Ser Asn Val Met
790                 795                 800                 805 atc tgt gag acc aaa gct cgg aag tct tct ggc cag cct ggt cga ctg         2802
Ile Cys Glu Thr Lys Ala Arg Lys Ser Ser Gly Gln Pro Gly Arg Leu
            810                 815                 820 cca ccc cca act ctg gcc cca cca cag ccg ccc ctt cct gaa acc ata         2850
Pro Pro Pro Thr Leu Ala Pro Pro Gln Pro Pro Leu Pro Glu Thr Ile
        825                 830                 835 gag cgg ccg gtg ggc act ggg gcc atg gtg gct cgc tcc agc gac ctg         2898
Glu Arg Pro Val Gly Thr Gly Ala Met Val Ala Arg Ser Ser Asp Leu
    840                 845                 850 ccc tat ctg att gtc ggg gtc gtc ctg ggc tcc atc gtt ctc atc atc         2946
Pro Tyr Leu Ile Val Gly Val Val Leu Gly Ser Ile Val Leu Ile Ile
855                 860                 865 gtc acc ttc atc ccc ttc tgc ttg tgg agg gcc tgg tct aag caa aaa         2994
Val Thr Phe Ile Pro Phe Cys Leu Trp Arg Ala Trp Ser Lys Gln Lys
870                 875                 880                 885 cat aca aca gac ctg ggt ttt cct cga agt gcc ctt cca ccc tcc tgc         3042
His Thr Thr Asp Leu Gly Phe Pro Arg Ser Ala Leu Pro Pro Ser Cys
            890                 895                 900 ccg tat act atg gtg cca ttg gga gga ctc cca ggc cac cag gcc agt         3090
Pro Tyr Thr Met Val Pro Leu Gly Gly Leu Pro Gly His Gln Ala Ser
        905                 910                 915 gga cag ccc tac ctc agt ggc atc agt gga cgg gcc tgt gct aat ggg         3138
Gly Gln Pro Tyr Leu Ser Gly Ile Ser Gly Arg Ala Cys Ala Asn Gly
    920                 925                 930 atc cac atg aat agg ggc tgc ccc tcg gct gca gtg ggc tac ccg ggc         3186
Ile His Met Asn Arg Gly Cys Pro Ser Ala Ala Val Gly Tyr Pro Gly
935                 940                 945 atg aag ccc cag cag cac tgc cca ggc gag ctt cag cag cag agt gac         3234
Met Lys Pro Gln Gln His Cys Pro Gly Glu Leu Gln Gln Gln Ser Asp
950                 955                 960                 965 acc agc agc ctg ctg agg cag acc cat ctt ggc aat gga tat gac ccc         3282
Thr Ser Ser Leu Leu Arg Gln Thr His Leu Gly Asn Gly Tyr Asp Pro
            970                 975                 980 caa agt cac cag atc acg agg ggt ccc aag tct agc ccg gac gag ggc         3330
Gln Ser His Gln Ile Thr Arg Gly Pro Lys Ser Ser Pro Asp Glu Gly
        985                 990                 995 tct ttc tta tac aca ctg ccc gac gac tcc act cac cag ctg ctg             3375
Ser Phe Leu Tyr Thr Leu Pro Asp Asp Ser Thr His Gln Leu Leu
        1000                1005                1010 cag ccc cat cac gac tgc tgc caa cgc cag gag cag cct gct gct             3420
Gln Pro His His Asp Cys Cys Gln Arg Gln Glu Gln Pro Ala Ala
        1015                1020                1025 gtg ggc cag tca ggg gtg agg aga gcc ccc gac agt cct gtc ctg             3465
Val Gly Gln Ser Gly Val Arg Arg Ala Pro Asp Ser Pro Val Leu
        1030                1035                1040 gaa gca gtg tgg gac cct cca ttt cac tca ggg ccc cca tgc tgc             3510
Glu Ala Val Trp Asp Pro Pro Phe His Ser Gly Pro Pro Cys Cys
        1045                1050                1055
```

```
ttg ggc ctt gtg cca gtt gaa gag gtg gac agt cct gac tcc tgc    3555
Leu Gly Leu Val Pro Val Glu Glu Val Asp Ser Pro Asp Ser Cys
        1060                1065                1070 caa gtg agt gga gga gac tgg tgt ccc cag cac ccc gta ggg gcc    3600
Gln Val Ser Gly Gly Asp Trp Cys Pro Gln His Pro Val Gly Ala
    1075                1080                1085 tac gta gga cag gaa cct gga atg cag ctc tcc ccg ggg cca ctg    3645
Tyr Val Gly Gln Glu Pro Gly Met Gln Leu Ser Pro Gly Pro Leu
1090                1095                1100 gtg cgt gtg tct ttt gaa aca cca cct ctc aca att tag gcagaagctg 3694
Val Arg Val Ser Phe Glu Thr Pro Pro Leu Thr Ile
        1105                1110 atatcccaga aagactatat attgtttttt ttttaaaaaa aaaaagaaga aaaaagagac 3754 agagaaaatt ggtatttatt tttctattat agccatattt atatatttat gcacttgtaa 3814 ataaatgtat atgttttata attctggaga acataagga gtcctacccg ttgaggttgg  3874
agagggaaaa taaagaagct gccacctaac aggagtcacc caggaaagca ccgcacaggc  3934
tggcgcggga cagactccta acctggggcc tctgcagtgg caggcgaggc tgcaggaggc  3994
ccacagataa gctggcaaga ggaaggatcc caggcacatg gttcatcacg agcatgaggg  4054
aacagcaagg ggcacggtat cacagcctgg agacacccac acagatggct ggatccggtg  4114
ctacgggaaa catttttccta agatgcccat gagaacagac caagatgtgt acagcactat  4174
gagcattaaa aaaccttcca gaatcaataa tccgtggcaa catatctctg taaaaacaaa  4234
cactgtaact tctaaataaa tgtttagtct tccctgtaac cttcaaaaaa aaaaaaaaa   4293
```

<210> SEQ ID NO 2
<211> LENGTH: 1114
<212> TYPE: PRT
<213> ORGANISM: Homo sapiens

<400> SEQUENCE: 2

```
Met Leu Arg Gly Thr Met Thr Ala Trp Arg Gly Met Arg Pro Glu Val
1               5                   10                  15

Thr Leu Ala Cys Leu Leu Leu Ala Thr Ala Gly Cys Phe Ala Asp Leu
            20                  25                  30

Asn Glu Val Pro Gln Val Thr Val Gln Pro Ala Ser Thr Val Gln Lys
        35                  40                  45

Pro Gly Gly Thr Val Ile Leu Gly Cys Val Val Glu Pro Pro Arg Met
    50                  55                  60

Asn Val Thr Trp Arg Leu Asn Gly Lys Glu Leu Asn Gly Ser Asp Asp
65                  70                  75                  80

Ala Leu Gly Val Leu Ile Thr His Gly Thr Leu Val Ile Thr Ala Leu
                85                  90                  95

Asn Asn His Thr Val Gly Arg Tyr Gln Cys Val Ala Arg Met Pro Ala
            100                 105                 110

Gly Ala Val Ala Ser Val Pro Ala Thr Val Thr Leu Ala Asn Leu Gln
        115                 120                 125

Asp Phe Lys Leu Asp Val Gln His Val Ile Glu Val Asp Glu Gly Asn
    130                 135                 140

Thr Ala Val Ile Ala Cys His Leu Pro Glu Ser His Pro Lys Ala Gln
145                 150                 155                 160

Val Arg Tyr Ser Val Lys Gln Glu Trp Leu Glu Ala Ser Arg Gly Asn
                165                 170                 175

Tyr Leu Ile Met Pro Ser Gly Asn Leu Gln Ile Val Asn Ala Ser Gln
            180                 185                 190
```

```
Glu Asp Glu Gly Met Tyr Lys Cys Ala Ala Tyr Asn Pro Val Thr Gln
            195                 200                 205
Glu Val Lys Thr Ser Gly Ser Ser Asp Arg Leu Arg Val Arg Arg Ser
    210                 215                 220
Thr Ala Glu Ala Ala Arg Ile Ile Tyr Pro Pro Glu Ala Gln Thr Ile
225                 230                 235                 240
Ile Val Thr Lys Gly Gln Ser Leu Ile Leu Glu Cys Val Ala Ser Gly
                245                 250                 255
Ile Pro Pro Pro Arg Val Thr Trp Ala Lys Asp Gly Ser Ser Val Thr
            260                 265                 270
Gly Tyr Asn Lys Thr Arg Phe Leu Leu Ser Asn Leu Leu Ile Asp Thr
    275                 280                 285
Thr Ser Glu Glu Asp Ser Gly Thr Tyr Arg Cys Met Ala Asp Asn Gly
290                 295                 300
Val Gly Gln Pro Gly Ala Ala Val Ile Leu Tyr Asn Val Gln Val Phe
305                 310                 315                 320
Glu Pro Pro Glu Val Thr Met Glu Leu Ser Gln Leu Val Ile Pro Trp
                325                 330                 335
Gly Gln Ser Ala Lys Leu Thr Cys Glu Val Arg Gly Asn Pro Pro Pro
            340                 345                 350
Ser Val Leu Trp Leu Arg Asn Ala Val Pro Leu Ile Ser Ser Gln Arg
    355                 360                 365
Leu Arg Leu Ser Arg Arg Ala Leu Arg Val Leu Ser Met Gly Pro Glu
    370                 375                 380
Asp Glu Gly Val Tyr Gln Cys Met Ala Glu Asn Glu Val Gly Ser Ala
385                 390                 395                 400
His Ala Val Val Gln Leu Arg Thr Ser Arg Pro Ser Ile Thr Pro Arg
                405                 410                 415
Leu Trp Gln Asp Ala Glu Leu Ala Thr Gly Thr Pro Pro Val Ser Pro
            420                 425                 430
Ser Lys Leu Gly Asn Pro Glu Gln Met Leu Arg Gly Gln Pro Ala Leu
    435                 440                 445
Pro Arg Pro Pro Thr Ser Val Gly Pro Ala Ser Pro Gln Cys Pro Gly
    450                 455                 460
Glu Lys Gly Gln Gly Ala Pro Ala Glu Ala Pro Ile Ile Leu Ser Ser
465                 470                 475                 480
Pro Arg Thr Ser Lys Thr Asp Ser Tyr Glu Leu Val Trp Arg Pro Arg
                485                 490                 495
His Glu Gly Ser Gly Arg Ala Pro Ile Leu Tyr Tyr Val Val Lys His
            500                 505                 510
Arg Lys Val Thr Asn Ser Ser Asp Asp Trp Thr Ile Ser Gly Ile Pro
    515                 520                 525
Ala Asn Gln His Arg Leu Thr Leu Thr Arg Leu Asp Pro Gly Ser Leu
    530                 535                 540
Tyr Glu Val Glu Met Ala Ala Tyr Asn Cys Ala Gly Glu Gly Gln Thr
545                 550                 555                 560
Ala Met Val Thr Phe Arg Thr Gly Arg Arg Pro Lys Pro Glu Ile Met
                565                 570                 575
Ala Ser Lys Glu Gln Gln Ile Gln Arg Asp Asp Pro Gly Ala Ser Pro
            580                 585                 590
Gln Ser Ser Ser Gln Pro Asp His Gly Arg Leu Ser Pro Pro Glu Ala
    595                 600                 605
Pro Asp Arg Pro Thr Ile Ser Thr Ala Ser Glu Thr Ser Val Tyr Val
610                 615                 620
```

```
Thr Trp Ile Pro Arg Gly Asn Gly Gly Phe Pro Ile Gln Ser Phe Arg
625                 630                 635                 640

Val Glu Tyr Lys Lys Leu Lys Val Gly Asp Trp Ile Leu Ala Thr
            645                 650                 655

Ser Ala Ile Pro Pro Ser Arg Leu Ser Val Glu Ile Thr Gly Leu Glu
                660                 665                 670

Lys Gly Thr Ser Tyr Lys Phe Arg Val Arg Ala Leu Asn Met Leu Gly
            675                 680                 685

Glu Ser Glu Pro Ser Ala Pro Ser Arg Pro Tyr Val Val Ser Gly Tyr
        690                 695                 700

Ser Gly Arg Val Tyr Glu Arg Pro Val Ala Gly Pro Tyr Ile Thr Phe
705                 710                 715                 720

Thr Asp Ala Val Asn Glu Thr Thr Ile Met Leu Lys Trp Met Tyr Ile
                725                 730                 735

Pro Ala Ser Asn Asn Asn Thr Pro Ile His Gly Phe Tyr Ile Tyr Tyr
                740                 745                 750

Arg Pro Thr Asp Ser Asp Asn Asp Ser Asp Tyr Lys Lys Asp Met Val
            755                 760                 765

Glu Gly Asp Lys Tyr Trp His Ser Ile Ser His Leu Gln Pro Glu Thr
        770                 775                 780

Ser Tyr Asp Ile Lys Met Gln Cys Phe Asn Glu Gly Gly Glu Ser Glu
785                 790                 795                 800

Phe Ser Asn Val Met Ile Cys Glu Thr Lys Ala Arg Lys Ser Ser Gly
                805                 810                 815

Gln Pro Gly Arg Leu Pro Pro Thr Leu Ala Pro Pro Gln Pro Pro
            820                 825                 830

Leu Pro Glu Thr Ile Glu Arg Pro Val Gly Thr Gly Ala Met Val Ala
        835                 840                 845

Arg Ser Ser Asp Leu Pro Tyr Leu Ile Val Gly Val Val Leu Gly Ser
850                 855                 860

Ile Val Leu Ile Ile Val Thr Phe Ile Pro Phe Cys Leu Trp Arg Ala
865                 870                 875                 880

Trp Ser Lys Gln Lys His Thr Thr Asp Leu Gly Phe Pro Arg Ser Ala
                885                 890                 895

Leu Pro Pro Ser Cys Pro Tyr Thr Met Val Pro Leu Gly Gly Leu Pro
                900                 905                 910

Gly His Gln Ala Ser Gly Gln Pro Tyr Leu Ser Gly Ile Ser Gly Arg
        915                 920                 925

Ala Cys Ala Asn Gly Ile His Met Asn Arg Gly Cys Pro Ser Ala Ala
930                 935                 940

Val Gly Tyr Pro Gly Met Lys Pro Gln Gln His Cys Pro Gly Glu Leu
945                 950                 955                 960

Gln Gln Gln Ser Asp Thr Ser Ser Leu Leu Arg Gln Thr His Leu Gly
            965                 970                 975

Asn Gly Tyr Asp Pro Gln Ser His Gln Ile Thr Arg Gly Pro Lys Ser
            980                 985                 990

Ser Pro Asp Glu Gly Ser Phe Leu Tyr Thr Leu Pro Asp Asp Ser Thr
        995                 1000                1005

His Gln Leu Leu Gln Pro His Asp Cys Cys Gln Arg Gln Glu
    1010                1015                1020

Gln Pro Ala Ala Val Gly Gln Ser Gly Val Arg Arg Ala Pro Asp
    1025                1030                1035

Ser Pro Val Leu Glu Ala Val Trp Asp Pro Pro Phe His Ser Gly
```

|  |  | 1040 |  |  | 1045 |  |  | 1050 |  |

Pro Pro Cys Cys Leu Gly Leu Val Pro Val Glu Glu Val Asp Ser
    1055                1060                1065

Pro Asp Ser Cys Gln Val Ser Gly Gly Asp Trp Cys Pro Gln His
    1070                1075                1080

Pro Val Gly Ala Tyr Val Gly Gln Glu Pro Gly Met Gln Leu Ser
    1085                1090                1095

Pro Gly Pro Leu Val Arg Val Ser Phe Glu Thr Pro Pro Leu Thr
    1100                1105                1110

Ile

<210> SEQ ID NO 3
<211> LENGTH: 1576
<212> TYPE: DNA
<213> ORGANISM: Homo sapiens
<220> FEATURE:
<221> NAME/KEY: CDS
<222> LOCATION: (152)..(1540)

<400> SEQUENCE: 3

```
gcgaggcagc cagcgaggga gagagcgagc gggcgagccg gagcgaggaa gggaaagcgc      60
aagagagagc gcacacgcac acacccgccg cgcgcactcg cgcacggacc cgcacgggga     120
cagctcggaa gtcatcagtt ccatgggcga g atg ctg ctg ctg gcg aga tgt       172
                                   Met Leu Leu Leu Ala Arg Cys
                                   1               5 ctg ctg cta gtc ctc gtc tcc tcg ctg ctg gta tgc tcg gga ctg gcg       220
Leu Leu Leu Val Leu Val Ser Ser Leu Leu Val Cys Ser Gly Leu Ala
        10                  15                  20 tgc gga ccg ggc agg ggg ttc ggg aag agg agg cac ccc aaa aag ctg       268
Cys Gly Pro Gly Arg Gly Phe Gly Lys Arg Arg His Pro Lys Lys Leu
25                  30                  35 acc cct tta gcc tac aag cag ttt atc ccc aat gtg gcc gag aag acc       316
Thr Pro Leu Ala Tyr Lys Gln Phe Ile Pro Asn Val Ala Glu Lys Thr
40                  45                  50                  55 cta ggc gcc agc gga agg tat gaa ggg aag atc tcc aga aac tcc gag       364
Leu Gly Ala Ser Gly Arg Tyr Glu Gly Lys Ile Ser Arg Asn Ser Glu
            60                  65                  70 cga ttt aag gaa ctc acc ccc aat tac aac ccc gac atc ata ttt aag       412
Arg Phe Lys Glu Leu Thr Pro Asn Tyr Asn Pro Asp Ile Ile Phe Lys
        75                  80                  85 gat gaa gaa aac acc gga gcg gac agg ctg atg act cag agg tgt aag       460
Asp Glu Glu Asn Thr Gly Ala Asp Arg Leu Met Thr Gln Arg Cys Lys
    90                  95                  100 gac aag ttg aac gct ttg gcc atc tcg gtg atg aac cag tgg cca gga       508
Asp Lys Leu Asn Ala Leu Ala Ile Ser Val Met Asn Gln Trp Pro Gly
105                 110                 115 gtg aaa ctg cgg gtg acc gag ggc tgg gac gaa gat ggc cac cac tca       556
Val Lys Leu Arg Val Thr Glu Gly Trp Asp Glu Asp Gly His His Ser
120                 125                 130                 135 gag gag tct ctg cac tac gag ggc cgc gca gtg gac atc acc acg tct       604
Glu Glu Ser Leu His Tyr Glu Gly Arg Ala Val Asp Ile Thr Thr Ser
            140                 145                 150 gac cgc gac cgc agc aag tac ggc atg ctg gcc cgc ctg gcg gtg gag       652
Asp Arg Asp Arg Ser Lys Tyr Gly Met Leu Ala Arg Leu Ala Val Glu
        155                 160                 165 gcc ggc ttc gac tgg gtg tac tac gag tcc aag gca cat atc cac tgc       700
Ala Gly Phe Asp Trp Val Tyr Tyr Glu Ser Lys Ala His Ile His Cys
    170                 175                 180 tcg gtg aaa gca gag aac tcg gtg gcg gcc aaa tcg gga ggc tgc ttc       748
```

| | | | | | | | | | | | | |
|---|---|---|---|---|---|---|---|---|---|---|---|---|
| Ser | Val | Lys | Ala | Glu | Asn | Ser | Val | Ala | Ala | Lys | Ser | Gly Gly Cys Phe |
| | 185 | | | | 190 | | | | 195 | | | |

| | | | | | | | | | | | | | | | | |
|---|---|---|---|---|---|---|---|---|---|---|---|---|---|---|---|---|
| ccg | ggc | tcg | gcc | acg | gtg | cac | ctg | gag | cag | ggc | ggc | acc | aag | ctg | gtg | 796 |
| Pro | Gly | Ser | Ala | Thr | Val | His | Leu | Glu | Gln | Gly | Gly | Thr | Lys | Leu | Val | |
| 200 | | | | | 205 | | | | | 210 | | | | | 215 | |

| | | | | | | | | | | | | | | | | |
|---|---|---|---|---|---|---|---|---|---|---|---|---|---|---|---|---|
| aag | gac | ctg | agc | ccc | ggg | gac | cgc | gtg | ctg | gcg | gcg | gac | gac | cag | ggc | 844 |
| Lys | Asp | Leu | Ser | Pro | Gly | Asp | Arg | Val | Leu | Ala | Ala | Asp | Asp | Gln | Gly | |
| | | | | 220 | | | | | 225 | | | | | 230 | | |

| | | | | | | | | | | | | | | | | |
|---|---|---|---|---|---|---|---|---|---|---|---|---|---|---|---|---|
| cgg | ctg | ctc | tac | agc | gac | ttc | ctc | act | ttc | ctg | gac | cgc | gac | gac | ggc | 892 |
| Arg | Leu | Leu | Tyr | Ser | Asp | Phe | Leu | Thr | Phe | Leu | Asp | Arg | Asp | Asp | Gly | |
| | | | | 235 | | | | | 240 | | | | | 245 | | |

| | | | | | | | | | | | | | | | | |
|---|---|---|---|---|---|---|---|---|---|---|---|---|---|---|---|---|
| gcc | aag | aag | gtc | ttc | tac | gtg | atc | gag | acg | cgg | gag | ccg | cgc | gag | cgc | 940 |
| Ala | Lys | Lys | Val | Phe | Tyr | Val | Ile | Glu | Thr | Arg | Glu | Pro | Arg | Glu | Arg | |
| | | | 250 | | | | | 255 | | | | | 260 | | | |

| | | | | | | | | | | | | | | | | |
|---|---|---|---|---|---|---|---|---|---|---|---|---|---|---|---|---|
| ctg | ctg | ctc | acc | gcc | gcg | cac | ctg | ctc | ttt | gtg | gcg | ccg | cac | aac | gac | 988 |
| Leu | Leu | Leu | Thr | Ala | Ala | His | Leu | Leu | Phe | Val | Ala | Pro | His | Asn | Asp | |
| 265 | | | | | 270 | | | | | 275 | | | | | | |

| | | | | | | | | | | | | | | | | |
|---|---|---|---|---|---|---|---|---|---|---|---|---|---|---|---|---|
| tcg | gcc | acc | ggg | gag | ccc | gag | gcg | tcc | tcg | ggc | tcg | ggg | ccg | cct | tcc | 1036 |
| Ser | Ala | Thr | Gly | Glu | Pro | Glu | Ala | Ser | Ser | Gly | Ser | Gly | Pro | Pro | Ser | |
| 280 | | | | | 285 | | | | | 290 | | | | | 295 | |

| | | | | | | | | | | | | | | | | |
|---|---|---|---|---|---|---|---|---|---|---|---|---|---|---|---|---|
| ggg | ggc | gca | ctg | ggg | cct | cgg | gcg | ctg | ttc | gcc | agc | cgc | gtg | cgc | ccg | 1084 |
| Gly | Gly | Ala | Leu | Gly | Pro | Arg | Ala | Leu | Phe | Ala | Ser | Arg | Val | Arg | Pro | |
| | | | | 300 | | | | | 305 | | | | | 310 | | |

| | | | | | | | | | | | | | | | | |
|---|---|---|---|---|---|---|---|---|---|---|---|---|---|---|---|---|
| ggc | cag | cgc | gtg | tac | gtg | gtg | gcc | gag | cgt | gac | ggg | gac | cgc | cgg | ctc | 1132 |
| Gly | Gln | Arg | Val | Tyr | Val | Val | Ala | Glu | Arg | Asp | Gly | Asp | Arg | Arg | Leu | |
| | | | | 315 | | | | | 320 | | | | | 325 | | |

| | | | | | | | | | | | | | | | | |
|---|---|---|---|---|---|---|---|---|---|---|---|---|---|---|---|---|
| ctg | ccc | gcc | gct | gtg | cac | agc | gtg | acc | cta | agc | gag | gag | gcc | gcg | ggc | 1180 |
| Leu | Pro | Ala | Ala | Val | His | Ser | Val | Thr | Leu | Ser | Glu | Glu | Ala | Ala | Gly | |
| | | | 330 | | | | | 335 | | | | | 340 | | | |

| | | | | | | | | | | | | | | | | |
|---|---|---|---|---|---|---|---|---|---|---|---|---|---|---|---|---|
| gcc | tac | gcg | ccg | ctc | acg | gcc | cag | ggc | acc | att | ctc | atc | aac | cgg | gtg | 1228 |
| Ala | Tyr | Ala | Pro | Leu | Thr | Ala | Gln | Gly | Thr | Ile | Leu | Ile | Asn | Arg | Val | |
| 345 | | | | | 350 | | | | | 355 | | | | | | |

| | | | | | | | | | | | | | | | | |
|---|---|---|---|---|---|---|---|---|---|---|---|---|---|---|---|---|
| ctg | gcc | tcg | tgc | tac | gcg | gtc | atc | gag | gag | cac | agc | tgg | gcg | cac | cgg | 1276 |
| Leu | Ala | Ser | Cys | Tyr | Ala | Val | Ile | Glu | Glu | His | Ser | Trp | Ala | His | Arg | |
| 360 | | | | | 365 | | | | | 370 | | | | | 375 | |

| | | | | | | | | | | | | | | | | |
|---|---|---|---|---|---|---|---|---|---|---|---|---|---|---|---|---|
| gcc | ttc | gcg | ccc | ttc | cgc | ctg | gcg | cac | gcg | ctc | ctg | gct | gca | ctg | gcg | 1324 |
| Ala | Phe | Ala | Pro | Phe | Arg | Leu | Ala | His | Ala | Leu | Leu | Ala | Ala | Leu | Ala | |
| | | | | 380 | | | | | 385 | | | | | 390 | | |

| | | | | | | | | | | | | | | | | |
|---|---|---|---|---|---|---|---|---|---|---|---|---|---|---|---|---|
| ccc | gcg | cgc | acg | gac | cgc | ggc | ggg | gac | agc | ggc | ggc | ggg | gac | cgc | ggg | 1372 |
| Pro | Ala | Arg | Thr | Asp | Arg | Gly | Gly | Asp | Ser | Gly | Gly | Gly | Asp | Arg | Gly | |
| | | | 395 | | | | | 400 | | | | | 405 | | | |

| | | | | | | | | | | | | | | | | |
|---|---|---|---|---|---|---|---|---|---|---|---|---|---|---|---|---|
| ggc | ggc | ggc | ggc | aga | gta | gcc | cta | acc | gct | cca | ggt | gct | gcc | gac | gct | 1420 |
| Gly | Gly | Gly | Gly | Arg | Val | Ala | Leu | Thr | Ala | Pro | Gly | Ala | Ala | Asp | Ala | |
| | | | 410 | | | | | 415 | | | | | 420 | | | |

| | | | | | | | | | | | | | | | | |
|---|---|---|---|---|---|---|---|---|---|---|---|---|---|---|---|---|
| ccg | ggt | gcg | ggg | gcc | acc | gcg | ggc | atc | cac | tgg | tac | tcg | cag | ctg | ctc | 1468 |
| Pro | Gly | Ala | Gly | Ala | Thr | Ala | Gly | Ile | His | Trp | Tyr | Ser | Gln | Leu | Leu | |
| 425 | | | | | 430 | | | | | 435 | | | | | | |

| | | | | | | | | | | | | | | | | |
|---|---|---|---|---|---|---|---|---|---|---|---|---|---|---|---|---|
| tac | caa | ata | ggc | acc | tgg | ctc | ctg | gac | agc | gag | gcc | ctg | cac | ccg | ctg | 1516 |
| Tyr | Gln | Ile | Gly | Thr | Trp | Leu | Leu | Asp | Ser | Glu | Ala | Leu | His | Pro | Leu | |
| 440 | | | | | 445 | | | | | 450 | | | | | 455 | |

| | | | | | | | | |
|---|---|---|---|---|---|---|---|---|
| ggc | atg | gcg | gtc | aag | tcc | agc | tga agccgggggg ccggggagg ggcgcgggag | 1570 |
| Gly | Met | Ala | Val | Lys | Ser | Ser | | |
| | | | | 460 | | | | |

| | |
|---|---|
| ggggcg | 1576 |

<210> SEQ ID NO 4
<211> LENGTH: 462
<212> TYPE: PRT
<213> ORGANISM: Homo sapiens

<400> SEQUENCE: 4

-continued

```
Met Leu Leu Leu Ala Arg Cys Leu Leu Val Leu Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
            115                 120                 125

Asp Glu Asp Gly His His Ser Glu Glu Ser Leu His Tyr Glu Gly Arg
130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
            195                 200                 205

Gln Gly Gly Thr Lys Leu Val Lys Asp Leu Ser Pro Gly Asp Arg Val
210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270

Phe Val Ala Pro His Asn Asp Ser Ala Thr Gly Glu Pro Glu Ala Ser
            275                 280                 285

Ser Gly Ser Gly Pro Pro Ser Gly Gly Ala Leu Gly Pro Arg Ala Leu
290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
            355                 360                 365

Glu His Ser Trp Ala His Arg Ala Phe Ala Pro Phe Arg Leu Ala His
            370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
```

-continued

```
                 420                 425                 430
His Trp Tyr Ser Gln Leu Leu Tyr Gln Ile Gly Thr Trp Leu Leu Asp
        435                 440                 445

Ser Glu Ala Leu His Pro Leu Gly Met Ala Val Lys Ser Ser
    450                 455                 460

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
cccatgagaa cagaccaaga t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
cccgtatact atggtgccat t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
cgacattaag atgcagtgct t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
gagggaaaca cagcagtcat t                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
cctctacaat gtccaggtgt t                                              21

<210> SEQ ID NO 10
<211> LENGTH: 3354
<212> TYPE: DNA
<213> ORGANISM: Mus musculus
<220> FEATURE:
<221> NAME/KEY: CDS
<222> LOCATION: (1)..(3354)

<400> SEQUENCE: 10 atg acg acg tgc cga aga gag cgg cct ata ctt aca ctg ctt tgg att     48
```

-continued

```
Met Thr Thr Cys Arg Arg Glu Arg Pro Ile Leu Thr Leu Leu Trp Ile
1               5                   10                  15 ctc atg gcc aca gca ggc tgc ctt gct gat ttg aat gag gtt cct cag    96
Leu Met Ala Thr Ala Gly Cys Leu Ala Asp Leu Asn Glu Val Pro Gln
        20                  25                  30 gtc aca gtc cag ccc atg tcc act gtc cag aag ctg gga gga act gtg   144
Val Thr Val Gln Pro Met Ser Thr Val Gln Lys Leu Gly Gly Thr Val
        35                  40                  45 atc ctg ggc tgt gtg gtg gag cca cca tgg atg aac gtg act tgg cgc   192
Ile Leu Gly Cys Val Val Glu Pro Pro Trp Met Asn Val Thr Trp Arg
50                  55                  60 ttc aac gga aag gag cta aat ggc tct gat gat gct ctg ggt gtc ttc   240
Phe Asn Gly Lys Glu Leu Asn Gly Ser Asp Asp Ala Leu Gly Val Phe
65                  70                  75                  80 atc acc cgt ggg acc ctt gtc att gct gcc ctc aac aac cac act gtg   288
Ile Thr Arg Gly Thr Leu Val Ile Ala Ala Leu Asn Asn His Thr Val
                85                  90                  95 gga cgg tac cag tgt gtg gca cgg atg cct gca gga gct gtg gcc agt   336
Gly Arg Tyr Gln Cys Val Ala Arg Met Pro Ala Gly Ala Val Ala Ser
            100                 105                 110 gtg cca gcc aca gtg acg cta gcc aat ctc cag gac ttt aaa tta gat   384
Val Pro Ala Thr Val Thr Leu Ala Asn Leu Gln Asp Phe Lys Leu Asp
        115                 120                 125 gtg cag cat gtg att gaa gta gac gag ggg aac aca gcc gtc att gcc   432
Val Gln His Val Ile Glu Val Asp Glu Gly Asn Thr Ala Val Ile Ala
    130                 135                 140 tgc cac ctg cct gag agc cac cca aaa gcc cag gtc cgg tac agt gtc   480
Cys His Leu Pro Glu Ser His Pro Lys Ala Gln Val Arg Tyr Ser Val
145                 150                 155                 160 aaa cag gag tgg ctg gag gcc tct aga gac aac tac ctg atc atg cca   528
Lys Gln Glu Trp Leu Glu Ala Ser Arg Asp Asn Tyr Leu Ile Met Pro
                165                 170                 175 tcc ggg aat ctc caa att gtc aat gcc agc caa gag gac gaa ggc atg   576
Ser Gly Asn Leu Gln Ile Val Asn Ala Ser Gln Glu Asp Glu Gly Met
            180                 185                 190 tac aag tgt gcc gcc tac aac ccg gtg acc cag gaa gtg aaa acc tcc   624
Tyr Lys Cys Ala Ala Tyr Asn Pro Val Thr Gln Glu Val Lys Thr Ser
        195                 200                 205 ggc tcc ggc gac agg ctg cgc gtg cgc cgg tcc act gct gag gct gcc   672
Gly Ser Gly Asp Arg Leu Arg Val Arg Arg Ser Thr Ala Glu Ala Ala
    210                 215                 220 cgc atc atc tac cca ctg gaa gcc cag acc gtc att gtc acc aaa ggc   720
Arg Ile Ile Tyr Pro Leu Glu Ala Gln Thr Val Ile Val Thr Lys Gly
225                 230                 235                 240 cag agt ctc ata ctg gag tgt gtg gcc agt gga atc cca cca cct cga   768
Gln Ser Leu Ile Leu Glu Cys Val Ala Ser Gly Ile Pro Pro Pro Arg
                245                 250                 255 gtc aca tgg gcc aag gat ggg tcc agc att gct gcc tat aac aag act   816
Val Thr Trp Ala Lys Asp Gly Ser Ser Ile Ala Ala Tyr Asn Lys Thr
            260                 265                 270 cgc ttc ctg ctg agt aat ttg ctt att gac acc acc agc gag gag gac   864
Arg Phe Leu Leu Ser Asn Leu Leu Ile Asp Thr Thr Ser Glu Glu Asp
        275                 280                 285 tca ggc acc tac cga tgt atg gcc agc aat ggg gtt ggg gat cct ggg   912
Ser Gly Thr Tyr Arg Cys Met Ala Ser Asn Gly Val Gly Asp Pro Gly
    290                 295                 300 gca gca gtc atc ctc tac aat gtc cag gtg ttc gaa ccc cct gag gtc   960
Ala Ala Val Ile Leu Tyr Asn Val Gln Val Phe Glu Pro Pro Glu Val
305                 310                 315                 320 acg gtg gag ctg tcc cag ctg gtc atc cca tgg ggc cag agt gca aag  1008
Thr Val Glu Leu Ser Gln Leu Val Ile Pro Trp Gly Gln Ser Ala Lys
```

-continued

```
          Thr Val Glu Leu Ser Gln Leu Val Ile Pro Trp Gly Gln Ser Ala Lys
                          325                 330                 335 ctc acc tgt gag gtt cga gga aac ccc cca ccc tct gta cta tgg ctg        1056
Leu Thr Cys Glu Val Arg Gly Asn Pro Pro Pro Ser Val Leu Trp Leu
                340                 345                 350 agg aat gca gtg ccc ctc acc tcc agc cag cgc ctc cgg ctg tca cgt        1104
Arg Asn Ala Val Pro Leu Thr Ser Ser Gln Arg Leu Arg Leu Ser Arg
            355                 360                 365 aga gcc ctg cgg gtg gtc agt gtt ggg cca gag gac gaa ggc gtg tac        1152
Arg Ala Leu Arg Val Val Ser Val Gly Pro Glu Asp Glu Gly Val Tyr
        370                 375                 380 cag tgc atg gct gag aat gcg gtt ggc agt gcc cac gct gtg gtc caa        1200
Gln Cys Met Ala Glu Asn Ala Val Gly Ser Ala His Ala Val Val Gln
385                 390                 395                 400 ctg agg acc gcc cgg cca gac aca acc ctg aga ccc ggg agg gat acc        1248
Leu Arg Thr Ala Arg Pro Asp Thr Thr Leu Arg Pro Gly Arg Asp Thr
                405                 410                 415 aag ccg att gct gcc aca ccc ccc atg cca ccc tcc aga ccc agc aga        1296
Lys Pro Ile Ala Ala Thr Pro Pro Met Pro Pro Ser Arg Pro Ser Arg
            420                 425                 430 cct gac cag atg ctt cgg gaa caa ccg ggg ctt gtt aag ccc cca acg        1344
Pro Asp Gln Met Leu Arg Glu Gln Pro Gly Leu Val Lys Pro Pro Thr
        435                 440                 445 tcg tcg gta cag cct act tcc ctg aag tgc ccg gga gaa gag cag gta        1392
Ser Ser Val Gln Pro Thr Ser Leu Lys Cys Pro Gly Glu Glu Gln Val
    450                 455                 460 gcc cct gca gag gca cct atc atc ctc agc tca ccc cgg acc tcc aag        1440
Ala Pro Ala Glu Ala Pro Ile Ile Leu Ser Ser Pro Arg Thr Ser Lys
465                 470                 475                 480 acg gac tcc tat gag ctg gtg tgg cgg cct cgc cat gag ggg agc agc        1488
Thr Asp Ser Tyr Glu Leu Val Trp Arg Pro Arg His Glu Gly Ser Ser
                485                 490                 495 cgg aca ccc atc ctg tac tac gta gtg aag cat cgt aag gtc acg aac        1536
Arg Thr Pro Ile Leu Tyr Tyr Val Val Lys His Arg Lys Val Thr Asn
            500                 505                 510 tcc tct gac gac tgg acc att tct ggc att cca gcc aac cag cac cgc        1584
Ser Ser Asp Asp Trp Thr Ile Ser Gly Ile Pro Ala Asn Gln His Arg
        515                 520                 525 ctc acc ctg acc agg ctt gac cct gga agc ttg tac gaa gtg gag atg        1632
Leu Thr Leu Thr Arg Leu Asp Pro Gly Ser Leu Tyr Glu Val Glu Met
    530                 535                 540 gca gcc tac aac tgt gct ggc gag ggc cag aca gct atg gtc acc ttc        1680
Ala Ala Tyr Asn Cys Ala Gly Glu Gly Gln Thr Ala Met Val Thr Phe
545                 550                 555                 560 cga aca gga cgg cgg ccc aaa cct gag atc gtg gcc agt aag gag cag        1728
Arg Thr Gly Arg Arg Pro Lys Pro Glu Ile Val Ala Ser Lys Glu Gln
                565                 570                 575 cag atc cag aga gat gac cct ggt gcc agt ctc cag agc agc agc cag        1776
Gln Ile Gln Arg Asp Asp Pro Gly Ala Ser Leu Gln Ser Ser Ser Gln
            580                 585                 590 cct gac cat ggc cgc ctc tcc ccc cca gaa gct cca gac aga ccc acc        1824
Pro Asp His Gly Arg Leu Ser Pro Pro Glu Ala Pro Asp Arg Pro Thr
        595                 600                 605 atc tcc aca gct tct gag acc tcc gtg tac gta acc tgg att ccc cga        1872
Ile Ser Thr Ala Ser Glu Thr Ser Val Tyr Val Thr Trp Ile Pro Arg
    610                 615                 620 ggg aac ggc ggc ttc ccg att cag tct ttc cgt gta gag tac aag aag        1920
Gly Asn Gly Gly Phe Pro Ile Gln Ser Phe Arg Val Glu Tyr Lys Lys
625                 630                 635                 640 cta aaa aaa gtg gga gat tgg ata ctg gct acc agt gcc ata cct ccc        1968
```

```
                Leu Lys Lys Val Gly Asp Trp Ile Leu Ala Thr Ser Ala Ile Pro Pro
                                645                 650                 655 tcg agg ctc tct gtg gag atc aca ggc cta gag aaa ggt att tct tac        2016
Ser Arg Leu Ser Val Glu Ile Thr Gly Leu Glu Lys Gly Ile Ser Tyr
            660                 665                 670 aag ttc cga gtt cgt gct ttg aac atg tta ggg gag agt gag ccc agt        2064
Lys Phe Arg Val Arg Ala Leu Asn Met Leu Gly Glu Ser Glu Pro Ser
        675                 680                 685 gct ccc tcc cgg ccc tac gtg gtg tca ggc tac agt ggc cgt gta tat        2112
Ala Pro Ser Arg Pro Tyr Val Val Ser Gly Tyr Ser Gly Arg Val Tyr
    690                 695                 700 gag agg ccc gtg gca gga cct tac atc acc ttc act gat gca gtc aat        2160
Glu Arg Pro Val Ala Gly Pro Tyr Ile Thr Phe Thr Asp Ala Val Asn
705                 710                 715                 720 gag acc act att atg ctc aag tgg atg tat atc cca gcc agt aac aac        2208
Glu Thr Thr Ile Met Leu Lys Trp Met Tyr Ile Pro Ala Ser Asn Asn
                725                 730                 735 aac acc cca atc cat ggc ttc tat atc tac tac cga ccc aca gac agt        2256
Asn Thr Pro Ile His Gly Phe Tyr Ile Tyr Tyr Arg Pro Thr Asp Ser
            740                 745                 750 gac aat gac agt gac tac aag aag gac atg gta gaa ggg gac agg tac        2304
Asp Asn Asp Ser Asp Tyr Lys Lys Asp Met Val Glu Gly Asp Arg Tyr
        755                 760                 765 tgg cac tcc atc agc cac ctg cag cca gag act tcc tat gac att aaa        2352
Trp His Ser Ile Ser His Leu Gln Pro Glu Thr Ser Tyr Asp Ile Lys
    770                 775                 780 atg cag tgc ttc aat gaa gga ggg gag agc gag ttc agc aat gtc atg        2400
Met Gln Cys Phe Asn Glu Gly Gly Glu Ser Glu Phe Ser Asn Val Met
785                 790                 795                 800 atc tgc gag acc aaa gct cgg aaa ttt tct ggt cag cct gga aga ccc        2448
Ile Cys Glu Thr Lys Ala Arg Lys Phe Ser Gly Gln Pro Gly Arg Pro
                805                 810                 815 cca ccc ttg act cta gct cca cca cag cct ccg ccc cta gaa acc atg        2496
Pro Pro Leu Thr Leu Ala Pro Pro Gln Pro Pro Pro Leu Glu Thr Met
            820                 825                 830 gaa cgg ccg gtg ggc act gga gcc atg gtg gca cgg gcc agc gac ctg        2544
Glu Arg Pro Val Gly Thr Gly Ala Met Val Ala Arg Ala Ser Asp Leu
        835                 840                 845 ccc tat ctg att gtc ggg gtt gtt ctg ggc tct ata gtc ctc atc atc        2592
Pro Tyr Leu Ile Val Gly Val Val Leu Gly Ser Ile Val Leu Ile Ile
    850                 855                 860 gtc acc ttc atc ccc ttc tgc cta tgg agg gcc tgg tct aag cag aaa        2640
Val Thr Phe Ile Pro Phe Cys Leu Trp Arg Ala Trp Ser Lys Gln Lys
865                 870                 875                 880 cac aca aca gat ctg ggt ttt cct cgg agt gcc ctc ctg tct tct tcg        2688
His Thr Thr Asp Leu Gly Phe Pro Arg Ser Ala Leu Leu Ser Ser Ser
                885                 890                 895 tgc cag tac aca atg gtg cca ttg gag gga ctt cca ggt cac caa gcc        2736
Cys Gln Tyr Thr Met Val Pro Leu Glu Gly Leu Pro Gly His Gln Ala
            900                 905                 910 aac ggg cag ccc tac ctt ggt ggc gtc agt gga cgg gcc tgt gtc agt        2784
Asn Gly Gln Pro Tyr Leu Gly Gly Val Ser Gly Arg Ala Cys Val Ser
        915                 920                 925 cga gtg cac gga agc agg ggc tgc cct gct gct aca gtg ggc tgt cca        2832
Arg Val His Gly Ser Arg Gly Cys Pro Ala Ala Thr Val Gly Cys Pro
    930                 935                 940 ggc agg aag cct cag cag cac tgc cca ggg gag ctt gcc cag cgg gaa        2880
Gly Arg Lys Pro Gln Gln His Cys Pro Gly Glu Leu Ala Gln Arg Glu
945                 950                 955                 960 gac acc aac agc caa ctg agg cag ccc att gtt agc aac gga tat gac        2928
```

```
Asp Thr Asn Ser Gln Leu Arg Gln Pro Ile Val Ser Asn Gly Tyr Asp
            965                 970                 975 ctc cag aac cag cag gtt gcc aga ggt ccc cag tgt gcc tca gga gta       2976
Leu Gln Asn Gln Gln Val Ala Arg Gly Pro Gln Cys Ala Ser Gly Val
            980                 985                 990 gga gct ttc tta tac acg ctg cct gat gac tca act cac cag ctg ctc       3024
Gly Ala Phe Leu Tyr Thr Leu Pro Asp Asp Ser Thr His Gln Leu Leu
            995                 1000                1005 caa cct caa gac tgc tgt cac ctc cag aag caa ccc gtc acc aca           3069
Gln Pro Gln Asp Cys Cys His Leu Gln Lys Gln Pro Val Thr Thr
        1010                1015                1020 tgc caa aca gca gtg agg cga acg tct gaa agt cct gga cta gaa           3114
Cys Gln Thr Ala Val Arg Arg Thr Ser Glu Ser Pro Gly Leu Glu
        1025                1030                1035 tct tca tgg gac cct cca tat cat tca ggg ccc cag tgc tgt tta           3159
Ser Ser Trp Asp Pro Pro Tyr His Ser Gly Pro Gln Cys Cys Leu
        1040                1045                1050 ggt ctt gta cca gtt gaa gaa gta gac agt tct gac tcc tgc caa           3204
Gly Leu Val Pro Val Glu Glu Val Asp Ser Ser Asp Ser Cys Gln
        1055                1060                1065 gtg ggt gga gga gac tgg agt tcc cag cat cca tca ggg acc tac           3249
Val Gly Gly Gly Asp Trp Ser Ser Gln His Pro Ser Gly Thr Tyr
        1070                1075                1080 aca gga cag gaa cgt ggg atg cgg ttc tcg cct agc cca tca gtt           3294
Thr Gly Gln Glu Arg Gly Met Arg Phe Ser Pro Ser Pro Ser Val
        1085                1090                1095 cat gtg tcc ttt gaa aca cca cct ccc aca att gga ccg gtc gcc           3339
His Val Ser Phe Glu Thr Pro Pro Pro Thr Ile Gly Pro Val Ala
        1100                1105                1110 acc atg gtg agc tag                                                   3354
Thr Met Val Ser
        1115

<210> SEQ ID NO 11
<211> LENGTH: 1117
<212> TYPE: PRT
<213> ORGANISM: Mus musculus

<400> SEQUENCE: 11

Met Thr Thr Cys Arg Arg Glu Arg Pro Ile Leu Thr Leu Leu Trp Ile
1               5                   10                  15

Leu Met Ala Thr Ala Gly Cys Leu Ala Asp Leu Asn Glu Val Pro Gln
                20                  25                  30

Val Thr Val Gln Pro Met Ser Thr Val Gln Lys Leu Gly Gly Thr Val
            35                  40                  45

Ile Leu Gly Cys Val Val Glu Pro Pro Trp Met Asn Val Thr Trp Arg
        50                  55                  60

Phe Asn Gly Lys Glu Leu Asn Gly Ser Asp Asp Ala Leu Gly Val Phe
65                  70                  75                  80

Ile Thr Arg Gly Thr Leu Val Ile Ala Ala Leu Asn Asn His Thr Val
                85                  90                  95

Gly Arg Tyr Gln Cys Val Ala Arg Met Pro Ala Gly Ala Val Ala Ser
                100                 105                 110

Val Pro Ala Thr Val Thr Leu Ala Asn Leu Gln Asp Phe Lys Leu Asp
            115                 120                 125

Val Gln His Val Ile Glu Val Asp Glu Gly Asn Thr Ala Val Ile Ala
        130                 135                 140

Cys His Leu Pro Glu Ser His Pro Lys Ala Gln Val Arg Tyr Ser Val
145                 150                 155                 160
```

```
Lys Gln Glu Trp Leu Glu Ala Ser Arg Asp Asn Tyr Leu Ile Met Pro
                165                 170                 175
Ser Gly Asn Leu Gln Ile Val Asn Ala Ser Gln Glu Asp Glu Gly Met
            180                 185                 190
Tyr Lys Cys Ala Ala Tyr Asn Pro Val Thr Gln Glu Val Lys Thr Ser
        195                 200                 205
Gly Ser Gly Asp Arg Leu Arg Val Arg Arg Ser Thr Ala Glu Ala Ala
    210                 215                 220
Arg Ile Ile Tyr Pro Leu Glu Ala Gln Thr Val Ile Val Thr Lys Gly
225                 230                 235                 240
Gln Ser Leu Ile Leu Glu Cys Val Ala Ser Gly Ile Pro Pro Pro Arg
                245                 250                 255
Val Thr Trp Ala Lys Asp Gly Ser Ser Ile Ala Ala Tyr Asn Lys Thr
            260                 265                 270
Arg Phe Leu Leu Ser Asn Leu Leu Ile Asp Thr Thr Ser Glu Glu Asp
        275                 280                 285
Ser Gly Thr Tyr Arg Cys Met Ala Ser Asn Gly Val Gly Asp Pro Gly
    290                 295                 300
Ala Ala Val Ile Leu Tyr Asn Val Gln Val Phe Glu Pro Pro Glu Val
305                 310                 315                 320
Thr Val Glu Leu Ser Gln Leu Val Ile Pro Trp Gly Gln Ser Ala Lys
                325                 330                 335
Leu Thr Cys Glu Val Arg Gly Asn Pro Pro Pro Ser Val Leu Trp Leu
            340                 345                 350
Arg Asn Ala Val Pro Leu Thr Ser Ser Gln Arg Leu Arg Leu Ser Arg
        355                 360                 365
Arg Ala Leu Arg Val Val Ser Val Gly Pro Glu Asp Glu Gly Val Tyr
    370                 375                 380
Gln Cys Met Ala Glu Asn Ala Val Gly Ser His Ala Val Val Gln
385                 390                 395                 400
Leu Arg Thr Ala Arg Pro Asp Thr Thr Leu Arg Pro Gly Arg Asp Thr
                405                 410                 415
Lys Pro Ile Ala Ala Thr Pro Pro Met Pro Pro Ser Arg Pro Ser Arg
            420                 425                 430
Pro Asp Gln Met Leu Arg Glu Gln Pro Gly Leu Val Lys Pro Pro Thr
        435                 440                 445
Ser Ser Val Gln Pro Thr Ser Leu Lys Cys Pro Gly Glu Glu Gln Val
    450                 455                 460
Ala Pro Ala Glu Ala Pro Ile Ile Leu Ser Ser Pro Arg Thr Ser Lys
465                 470                 475                 480
Thr Asp Ser Tyr Glu Leu Val Trp Arg Pro Arg His Glu Gly Ser Ser
                485                 490                 495
Arg Thr Pro Ile Leu Tyr Tyr Val Val Lys His Arg Lys Val Thr Asn
            500                 505                 510
Ser Ser Asp Asp Trp Thr Ile Ser Gly Ile Pro Ala Asn Gln His Arg
        515                 520                 525
Leu Thr Leu Thr Arg Leu Asp Pro Gly Ser Leu Tyr Glu Val Glu Met
    530                 535                 540
Ala Ala Tyr Asn Cys Ala Gly Glu Gly Gln Thr Ala Met Val Thr Phe
545                 550                 555                 560
Arg Thr Gly Arg Arg Pro Lys Pro Glu Ile Val Ala Ser Lys Glu Gln
                565                 570                 575
Gln Ile Gln Arg Asp Asp Pro Gly Ala Ser Leu Gln Ser Ser Ser Gln
```

-continued

```
                580               585                 590
Pro Asp His Gly Arg Leu Ser Pro Pro Glu Ala Pro Asp Arg Pro Thr
            595                 600                 605
Ile Ser Thr Ala Ser Glu Thr Ser Val Tyr Val Thr Trp Ile Pro Arg
610                 615                 620
Gly Asn Gly Gly Phe Pro Ile Gln Ser Phe Arg Val Glu Tyr Lys Lys
625                 630                 635                 640
Leu Lys Lys Val Gly Asp Trp Ile Leu Ala Thr Ser Ala Ile Pro Pro
                645                 650                 655
Ser Arg Leu Ser Val Glu Ile Thr Gly Leu Glu Lys Gly Ile Ser Tyr
            660                 665                 670
Lys Phe Arg Val Arg Ala Leu Asn Met Leu Gly Glu Ser Glu Pro Ser
            675                 680                 685
Ala Pro Ser Arg Pro Tyr Val Val Ser Gly Tyr Ser Gly Arg Val Tyr
            690                 695                 700
Glu Arg Pro Val Ala Gly Pro Tyr Ile Thr Phe Thr Asp Ala Val Asn
705                 710                 715                 720
Glu Thr Thr Ile Met Leu Lys Trp Met Tyr Ile Pro Ala Ser Asn Asn
                725                 730                 735
Asn Thr Pro Ile His Gly Phe Tyr Ile Tyr Tyr Arg Pro Thr Asp Ser
                740                 745                 750
Asp Asn Asp Ser Asp Tyr Lys Lys Asp Met Val Glu Gly Asp Arg Tyr
            755                 760                 765
Trp His Ser Ile Ser His Leu Gln Pro Glu Thr Ser Tyr Asp Ile Lys
            770                 775                 780
Met Gln Cys Phe Asn Glu Gly Gly Glu Ser Glu Phe Ser Asn Val Met
785                 790                 795                 800
Ile Cys Glu Thr Lys Ala Arg Lys Phe Ser Gln Pro Gly Arg Pro
                805                 810                 815
Pro Pro Leu Thr Leu Ala Pro Pro Gln Pro Pro Leu Glu Thr Met
                820                 825                 830
Glu Arg Pro Val Gly Thr Gly Ala Met Val Ala Arg Ala Ser Asp Leu
            835                 840                 845
Pro Tyr Leu Ile Val Gly Val Val Leu Gly Ser Ile Val Leu Ile Ile
            850                 855                 860
Val Thr Phe Ile Pro Phe Cys Leu Trp Arg Ala Trp Ser Lys Gln Lys
865                 870                 875                 880
His Thr Thr Asp Leu Gly Phe Pro Arg Ser Ala Leu Leu Ser Ser Ser
                885                 890                 895
Cys Gln Tyr Thr Met Val Pro Leu Glu Gly Leu Pro Gly His Gln Ala
                900                 905                 910
Asn Gly Gln Pro Tyr Leu Gly Val Ser Gly Arg Ala Cys Val Ser
            915                 920                 925
Arg Val His Gly Ser Arg Gly Cys Pro Ala Ala Thr Val Gly Cys Pro
            930                 935                 940
Gly Arg Lys Pro Gln Gln His Cys Pro Gly Glu Leu Ala Gln Arg Glu
945                 950                 955                 960
Asp Thr Asn Ser Gln Leu Arg Gln Pro Ile Val Ser Asn Gly Tyr Asp
                965                 970                 975
Leu Gln Asn Gln Gln Val Ala Arg Gly Pro Gln Cys Ala Ser Gly Val
            980                 985                 990
Gly Ala Phe Leu Tyr Thr Leu Pro  Asp Asp Ser Thr His Gln Leu Leu
            995                 1000                1005
```

```
Gln Pro Gln Asp Cys Cys His Leu Gln Lys Gln Pro Val Thr Thr
    1010                1015                1020

Cys Gln Thr Ala Val Arg Arg Thr Ser Glu Ser Pro Gly Leu Glu
    1025                1030                1035

Ser Ser Trp Asp Pro Pro Tyr His Ser Gly Pro Gln Cys Cys Leu
    1040                1045                1050

Gly Leu Val Pro Val Glu Glu Val Asp Ser Ser Asp Ser Cys Gln
    1055                1060                1065

Val Gly Gly Gly Asp Trp Ser Ser Gln His Pro Ser Gly Thr Tyr
    1070                1075                1080

Thr Gly Gln Glu Arg Gly Met Arg Phe Ser Pro Ser Pro Ser Val
    1085                1090                1095

His Val Ser Phe Glu Thr Pro Pro Pro Thr Ile Gly Pro Val Ala
    1100                1105                1110

Thr Met Val Ser
    1115

<210> SEQ ID NO 12
<211> LENGTH: 8
<212> TYPE: PRT
<213> ORGANISM: Artificial Sequence
<220> FEATURE:
<223> OTHER INFORMATION: Tag

<400> SEQUENCE: 12

Gly Pro Val Ala Thr Met Val Ser
1               5

<210> SEQ ID NO 13
<211> LENGTH: 24
<212> TYPE: DNA
<213> ORGANISM: Artificial Sequence
<220> FEATURE:
<223> OTHER INFORMATION: Tag

<400> SEQUENCE: 13
ggaccggtcg ccaccatggt gagc                                          24

<210> SEQ ID NO 14
<211> LENGTH: 10
<212> TYPE: DNA
<213> ORGANISM: Artificial Sequence
<220> FEATURE:
<223> OTHER INFORMATION: Synthetic oligonucleotide

<400> SEQUENCE: 14
agaacagacc                                                          10

<210> SEQ ID NO 15
<211> LENGTH: 18
<212> TYPE: PRT
<213> ORGANISM: Artificial Sequence
<220> FEATURE:
<223> OTHER INFORMATION: Synthetic peptide

<400> SEQUENCE: 15

Arg Arg Thr Ser Glu Ser Pro Gly Leu Glu Ser Ser Trp Asp Pro Pro
1               5                   10                  15

Tyr His
```

HEDGEHOG PATHWAY MODULATION AND USES THEREOF FOR TREATING, PREVENTING AND/OR DIAGNOSING CANCER

CROSS REFERENCE TO RELATED APPLICATIONS

This application claims the benefit, under 35 U.S.C. 119 (e), of U.S. Provisional Patent Application Ser. No. 61/095,155 filed on Sep. 8, 2008, which is incorporated herein by reference in its entirety.

FIELD OF THE INVENTION

The present invention generally relates to cancer, and more particularly to methods for the prevention, treatment, diagnostic and prognostic of invasive diseases, such as medulloblastoma.

SEQUENCE LISTING

This application contains a Sequence Listing in computer readable form entitled [12810_267-seq listing_ST25.txt], created Sep. 3, 2009 having a size of 65 Ko. The computer readable form is incorporated herein by reference.

BACKGROUND OF THE INVENTION

Neoplastic Diseases

The transformation of a normal cell into a malignant cell results, among other things, in the uncontrolled proliferation of the progeny cells, which exhibit immature, undifferentiated morphology, exaggerated survival and proangiogenic properties. It is also often associated with overexpression or constitutive activation of oncogenes not normally expressed by normal mature cells. Once a tumor has formed, cancer cells can leave the original tumor site and migrate to other parts of the body via the bloodstream and/or the lymphatic system by a process called metastasis. In this way, the disease may spread from one organ or part to another non-contiguous organ or part.

The increased number of cancer cases reported around the world is a major concern. Currently there are only a handful of treatments available for specific types of cancer and these treatments provide only limited efficacy. In order to be most effective, these treatments require: early detection of the malignancy, reliable assessment of its severity, methods of tracking possible metastasis, and readouts to monitor patients' response to treatment.

The Hedgehog Pathway

The seven transmembrane domain containing protein smoothened (SMO) serves as the key player for signal transduction of the Hedgehog (Hh) pathway. There are 3 Hh-related genes in vertebrates: sonic hedgehog (Shh), Indian Hedgehog and Desert Hedgehog. Hh is used here to encompass all three genes. However, the pathway's function is inhibited by a Hh-binding twelve transmembrane domain protein, patched (PTC), in the absence of Hh ligands. There are two homologs of patched in vertebrates (e.g., Ptch1 and Ptch2 in mouse, PTCH1 and PTCH2 in human), and one gene in Drosophila. As used herein, "Ptc" is used to designate the human gene or the mouse gene. The context specifies which species was used. It has recently been shown that the type I transmembrane proteins CDON (cell-adhesion-molecule-related/downregulated by oncogenes) and BOC (biregional CDON-binding protein; also known as "brother of CDON") are also able to bind Hh (Okada, A et al., Nature 444 (7117): 369-373). In the presence of active Hh ligands, it is thought that binding of Hh to PTC and BOC/CDON complexes releases their inhibition of SMO, allowing SMO to signal downstream to Gli/Ci transcription factors. As transcription factors, Gli molecules can regulate the expression of Hh target genes by directly associating with a specific consensus sequence located in the promoter region of the target genes such as GLI1 itself, PTCH1 and HIP (McMahon, A P et al., Curr Top Dev Biol 2003, 53: 1-114). FIG. 1 shows a simplified diagram of Hh signaling in the presence of Hh. Hh proteins (sonic hedgehog (Shh), Indian hedgehog (Ihh) (not shown) and desert hedgehog (Dhh) (not shown)) are secreted molecules, functioning both on nearby and distant cells in developing tissues. Following translation, Hh proteins enter the secretory pathway and undergo autoprocessing and other post-translational modifications. Binding of Hh to PTC1 alone, in the absence of interaction with BOC/CDON complexes, results in lower levels of hedgehog pathway activation. Interaction of Hh with both PTC and BOC/CDON complexes results in increased hedgehog pathway activation. Other major components includes Su(Fu), REN, Costal2, Fused and recently Gas1. The C-terminal tails of BOC/CDON might convey other signals to cytoskeletal or integral membrane proteins that induce morphological changes in the cell and signal to the nucleus through unknown mechanisms.

CDON and BOC are type I transmembrane receptors consisting of four or five immunoglobulin (Ig) and two or three fibronectin type III (FNIII) repeats in the extracellular domain, and an intracellular domain with no identifiable motifs. This domain architecture is closely related to that of axon guidance receptors of the Robo and DCC (deleted in colorectal cancer) families (FIG. 2). Both CDON and BOC share a high degree of homology in their extracellular domains and are expressed during early stages of development of the central nervous system (Okada et al., 2006. Nature, 444: 369-373). CDON and BOC form complexes with each other in a cis fashion.

Cerebellum Development and Medulloblastoma

During cerebellum development, Granule Cell Precursors (GCP) undergo rapid proliferation in the External Germinal Layer (EGL) of the cerebellum. Expansion of the GCP is dependent of Sonic hedgehog secreted by Purkinje cells. After their final division, GCP differentiate into Granule cells (GC) and migrate through the Purkinje cell layer to form mature granule cells that reside in the internal granule cell layer (IGL).

Medulloblastoma is an embryonal neuroepithelial tumor of the cerebellum and the most common malignant brain tumor occurring in children (Reviewed in Rossi et al. 2008. Clin. Cancer. Res, 14: 971-976). The tumors develop in the cerebellum, in a part of the brain called the posterior fossa, but may spread to other parts of the brain including the spinal cord. Medulloblastomas may also spread to other parts of the body often through the cerebrospinal fluid (CSF), which surrounds and protects the brain and spinal cord.

It is common knowledge that a clinical diagnosis of medulloblastoma is based on a combination of symptoms and signs observed in the evolution of the disease in the patient. An earlier diagnosis, particularly during neurosurgical clinical examination, would greatly increase the chances of successful treatment and recovery. Currently, proper diagnosis of medulloblastoma involves an invasive procedure whereby a biopsy is performed and sample cells are removed from the tumour and subsequently analyzed. In addition, CSF can be examined for the presence of tumor cells to determine if the tumor has metastasized, which is usually a very poor prognostic (Reviewed in Rossi et al. 2008, supra).

Despite improved multimodal treatment regimens, approximately one-third of patients with medulloblastoma remain incurable and current treatments significantly damage long-term survivors. Although fewer than 500 children per year in the US are diagnosed with medulloblastoma, the outcome is almost invariably poor. Surgery with subsequent radiation or chemotherapy has increased survival to greater than 50%, but the current methods of treatment result in severe long-term side effects including mental retardation.

Medulloblastoma can be a very aggressive tumor. The treatment of Medulloblastoma consists of surgery to remove as much tumor mass as possible, followed by radiotherapy, sometimes also combined with chemotherapy. In spite of these very aggressive treatments, only about 50 to 70% of patients survive after 5 years. For the survivors, the intense radiotherapy often leads to severe side effects, such as permanent cognitive impairment. However, not all MB are equally aggressive and information which informs prognosis, such as risk-assessment by the presence or absence of a molecular marker, would be useful to help determine which type of treatment (less or more aggressive) is most appropriate for each patient.

After surgery and radiotherapy, Medulloblastoma patients are closely followed by MRI for potential relapse of the tumor. This is particularly important in patients in which total resection of the tumor was impossible, which constitute 30-40% of the total number of patients undergoing surgery. Here, having a rapid, simple and robust method to detect tumor relapse at early stages would be very useful.

In some cases, tumor cells might disseminate in the CSF and metastasize to the spinal cord and other parts of the brain. This is one of the most feared complications of MB. The sensitive detection of MB disseminating cells in the CSF or the detection of metastases at early stage would certainly improve treatment outcome.

To improve the outcome of those medulloblastoma patients with high-risk disease as well as the quality of life of all survivors following treatment, both novel therapies and improved tumor classification are required. Novel therapies will result from a greater understanding of the disease process and are likely to involve small molecules designed to target specific pathways, including hedgehog, that become dysregulated during oncogenesis. An improved tumor classification will incorporate an assessment of the molecular profiles of medulloblastomas with defined biological behaviors or of the status of cellular pathways that are potential targets for novel therapies.

Thus, there is a need for the identification of novel targets that could serve as biomarkers of early stages of cancer. There is a need for the identification of novel biomarkers for better characterization and classification of tumors. Also, there is a need for improved diagnostic and prognostic detection methods as well as novel anti-cancer treatments which can be administered to subjects either suffering from or who are at a high risk of developing cancer to prevent, inhibit or treat the disease and the spread thereof.

The present description refers to a number of documents, the content of which is herein incorporated by reference in their entirety.

SUMMARY OF THE INVENTION

The present inventors show herein that BOC deficiency is associated with lower proliferation of cerebellum cells, and that overexpression of BOC in these cells results in increased proliferation. They demonstrate that BOC is expressed/overexpressed in various tumors, including medulloblastoma tumors, and that mice having an homozygous deletion of the BOC gene ($BOC^{-/-}$ mice) show increased survival as compared to their heterozygous counterparts ($BOC^{+/-}$ mice) in a medulloblastoma mouse model. They also show that BOC expression can be correlated with poor or good outcome. Therefore, BOC may constitute a tumor marker for diagnosis applications, and agents that inhibit or decrease the expression and/or activity of BOC (BOC inhibitors) may be useful for inhibiting the growth of tumor cells and for the treatment of cancers such as medulloblastoma.

Accordingly, in an aspect, the present invention provides a method for preventing and/or treating cancer comprising administering to a subject in need thereof an effective amount of an inhibitor of biregional cell adhesion molecule-related/down-regulated by oncogenes (CDON) binding protein (BOC).

In another aspect, the present invention provides a use of a BOC inhibitor for preventing and/or treating cancer in a subject.

In another aspect, the present invention provides a use of a BOC inhibitor for the preparation of a medicament for preventing and/or treating cancer in a subject.

In another aspect, the present invention provides a BOC inhibitor for preventing and/or treating cancer.

In another aspect, the present invention provides a composition for preventing and/or treating cancer comprising a BOC inhibitor, and a pharmaceutically acceptable carrier.

In another aspect, the present invention provides a method for determining whether a test compound is useful for the prevention and/or treatment of cancer, said method comprising: contacting said test compound with a BOC polypeptide, or a fragment thereof or variant thereof having BOC activity; and determining whether the activity of the BOC polypeptide, fragment or variant thereof, is decreased in the presence of said test compound, wherein a decrease in the activity of said BOC polypeptide, or a fragment thereof, in the presence of said test compound is indicative that said test compound may be used for the prevention and/or treatment of cancer.

In another aspect, the present invention provides a method for determining whether a test compound is useful for the prevention and/or treatment of cancer, said method comprising: contacting said test compound with a cell expressing BOC; and determining whether the expression and/or activity of BOC is decreased in the presence of said test compound, wherein said decrease in the expression and/or activity of BOC in the presence of said test compound is indicative that said test compound may be used for the prevention and/or treatment of cancer.

In another aspect, the present invention provides a method for determining whether a test compound is useful for the prevention and/or treatment of cancer, said method comprising: contacting said test compound with a cell comprising a first nucleic acid comprising a transcriptionally regulatory element normally associated with a BOC gene, operably linked to a second nucleic acid comprising a reporter gene encoding a reporter protein; and determining whether the reporter gene expression and/or reporter protein activity is decreased in the presence of said test compound; wherein said decrease in reporter gene expression and/or reporter protein activity is indicative that said test compound may be used for prevention and/or treatment of cancer.

In another aspect, the present invention provides a method for determining whether a test compound is useful for the prevention and/or treatment of cancer, said method comprising: contacting said test compound with a cell comprising a first nucleic acid comprising a transcriptionally regulatory element normally associated with a gene whose expression is increased by BOC activity, operably linked to a second nucleic acid comprising a reporter gene encoding a reporter protein; and determining whether the reporter gene expression and/or reporter protein activity is decreased in the presence of said test compound; wherein said decrease in reporter gene expression and/or reporter protein activity is indicative that said test compound may be used for prevention and/or treatment of cancer.

In an embodiment, the above-mentioned gene whose expression is increased by BOC activity is glioma-associated oncogene homolog 1 (GLI-1).

In another aspect, the present invention provides a method for diagnosing a cancer or a predisposition to cancer in a first subject comprising: determining the expression and/or activity of BOC in a sample from said first subject; comparing said expression and/or activity to a corresponding reference expression and/or activity; and diagnosing said cancer or predisposition to cancer based on said comparison.

In an embodiment, the above-mentioned reference expression and/or activity corresponds to an expression and/or activity determined in a sample from a control subject known to not being predisposed to cancer and to not have cancer, and wherein a higher expression and/or activity in said sample from said first subject is indicative that said first subject has cancer or a predisposition to cancer.

In another embodiment, the above-mentioned reference expression and/or activity corresponds to an expression and/or activity determined in a sample from a control subject known to have a predisposition to cancer, and wherein a comparable or higher expression and/or activity in said sample from said first subject is indicative that said first subject has cancer or a predisposition to cancer.

In another aspect, the present invention provides a method for inhibiting the proliferation and/or differentiation of a cell having an active hedgehog pathway comprising contacting said cell with a BOC inhibitor.

In another aspect, the present invention provides a use of a BOC inhibitor for inhibiting the proliferation and/or differentiation of a cell having an active hedgehog pathway.

In another aspect, the present invention provides a use of a BOC inhibitor for the preparation of a medicament for inhibiting the proliferation and/or differentiation of a cell having an active hedgehog pathway.

In another aspect, the present invention provides a method for determining whether a tumor is amenable for treatment with a BOC inhibitor, said method comprising determining the expression of BOC in a sample from said tumor, wherein the expression of BOC in said sample is indicative that said tumor is amenable for treatment with a BOC inhibitor.

In an embodiment, the above-mentioned cell is a tumor cell.

In an embodiment, the above-mentioned cancer or tumor is associated with BOC expression and/or activity, in a further embodiment with an increase in BOC expression and/or activity (e.g., BOC overexpression).

In another embodiment, the above-mentioned cancer is a brain tumor, an ovary tumor, a breast tumor, a glioblastoma, a skin tumor, a meningioma, an astrocytoma, a liver tumor, a prostate carcinoma, a bladder tumor, a lung tumor, a lymph node lymphoma, a vascular endothelium hemangioma, a kidney carcinoma or a thyroid follicular adenoma.

In an embodiment, the above-mentioned subject is a human.

In an embodiment, the above-mentioned inhibitor inhibits the expression of BOC. In a further embodiment, the above-mentioned inhibitor is an antisense oligonucleotide (ASO), a RNA interference (RNAi), a short hairpin loop interfering RNA (ShRNA) or an antisense RNA Locked Nucleic Acid analogues (LNA).

In another embodiment, the above-mentioned inhibitor inhibits the activity of BOC. In a further embodiment, the above-mentioned inhibitor specifically binds to BOC. In yet a further embodiment, the above-mentioned inhibitor is an antibody, an antigen-binding fragment of an antibody, a peptide fragment of BOC, or a protein or peptide fragment binding to BOC.

In an embodiment, the above-mentioned sample is a CNS cell, tissue or fluid. In a further embodiment, the above-mentioned CNS fluid is cerebrospinal fluid.

In an embodiment, the above-mentioned expression of BOC is determined at the nucleic acid level. In a further embodiment, the above-mentioned determining the expression of BOC comprises determining the expression of a nucleic acid encoding the polypeptide comprising the sequence of SEQ ID NO: 2. In another embodiment, the above-mentioned determining the expression of BOC comprises determining the expression of a nucleic acid comprising the coding sequence of the nucleotide sequence of SEQ ID NO: 1.

In another embodiment, the above-mentioned expression of BOC is determined at the polypeptide level. In a further embodiment, the above-mentioned determining the expression of BOC comprises determining the expression of a polypeptide comprising the sequence of SEQ ID NO: 2.

In another aspect, the present invention provides a transgenic non human mammal, the nucleated cells of which comprise a transgene including a coding region encoding BOC operatively associated with a transcriptional regulatory element, wherein the non human mammal exhibits, relative to a wild-type non human animal, an elevated BOC expression level in cerebellum cells and/or cerebellum cell precursors.

In another aspect, the present invention provides a method for prognosis of a cancer patient, said method comprising: (a) detecting an expression and/or activity of BOC in a sample from said cancer patient, and (b) prognosing said cancer patient based on said detection; wherein the detection (i.e., presence) of BOC expression and/or activity in said sample is indicative that said subject has a poor prognosis, and wherein the lack of detection (i.e., absence) of BOC expression and/or activity in said sample is indicative that said subject has a good prognosis. In an embodiment, the above-mentioned sample is a tumor sample.

In another embodiment, the above-mentioned cancer is a cancer of the central nervous system (CNS). In a further embodiment, the above-mentioned cancer is a neuroectodermal tumor. In a further embodiment, the above-mentioned neuroectodermal tumor is a medulloblastoma.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 9 shows the expression of BOC in a medulloblastoma tumor obtained from a $BOC^{+/-}$; $Ptc1^{+/-}$ mouse.

FIG. 14 shows SAGE analysis performed on 19 medulloblastoma tumor tissues using a variety of markers including BOC (FIG. 14A). These "Digital Northern" results for Boc (SAGE tag: AGAACAGACC (SEQ ID NO: 14)) were obtained from SAGE Genie (Lash A E et al., 2000. Genome Res, 10(7): 1051-1060). By analyzing their specific gene signature, each medulloblastoma tumors were characterized into Shh, Wnt or other type of medulloblastoma. The analysis was performed for markers characterizing medulloblastoma Shh (e.g., Gli1, Igf1, CXCR4, patch1, sfrp1) and markers for medulloblastoma Wnt (e.g., tnc, epha4, Dkk1, Amhr2, Emx2).

FIGS. 15A and 15B show the nucleotide sequence of human BOC (SEQ ID NO: 1), with the coding sequence indicated in bold, and FIG. 15C shows the amino acid sequence of human BOC (SEQ ID NO: 2);

FIG. 16A shows the nucleotide sequence of human SHH (SEQ ID NO: 3), with the coding sequence indicated in bold, and FIG. 16B shows the amino acid sequence of human SHH (SEQ ID NO: 4), with the sequence of the mature polypeptide indicated in bold;

FIG. 17A shows the nucleotide sequence of the murine BOC nucleic acid used in the experiments described herein (SEQ ID NO: 10), and FIG. 17B shows the amino acid sequence of the murine BOC polypeptide used in the experiments described herein (SEQ ID NO: 11). The last 8 residues (GPVATMVS (SEQ ID NO: 12), underlined) in the amino acid sequence of FIG. 17B and the corresponding nucleotides encoding these residues (ggaccggtcgccaccatggtgagc (SEQ ID NO: 13), underlined) in the nucleotide sequence of FIG. 17A are not present in the native murine BOC;

FIGS. 18A and 18B shows an alignment of the amino acid sequences of human and murine BOC;

DESCRIPTION OF ILLUSTRATIVE EMBODIMENTS

Methods of Prevention/Treatment of Cancer

Figure 1:
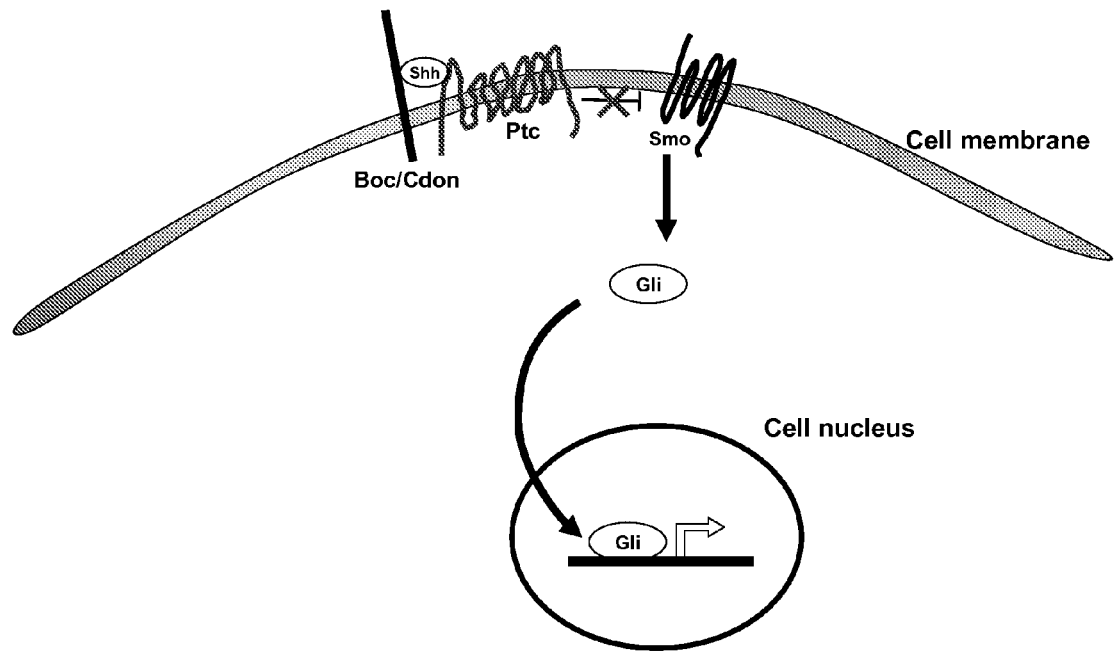
FIG. 1 shows a schematic representation of the Sonic hedgehog signalling pathway with the ligand SHH, the BOC/CDON receptors, the 12-transmembrane PTCH and the 7-transmembrane SMO proteins as well as one possible intracellular target, the transcription factor Gli.
Figure 2:
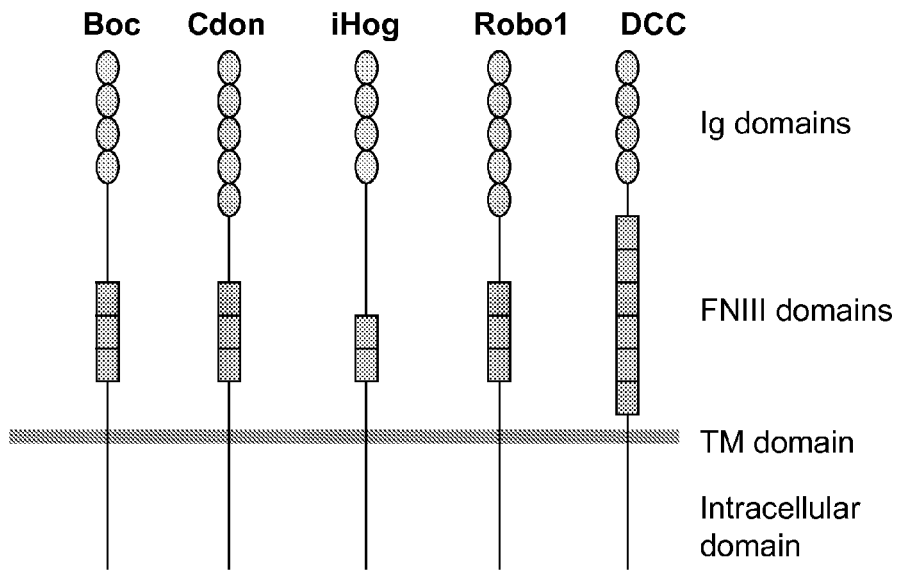
FIG. 2 is a schematic representation of some of the domains of BOC and of other related receptors (CDON, iHog, Robo1, and DCC). Oval=an Ig domain; square=a FNIII domain; TM domain=a transmembrane domain.

The invention described herein is based on the novel and unexpected observation that BOC expression is associated with increased cell proliferation, as well as with cancer development and/or progression. The present inventors have shown that overexpression of BOC in cerebellum cells results in an increase in their proliferation. The studies described herein also demonstrate that BOC$^{-/-}$ mice are less susceptible to tumor development as compared to their BOC-expressing counterparts, and that BOC is expressed and/or overexpressed in various human tumors, including medulloblastoma tumors. The present inventors have further shown that expression of Boc in medulloblastoma tumors is generally associated with a poor prognosis.

Accordingly, in a first aspect, the present invention provides a method for preventing and/or treating cancer comprising administering to a subject in need thereof an effective amount of a brother of CDON (BOC, also knows as biregional CDON-binding protein) inhibitor (i.e., an agent capable of inhibiting BOC expression and/or activity).

The present invention also provides a method for inhibiting the proliferation and/or differentiation of a cell (e.g., a tumor cell) having an active hedgehog pathway comprising contacting said cell with a BOC inhibitor.

In another aspect, the present invention provides a use of a BOC inhibitor for preventing and/or treating cancer in a subject.

The present invention also provides a use of a BOC inhibitor for the preparation of a medicament for preventing and/or treating cancer in a subject.

The present invention also provides a use of a BOC inhibitor for the preparation of a medicament for inhibiting the proliferation and/or differentiation of a cell (e.g., a tumor cell) having an active hedgehog pathway.

In another aspect, the present invention provides a BOC inhibitor, or a composition comprising said BOC inhibitor, and a pharmaceutically acceptable carrier, for preventing and/or treating cancer in a subject.

In an embodiment, the above-mentioned inhibitor blocks or inhibits paracrine Hedgehog signaling, for example by inhibiting the activation of Hedgehog signaling in the surrounding stroma by Hh ligand-secreting tumor cells. The activation of Hh signaling in the stroma surrounding the tumors has recently been shown to create a favorable environment for tumor growth (Theunissen J W and de Sauvage F J., *Cancer Res.* 2009, 69(15): 6007-10. Epub 2009 Jul. 28; Scales S J and de Sauvage F J. *Trends Pharmacol Sci.* 2009 30(6): 303-12. Epub 2009 May 13; Tian H et al., *Proc Natl Acad Sci USA.* 2009 106(11): 4254-9. Epub 2009 Feb. 25; Yauch R L et al., *Nature.* 2008, 455(7211): 406-10. Epub 2008 Aug. 27).

Combination of Active/Therapeutic Agents

In an embodiment, the above-mentioned prevention/treatment comprises the use/administration of more than one (i.e. a combination of) active/therapeutic agent (e.g., an agent capable of inhibiting BOC expression and/or activity). The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one prophylactic or therapeutic agent in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) of the present invention is used/administered in combination with one or more agent (s) currently used to prevent or treat the disorder in question (e.g., an anticancer agent).

Dosage

The amount of the agent or pharmaceutical composition which is effective in the prevention and/or treatment of a particular disease, disorder or condition (e.g., cancer) will depend on the nature and severity of the disease, the chosen prophylactic/therapeutic regimen (i.e., compound, DNA construct, protein, cells), the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect a beneficial prophylactic and/or therapeutic response in the patient over time. The size of the dose will also be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

The terms "treat/treating/treatment" and "prevent/preventing/prevention" as used herein, refers to eliciting the desired biological response, i.e., a therapeutic and prophylactic effect, respectively. In accordance with the subject invention, the therapeutic effect comprises one or more of a decrease/ reduction in tumor, a decrease/reduction in the severity of the cancer (e.g., a reduction or inhibition of metastasis development), a decrease/reduction in symptoms and cancer-related effects, an amelioration of symptoms and cancer-related effects, and an increased survival time of the affected host animal, following administration of the agent/composition of the invention. In accordance with the invention, a prophylactic effect may comprise a complete or partial avoidance/inhibition or a delay of cancer development/progression (e.g., a complete or partial avoidance/inhibition or a delay of metastasis development), and an increased survival time of the affected host animal, following administration of the agent that inhibits BOC expression and/or activity (or of a composition comprising the agent).

As such, a "therapeutically effective" or "prophylactically effective" amount of an agent capable of inhibiting the expression and/or activity of BOC, or a combination of such agents, may be administered to an animal, in the context of the methods of treatment and prevention, respectively, described herein.

As used herein, "inhibition" or "decrease" of BOC expression/level or activity refers to a reduction in BOC expression or activity of at least 10% as compared to reference (e.g., normal) expression or activity, in an embodiment of at least 20% lower, in a further embodiment of at least 30%, in a further embodiment of at least 40%, in a further embodiment of at least 50%, in a further embodiment of at least 60%, in a further embodiment of at least 70%, in a further embodiment of at least 80%, in a further embodiment of at least 90%, in a further embodiment of 100% (complete inhibition).

Neoplastic Disease and Cancer

By the term "neoplastic disease" or "invasive disease" is meant a disease associated with new growth of any body tissue. A neoplastic tissue according to the invention may retain some characteristics of the tissue from which it arises but has biochemical characteristics that are distinct from those of the parent tissue. The tissue formed due to neoplastic growth is a mutant version of the original tissue and appears to serve no physiologic function in the same sense as did the original tissue. It may be benign or malignant.

In one embodiment, the present invention relates to benign neoplastic disease. In another embodiment the present invention relates to malignant neoplastic disease. In specific embodiments, the malignant neoplastic disease is cancer.

Cancer is defined herein as a disease characterized by the presence of cancer cells which are characterized by two heritable properties: they and their progeny are able (1) to reproduce unrestrained in defiance of the normal restrains (i.e., they are neoplastic) and (2) invade and colonize territories normally reserved for other cells (i.e., they are malignant). Invasiveness of cancer cells usually implies an ability to break loose, enter the bloodstream or lymphatic vessels, and form secondary tumors, or metastases at the other distant sites in the body.

Cancer refers herein to a cluster of cancer or tumor cells showing over proliferation by non-coordination of the growth and proliferation of cells due to the loss of the differentiation ability of cells. The terms "cancer cell" and "tumor cell" are used interchangeably herein.

In an embodiment, the above-mentioned cancer/tumor is a brain tumor (e.g., brain ependynoma, a medulloblastoma), an ovary tumor (e.g., ovary carcinoma, endometriosis or adenocarcinoma), a breast tumor (e.g., breast fibroadenoma or carcinoma), a glioblastoma, a skin tumor (e.g., skin melanoma), a meningioma, an astrocytoma, a liver tumor (e.g., liver cholangiocarcinoma), a prostate carcinoma, a bladder tumor (e.g., bladder adenocarcinoma), a lung tumor, a lymph node lymphoma, a vascular endothelium hemangioma, a kidney carcinoma or a thyroid follicular adenoma.

In an embodiment, the above-mentioned cancer/tumor is associated with BOC expression and/or activity (e.g., BOC overexpression or increased/abnormal BOC activity). In another embodiment, the above-mentioned cancer is a cancer of the central nervous system (e.g., brain cancer). In a further embodiment, the above-mentioned cancer is a neuroectodermal tumor. In yet a further embodiment, the above-mentioned cancer is a medulloblastoma. In a further embodiment, the above-mentioned medulloblastoma is a medulloblastoma associated with a deregulation of the SHH pathway and/or of the Wnt pathway.

Regulation of BOC Expression or Activity

The regulation of BOC expression/level and/or activity could be achieved by various mechanisms, which among others could act at the level of (i) transcription (ii) translation (e.g., degradation of BOC mRNA using antisense oligonucleotides), (iii) post-translational modifications, e.g., glycosylation, sulfation, phosphorylation (e.g., kinase inhibitors), ubiquitination (iv) cellular localization, (v) shedding from the membrane, (vi) protein-protein interaction, for example by modulating expression or activity of a protein that binds to BOC or to a BOC ligand (e.g., overexpression of GAS-1, HIP-1 and/or CDON which bind to SHH and compete with BOC). These regulatory processes occur through different molecular interactions that could be modulated by a variety of compounds or modulators.

BOC Gene

As used herein the terms "BOC gene" or "BOC" refers to genomic DNA encoding sequences comprising those sequences referred to in GenBank by GeneID number 91653. The description of the various aspects and embodiments of the invention is provided with reference to exemplary BOC nucleic acid sequence (SEQ ID NO: 1) and amino acid sequence (SEQ ID NO: 2). Such reference is meant to be exemplary only and the various aspects and embodiments of the invention are also directed to other BOC nucleic acids and polypeptides, such as BOC nucleic acid or polypeptide mutants/variants, splice variants of BOC nucleic acids, BOC variants from species to species or subject to subject. UNIPROT accession No. Q9BWV1 describes three BOC isoforms produced by alternative splicing. The isoform 1 (identifier: Q9BWV1-1, 1114 amino acids, SEQ ID NO: 2) has been designated the "canonical" sequence. All positional information refers to it. The sequence of isoform 2 (identifier: Q9BWV1-2) differs from the canonical sequence by the deletion of the amino acids at positions 1-299. The sequence of isoform 3 (identifier: □9BWV1-3) differs from the canonical sequence as follows: position 514: K→KQ (i.e. insertion of a glutamine residue). Natural variants in the coding sequence include sequences with an alanine (A) to valine (V) substitution at position 43 (rs34208374); a glycine (G) to arginine (R) substitution at position 309 (rs3814400); a threonine (T) to isoleucine (I) substitution at position 675 (rs61735687); a valine (V) to methionine (M) substitution at position 713; a lysine (K) to asparagine (N) substitution at position 883 (rs35536878); a proline (P) to serine (S) substitution at position 912 (rs3814404); and a glutamine (Q) to histidine (H) substitution at position 915 (rs3814405), as well as frameshift mutations at position 340 (rs35253657) and at position 1087 (rs35293574). The presence of these variants, if associated with an increase or decrease BOC expression and/or activity, may be used for diagnostic and/or prognostic applications, as described below. Natural variants in the non coding regions or coding sequence exist that may affect the function/activity and expression of BOC. Without being so limited, Table I below lists of known BOC variants in the coding and non coding regions of BOC.

TABLE I

Natural BOC variants

| ID | Type | Chr: bP | Alleles | Ambiguity | Amino Acid | AA coordinate | Class | Source | Validation |
|---|---|---|---|---|---|---|---|---|---|
| rs9822391 | 5prime_utr | 3: 112935113 | G/C | S | — | — | snp | dbSNP, Affy GenomeWideSNP_6.0 | cluster, freq, hapmap |
| rs4682130 | intronic | 3: 112930138 | C/G | S | — | — | snp | ENSEMBL:Watson, HGVbase, dbSNP, ENSEMBL:Venter | cluster, freq, doublehit, hapmap |
| rs34208374 | non_synonymous_coding | 3: 112969432 | C/T | Y | A/V | 43 (2) | snp | dbSNP | — |
| rs34174640 | intronic | 3: 112969704-112969703 | -/C | | — | — | insertion | dbSNP | — |
| rs712528 | intronic | 3: 112989603 | A/T | W | — | — | snp | HGVbase, dbSNP, TSC | cluster, freq, submitter, hapmap |
| rs9819129 | synonymous_coding | 3: 112989763 | C/T | Y | S | 213 (3) | snp | dbSNP | cluster, freq, hapmap |
| rs3930154 | intronic | 3: 112991196 | C/G | S | — | — | snp | ENSEMBL:Watson, HGVbase, ENSEMBL:celera, dbSNP, TSC, ENSEMBL:Venter, Illumina_Human1M-duoV3 | cluster, freq, hapmap |
| rs16860765 | synonymous_coding | 3: 112991306 | C/A | M | T | 239 (3) | snp | dbSNP, Illumina_Human1M-duoV3 | cluster, freq, hapmap |
| rs3814398 | synonymous_coding | 3: 112991312 | C/T | Y | I | 241 (3) | snp | HGVbase, ENSEMBL:celera, dbSNP, Affy GenomeWideSNP_6.0, Illumina_Human1M-duoV3 | cluster, freq, hapmap |
| rs3814399 | synonymous_coding | 3: 112991492 | C/T | Y | A | 301 (3) | snp | HGVbase, dbSNP, Affy GenomeWideSNP_6.0, Illumina_Human1M-duoV3 | freq, hapmap |
| rs3814400 | non_synonymous_coding | 3: 112991514 | G/A | R | G/R | 309 (1) | snp | HGVbase, dbSNP | — |
| rs11717833 | intronic | 3: 112991842 | A/G | R | — | — | snp | dbSNP, Illumina_Human1M-duoV3 | cluster, freq, doublehit, hapmap |

TABLE I-continued

Natural BOC variants

| ID | Type | Chr: bP | Alleles | Ambi-guity | Amino Acid | AA co-ordinate | Class | Source | Validation |
|---|---|---|---|---|---|---|---|---|---|
| rs11710894 | synonymous_coding | 3: 112991959 | C/T | Y | P | 335 (3) | snp | dbSNP, Illumina_Human1M-duoV3 | cluster, freq, hapmap |
| rs35253657 | frameshift_coding | 3: 112991974 | C/− | | | 340 (3) | deletion | dbSNP | — |
| rs7612497 | intronic | 3: 112992225 | G/A | R | — | — | snp | dbSNP | — |
| rs13093741 | synonymous_coding | 3: 112993292 | C/T | Y | L | 435 (3) | snp | dbSNP, ENSEMBL:Venter | cluster, freq, hapmap |
| rs13094203 | synonymous_coding | 3: 112993367 | G/A | R | P | 460 (3) | snp | dbSNP, ENSEMBL:Venter | cluster, freq, hapmap |
| rs7615578 | synonymous_coding | 3: 112993412 | C/T | Y | P | 475 (3) | snp | dbSNP, Illumina_Human1M-duoV3 | cluster, freq, hapmap |
| rs7615718 | intronic | 3: 112993561 | C/T | Y | — | — | snp | dbSNP | — |
| rs7627584 | intronic | 3: 112996898 | C/T | Y | — | — | snp | dbSNP | freq, hapmap |
| GA021627 | essentail_splice_site, intronic | 3: 112997106 | T/A | W | — | — | snp | Illumina_Human1M-duoV3 | — |
| rs3814401 | intronic | 3: 112997141 | G/A | R | — | — | snp | HGVbase, dbSNP, Illumina_Human1M-duoV3 | cluster, freq, hapmap |
| rs775228 | synonymous_coding | 3: 112997554 | A/G | R | K | 579 (3) | snp | HGVbase, ENSEMBL:celera, Illumina_CytoSNP12v1, dbSNP, TSC, ENSEMBL:Venter, Illumina_Human1M-duoV3 | cluster, freq, submitter, doublehit, hapmap |
| rs13066489 | intronic | 3: 112997725 | T/G | K | — | — | snp | dbSNP, ENSEMBL:Venter | — |
| rs3856720 | splice_site, intronic | 3: 112998090 | T/C | Y | — | — | snp | ENSEMBL:celera, dbSNP, TSC, Illumina_Human1M-duoV3 | cluster, freq, doublehit, hapmap |
| rs2649878 | synonymous_coding | 3: 112998265 | A/G | R | P | 661 (3) | snp | HGVbase, ENSEMBL:celera, dbSNP, TSC, Illumina_Human1M-duoV3 | cluster, freq, doublehit, hapmap |
| rs2650100 | synonymous_coding | 3: 112998268 | G/A | R | S | 662 (3) | snp | HGVbase, dbSNP, TSC | cluster, freq |
| rs34039703 | intronic | 3: 112998343-112998342 | −/C | | — | — | insertion | dbSNP | — |
| rs11920382 | intronic | 3: 112998373 | C/T | Y | — | — | snp | ENSEMBL:celera, dbSNP | cluster |
| rs61735687 | non_synonymous_coding | 3: 112998674 | C/T | Y | T/I | 675 (2) | snp | dbSNP | — |
| rs16860782 | synonymous_coding | 3: 112998792 | A/G | R | A | 714 (3) | snp | Affy GeneChip 500K Array, dbSNP, Affy GenomeWideSNP_6.0, Illumina_Human1M-duoV3 | cluster, freq, hapmap |
| GA021628 | essential_splice_site, intronic | 3:113000001 | G/C | S | — | — | snp | Illumina_Human1M-duoV3 | — |
| GA021629 | splice_site, intronic | 3: 113000003 | G/C | S | — | — | snp | Illumina_Human1M-duoV3 | — |
| rs63500461 | intronic | 3: 113002186-113002185 | −/T | | — | — | insertion | dbSNP | — |
| rs5851891 | intronic | 3: 113002194-113002193 | −/T | | — | — | insertion | dbSNP | — |
| rs63715961 | intronic | 3: 113002195-113002194 | −/T | | — | — | insertion | dbSNP | — |
| rs35536878 | non_synonymous_coding | 3: 113002475 | G/C | S | K/N | 883 (3) | snp | dbSNP | cluster, freq |
| rs55671299 | intronic | 3: 113002500 | G/T | K | — | — | snp | dbSNP | — |
| rs41271349 | intronic | 3: 113003157 | C/T | Y | — | — | snp | dbSNP | — |
| rs59291757 | synonymous_coding | 3: 113003234 | G/A | R | P | 902 (3) | snp | dbSNP | — |
| rs3814404 | non_synonymous_coding | 3: 113003262 | C/T | Y | P/S | 912 (1) | snp | HGVbase, dbSNP | — |
| rs3814405 | non_synonymous_coding | 3: 113003273 | G/T | K | Q/H | 915 (3) | snp | HGVbase, dbSNP | cluster, freq |
| rs41271353 | intronic | 3: 113003466 | G/A | R | — | — | snp | dbSNP | — |
| rs41271351 | intronic | 3: 113003562 | G/C | S | — | — | snp | dbSNP | — |
| rs34440754 | intronic | 3: 113003578-113003577 | −/A | | — | — | insertion | dbSNP | — |

TABLE I-continued

Natural BOC variants

| ID | Type | Chr: bP | Alleles | Ambiguity | Amino Acid | AA co-ordinate | Class | Source | Validation |
|---|---|---|---|---|---|---|---|---|---|
| rs775222 | intronic | 3: 113003595 | G/C | S | — | — | snp | HGVbase, dbSNP | cluster, freq, hapmap |
| rs13084974 | intronic | 3: 113004123 | C/G | S | — | — | snp | dbSNP, ENSEMBL:Venter | — |
| rs41271355 | intronic | 3: 113004155 | G/A | R | — | — | snp | dbSNP | — |
| rs34600669 | synonymous_coding | 3: 113004240 | C/T | Y | D | 995 (3) | snp | dbSNP | — |
| rs16860788 | intronic | 3: 113004421 | C/T | Y | — | — | snp | dbSNP, illumina_Human1M-duoV3 | freq, hapmap |
| rs35293574 | frameshift_coding | 3: 113005623 | G/− | | | 1087 (1) | deletion | dbSNP | — |
| rs5022662 | 3prime_utr | 3: 113005754 | A/T | W | — | — | snp | dbSNP, ENSEMBL:Venter | — |
| rs1553220 | 3prime_utr | 3: 113005756-113005755 | −/A/T | | — | — | mixed | HGVbase, dbSNP | — |
| rs5851892 | 3prime_utr | 3: 113005764 | A/− | | | | deletion | dbSNP | — |
| rs34562339 | 3prime_utr | 3: 113005766-113005765 | −/A | | | | insertion | dbSNP | — |
| rs2399476 | 3prime_utr | 3: 113005952 | G/A | R | — | — | snp | HGVbase, dbSNP, TSC | cluster, freq, submitter, doublehit |
| ENSSNP12397219 | 3prime_utr | 3: 113006041 | G/A | R | — | — | snp | ENSEMBL:Watson | — |
| GA003496 | 3prime_utr | 3: 113006054 | T/C | Y | — | — | snp | Illumina_Human1M-duoV3 | — |
| rs9826018 | 3prime_utr | 3: 113006135 | C/T | Y | — | — | snp | dbSNP | doublehit |

SHH Gene

As used herein, the terms "SHH gene" or "SHH" refers to genomic DNA encoding sequences comprising those sequences referred to in GenBank by GeneID number 6469. The description of the various aspects and embodiments of the invention is provided with reference to an exemplary SHH nucleic acid (SEQ ID NO: 3) and polypeptide (SEQ ID NO: 4). Such reference is meant to be exemplary only and the various aspects and embodiments of the invention are also directed to other genes that express alternate SHH nucleic acids, such as mutant SHH nucleic acids, splice variants of SHH nucleic acids, SHH variants from species to species or subject to subject.

BOC Inhibitors

As used herein, the term "BOC inhibitor" includes any compound able to directly or indirectly affect the regulation of BOC by reducing for example the expression of BOC (i.e., transcription and/or the translation), or a BOC activity. It includes intracellular as well as extracellular BOC inhibitors. Without being so limited, such inhibitors include siRNA, antisense molecules, proteins, peptides, small molecules, antibodies, etc.

As used herein the terms "BOC activity" and "BOC function" refer to detectable (direct or indirect) enzymatic, biochemical or cellular activity attributable to BOC. Without being so limited, such activities include the binding of BOC to SHH (or to a peptide fragment of SHH), the activation of any subsequent step of the Hedgehog pathway including the transcription of Hh-targeted genes (e.g., Gli-1, PTC), and cell proliferation (which may be measured, for example, by an MTT assay, BrdU incorporation, Carboxyfluorescein succinimidyl ester (CFSE) dilution, or Ki-67 immunodetection).

BOC activity may also be measured by protein-protein binding assay using purified BOC and a purified BOC ligand (e.g., SHH).

BOC activity could also be indirectly measured by evaluating the level of expression of BOC (or of a nucleic acid/polypeptide whose expression is modulated by BOC activity), or a fragment thereof, in cells as well as in a biological sample (tissue, organ, fluid). BOC expression levels could be determined at the polypeptide and/or nucleic acid levels using any standard methods known in the art (see below). BOC activity could also be indirectly measured by evaluating the level of expression or activity of a reporter gene (e.g., luciferase, β-galactosidase, alkaline phosphatase, GFP) operably linked to a transcriptionally regulatory element normally associated with a BOC gene or with a gene whose expression is modulated by BOC activity (e.g., GLI-1) (Yao et al., *Cell* (2006) 125: 343-357).

Antisense Molecules

In an embodiment, the agent capable of inhibiting or reducing expression of BOC is an antisense molecule.

Generally, the principle behind antisense technology is that an antisense molecule hybridizes to a target nucleic acid and effects modulation of gene expression such as transcription, splicing, translocation of the RNA to the site of protein translation, translation of protein from the RNA. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi is a form of antisense-mediated gene silencing involving the introduction of dsRNA (typically of less than 30 nucleotides in length, and generally about 19 to 24 nucleotides in length) leading to the sequence-specific reduction of targeted endogenous mRNA levels, here the RNA transcript of the BOC gene. Such dsRNA are generally substantially complementary to at least part of an RNA transcript of the BOC gene. Another example of modulation of gene expression is the RNA analogue Locked Nucleic Acid (LNA). Other examples relate to double stranded nucleic acid molecules including small nucleic acid molecules, such as short interfering nucleic acid (siNA), short interfering RNA (sRNA), micro-RNA (miRNA). The use of single stranded antisense oligonucleotides (ASO) is also encompassed by the method of the present invention. Sequence-specificity makes antisense compounds extremely attractive as therapeutics to selectively modulate the expression of genes involved in the pathogenesis of any one of a variety of diseases.

Chemically modified nucleosides are routinely used for incorporation into antisense compounds to enhance one or more properties, such as nuclease resistance, pharmacokinetics or affinity for a target RNA.

As used herein "antisense molecule" is meant to refer to an oligomeric molecule, particularly an antisense oligonucleotide for use in modulating the activity or function of nucleic acid molecules encoding a BOC polypeptide (e.g., the polypeptide of SEQ ID NO: 2), ultimately modulating the amount of said BOC produced in tumor cells or in producer cells located in normal distal or surrounding tissues. This is accomplished by providing oligonucleotide molecules which specifically hybridize with one or more nucleic acids encoding BOC. As used herein, the term "nucleic acid encoding a BOC polypeptide" encompasses DNA encoding said polypeptide, RNA (including pre-mRNA and mRNA) transcribed from such DNA, and also cDNA derived from such RNA (e.g., a nucleic acid comprising the coding sequence of the nucleotide sequence set forth in SEQ ID NO: 1). The specific hybridization of an oligomeric compound with its target nucleic acid interferes with the normal function of the nucleic acid. The overall effect of such interference with target nucleic acid function is modulation of the expression of BOC. In the context of the present invention, "modulation" means either an increase (stimulation) or a decrease (inhibition) in the expression of a gene.

In the context of this invention, "hybridization" means hydrogen bonding between complementary nucleoside or nucleotide bases. Terms "specifically hybridizable" and "complementary" are the terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. Such conditions may comprise, for example, 400 mM NaCl, 40 mM PIPES pH 6.4, 1 mM EDTA, at 50 to 70° C. for 12 to 16 hours, followed by washing. The skilled person will be able to determine the set of conditions most appropriate for a test of complementarity of two sequences in accordance with the ultimate application of the hybridized nucleotides.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

Examples of modified nucleotides include a 2'-O-methyl modified nucleotide, a nucleotide comprising a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate and a non-natural base comprising nucleotide.

Methods to produce antisense molecules directed against a nucleic acid are well known in the art. The antisense molecules of the invention may be synthesized in vitro or in vivo.

The antisense molecule may be expressed from recombinant viral vectors, such as vectors derived from adenoviruses, adeno-associated viruses, retroviruses, herpesviruses, and the like. Such vectors typically comprises a sequence encoding an antisense molecule of interest (e.g., a dsRNA specific for BOC) and a suitable promoter operatively linked to the antisense molecule for expressing the antisense molecule. The vector may also comprise other sequences, such as regulatory sequences, to allow, for example, expression in a specific cell/tissue/organ, or in a particular intracellular environment/compartment. Methods for generating, selecting and using viral vectors are well known in the art.

Examples of antisense molecules inhibiting the expression of BOC, as well as methods for producing same, are described in Okada et al., 2006, supra. Also, Human BOC-specific siRNA are commercially available, for example from Santa Cruz Biotechnology, Inc (Cat. No. sc-72161, sc-72161-SH and sc-72161-V) and Origene (Cat. No. TR306384). Also, several providers (e.g., InvivoGen, Qiagen, Ambion, Inc.) offer custom-made antisense synthesis services.

Peptide Compound

By the "peptide fragment of a BOC" in the present context is meant any peptide fragment derived from the amino acid sequence set forth in SEQ ID NO: 2, fragments, variants thereof, or modified forms, capable of inhibiting the activity of BOC. In an embodiment, the above-mentioned fragment is the ectodomain of BOC (extracellular domain). In a further embodiment, the above-mentioned fragment is a fibronectin type III (FNIII) domain/repeat (e.g., FNIIIc).

In another embodiment, the agent of the invention is a peptide fragment of BOC corresponding to residues 694-802 of the amino acid sequence of murine Boc (GenBank accession No. NP_766094) (Okada et al., 2006, supra).

In an embodiment, the peptide fragment of BOC inhibiting BOC activity is a natural or synthetic contiguous amino acid sequence of at least 60 amino acids from the sequence set forth in SEQ ID NO: 2, or variants thereof.

In another embodiment, the "peptide fragment" of the invention is a peptide fragment derived from an interacting partner of BOC, such as SHH and CDON or other BOC-binding proteins having an inhibitory effect on BOC activity. In another embodiment, the "peptide fragment" of the invention is a peptide fragment from an interacting partner of a BOC ligand (e.g., SHH), such as GAS-1 and HIP-1, which inhibits the activation of BOC by its ligand.

A peptide fragment inhibiting BOC activity of the present invention may be prepared by conventional synthetic methods or recombinant DNA technologies. The methods for synthetic production of peptides are well known in art. Chemically modified amino acids are used for incorporation into compounds to enhance one or more properties, such as protease resistance, pharmacokinetics or affinity for its molecular target. Detailed descriptions as well as practical advice for producing synthetic peptides may be found in Synthetic Peptides: A User's Guide (Advances in Molecular Biology), Grant G. A. ed., Oxford University Press, 2002, or in Pharmaceutical Formulation: Development of Peptides and Proteins, Frokjaer and Hovgaard eds., Taylor and Francis, 1999.

BOC Antibody

By "BOC antibody" or "anti-BOC" in the present context is meant an antibody capable of detecting (i.e. binding to) a BOC protein or a BOC protein fragment. In an embodiment, the above-mentioned antibody inhibits the biological activity of BOC. In another embodiment, the BOC protein fragment is an extracellular domain (ectodomain) of BOC. In another embodiment, the BOC protein fragment is an intracellular domain of BOC. In a further embodiment, the BOC protein fragment is a FNIII domain/repeat. In another embodiment, the BOC protein fragment is an extracellular domain of BOC that is shedded from the cell surface in the extracellular fluid.

By "BOC antibody" or "anti-BOC" in the present context is also meant an antibody capable of binding (e.g., specifically binding) to BOC, and inhibiting its biological activity (e.g., its activity of binding to SHH or its activity on cell proliferation).

As used herein, the term "anti-BOC" also refers to an antibody that specifically binds to (interacts with) a BOC polypeptide (e.g., the polypeptide of SEQ ID NO: 2) and displays no substantial binding to other naturally occurring proteins other than the ones sharing the same antigenic determinants as a BOC polypeptide. The term antibody or immunoglobulin is used in the broadest sense, and covers monoclonal antibodies (including full-length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g., Fab and Fab' fragments) which inhibit or neutralize their respective interaction domains in Hyphen and/or are specific thereto.

Polyclonal antibodies are preferably raised in animals by multiple subcutaneous (s.c.), intravenous (i.v.) or intraperitoneal (i.p.) injections of the relevant antigen with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfo-succinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen (BOC polypeptide or a fragment thereof), immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to ¹/₁₀ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Antibodies/antibody fragments specifically binding to BOC are commercially available (from R&D Systems™, Cat. Nos. MAB2036, MAB20361, AF2036, AF2385, for example).

In an embodiment, the above-mentioned antibody blocks the interaction between BOC and an interacting partner, such as a BOC ligand (e.g., SHH). In a further embodiment, the above-mentioned antibody is an anti-SHH antibody. In a further embodiment, the above-mentioned antibody is anti-SHH monoclonal antibody clone 5E1 (Ericson et al., *Cell* (1996) 87: 661-673).

Non-Antibody-Based BOC Inhibitors

Inhibitors of BOC may also be in the form of non-antibody-based scaffolds, such as avimers (Avidia); DARPins (Molecular Partners); Adnectins (Adnexus), Anticalins (Pieris) and Affibodies (Affibody). The use of alternative scaffolds for protein binding is well known in the art (see, for example, Binz and Plückthun, 2005, *Curr. Opin. Biotech.* 16: 1-11).

Agents and Pharmaceutical Compositions

In another aspect, the present invention provides a BOC inhibitor for preventing and/or treating cancer. Such an agent may be, for example (i) an antisense compound against the sequence set forth in SEQ ID NO: 1 (BOC) which inhibits BOC expression; (ii) a peptide fragment capable of binding to a BOC polypeptide and inhibiting the activity of said polypeptide; (iii) a peptide fragment capable of inhibiting the activity of BOC; (iv) an antibody (e.g., polyclonal or monoclonal), natural or artificial variants, or antibody fragments, which specifically binds to BOC and blocks its activity; (v) a small molecule that inhibits the activity of BOC. In an embodiment, the antibody, natural or artificial variants, or antibody fragments specifically binds to an epitope located in the ectodomain of a BOC polypeptide (e.g., a FNIII domain), and inhibits its activity.

The invention also provides a pharmaceutical composition (medicament) comprising at least one agent of the invention (e.g., a BOC inhibitor), and a pharmaceutically acceptable diluent, carrier, salt or adjuvant. Such carriers include, for example, saline, buffered saline, dextrose, water, glycerol, ethanol, and combinations thereof. The pharmaceutical composition may be adapted for the desired route of administration (e.g., oral, parental, intravenous, intramuscular, intraperitoneal, aerosol).

The invention also provides pharmaceutical compositions which comprise one or more agent(s) modulating BOC activity. Typically, the activity of BOC is reduced or inhibited. The invention also provides pharmaceutical compositions which comprise one or more agent(s) modulating BOC activity in combination with other anticancer treatment including chemotherapeutical agents, such as cyclopamine, CUR0199691, Cisplatin™ Oxaliplatin™ and their derivatives, cyclophosphamide compound (Cy), 13-cis retinoic acid (RA), histone deacetylase inhibitor (SAHA), nucleotide analogues (e.g., 5-fluoro uracyl, 5-AZA), kinase inhibitors, GDC-0449 (antagonist of Hedgehog signaling), etc.

The present invention also provides a kit or package comprising the above-mentioned agent or pharmaceutical compositions. Such kit may further comprises, for example, instructions for the prevention and/or treatment of cancer, containers, devices for administering the agent/composition, etc.

Screening Assays

Given the correlation between BOC expression/activity and cancer development/progression, compounds which are capable of decreasing BOC expression/activity may be used for the prevention and/or treatment of cancer. Therefore, the invention further relates to screening methods for the identification and characterization of compounds capable of decreasing BOC expression and/or activity, which may be used for the prevention and/or treatment of cancer.

The present invention also provides a method (e.g., an in vitro method) for determining whether a test compound is useful for the prevention and/or treatment of cancer, said method comprising: (a) contacting said test compound with a BOC polypeptide, or a fragment thereof or variant thereof having BOC activity; and (b) determining the activity of the BOC polypeptide, fragment or variant thereof, in the presence or absence of said test compound; wherein a decrease in the activity of BOC in the presence of said test compound relative to the absence thereof is indicative that said test compound may be used for the prevention and/or treatment of cancer.

The present invention also provides a method (e.g., an in vitro method) for determining whether a test compound is useful for the prevention and/or treatment of cancer, said method comprising: (a) contacting said test compound with a cell expressing BOC; and (b) determining the expression and/or activity of BOC in the presence or absence of said test compound; wherein a decrease in the expression and/or activity of BOC in the presence of said test compound relative to the absence thereof is indicative that said test compound may be used for the prevention and/or treatment of cancer.

The present invention also provides a method (e.g., an in vitro method) for determining whether a test compound is useful for the prevention and/or treatment of cancer, said method comprising: (a) contacting said test compound with a cell comprising a first nucleic acid comprising a transcriptionally regulatory element normally associated with a BOC gene, operably linked to a second nucleic acid comprising a reporter gene encoding a reporter protein; and (b) determining whether the reporter gene expression and/or reporter protein activity is decreased in the presence of said test compound; wherein said decrease in reporter gene expression and/or reporter protein activity is indicative that said test compound may be used for prevention and/or treatment of cancer.

The present invention also provides a method (e.g., an in vitro method) for determining whether a test compound is useful for the prevention and/or treatment of cancer, said method comprising: (a) contacting said test compound with a cell comprising a first nucleic acid comprising a transcriptionally regulatory element normally associated with a gene whose expression is modulated by BOC activity (e.g., GLI-1), operably linked to a second nucleic acid comprising a reporter gene encoding a reporter protein; and (b) determining whether the reporter gene expression and/or reporter protein activity is decreased in the presence of said test compound; wherein said decrease in reporter gene expression and/or reporter protein activity is indicative that said test compound may be used for prevention and/or treatment of cancer.

The above-mentioned methods may be employed either with a single test compound or a plurality or library (e.g., a combinatorial library) of test compounds. In the latter case, synergistic effects provided by combinations of compounds may also be identified and characterized. The above-mentioned compounds may be used for prevention and/or treatment of cancer, or may be used as lead compounds for the development and testing of additional compounds having improved specificity, efficacy and/or pharmacological (e.g., pharmacokinetic) properties. In an embodiment the compound may be a prodrug which is altered into its active form at the appropriate site of action, (e.g., a cell, tissue or organ affected by cancer). In certain embodiments, one or a plurality of the steps of the screening/testing methods of the invention may be automated.

Such assay systems may comprise a variety of means to enable and optimize useful assay conditions. Such means may include but are not limited to: suitable buffer solutions, for example, for the control of pH and ionic strength and to provide any necessary components for optimal BOC activity and stability (e.g., protease inhibitors), temperature control means for BOC activity and or stability, and detection means to enable the detection of a BOC activity reaction product. A variety of such detection means may be used, including but not limited to one or a combination of the following: radiolabelling (e.g., $^{32}P$, $^{14}C$, $^{3}H$), antibody-based detection, fluorescence, chemiluminescence, spectroscopic methods (e.g., generation of a product with altered spectroscopic properties), various reporter enzymes or proteins (e.g., horseradish peroxidase, green fluorescent protein), specific binding reagents (e.g., biotin/(strept)avidin), and others.

The assay may be carried out in vitro utilizing a source of BOC which may comprise naturally isolated or recombinantly produced BOC, in preparations ranging from crude to pure. Recombinant BOC may be produced in a number of prokaryotic or eukaryotic expression systems, which are well known in the art. Such assays may be performed in an array format.

As noted above, the invention further relates to methods for the identification and characterization of compounds capable of decreasing BOC gene expression. Such a method may comprise assaying BOC gene expression in the presence versus the absence of a test compound. Such gene expression may be measured by detection of the corresponding RNA or protein, or via the use of a suitable reporter construct comprising one or more transcriptional regulatory element(s) normally associated with a BOC gene, operably-linked to a reporter gene.

A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences.

Generally, operably-linked DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked. The expression of such a reporter gene may be measured on the transcriptional or translational level, e.g., by the amount of RNA or protein produced. RNA may be detected by for example Northern analysis or by the reverse transcriptase-polymerase chain reaction (RT-PCR) method (see for example Sambrook et al. (1989) Molecular Cloning: A Laboratory Manual ($2^{nd}$ edition), Cold Spring Harbor Laboratory Press, Cold Spring Harbor, N.Y., USA).

Protein levels may be detected either directly using affinity reagents (e.g., an antibody or fragment thereof (for methods, see for example Harlow, E. and Lane, D (1988) Antibodies: A Laboratory Manual, Cold Spring Harbor Laboratory Press, Cold Spring Harbor, N.Y.); a ligand which binds the protein) or by other properties (e.g., fluorescence in the case of green fluorescent protein) or by measurement of the protein's activity, which may entail enzymatic activity to produce a detectable product (e.g., with altered spectroscopic properties) or a detectable phenotype (e.g., alterations in cell growth/function). Suitable reporter genes include but are not limited to chloramphenicol acetyltransferase, β-D galactosidase, luciferase, or green fluorescent protein (GFP).

BOC levels (expression levels) could be determined using any standard methods known in the art. Non-limiting examples of such methods include Western blot, immunoblot, enzyme-linked immunosorbant assay (ELISA), radioimmunoassay (RIA), immunoprecipitation, immunocytochemistry, immunohistochemistry, mass spectrometry, as well as methods to determine mRNA levels such as RT-PCR and northern analysis, real-time PCR, PCR, in situ hybridization and so on.

For example, a test compound may be added to a reaction mixture containing a purified BOC and a BOC ligand or a peptide fragment of a BOC ligand (e.g., Shh), and the binding between BOC and the BOC ligand is determined and compared to the binding when the mixture is incubated under similar conditions but without the test compound. A lower binding in the presence of the test compound is indicative that the test compound may be useful for inhibiting BOC activity and in turn for the prevention and/or treatment of cancer. The detection step (i.e. determination of the binding) could be monitored by any number of means including, but not limited to binding-dependent optical spectroscopy, fluorimetry, and radioactive label variation and could use various techniques such as Surface Plasmon resonance, FRET, yeast two hybrids, and alpha-screen.

Cell-based assays designed for identifying BOC inhibitors may comprise the addition of a test compound to cells stimulated by Shh and the determination of BOC expression and/or BOC activity observed when the cells are incubated under similar conditions but without the inhibitory compound. The detection step could be monitored by any number of means including by measuring cell proliferation (e.g., by MTT assay) or BOC downstream activation (e.g., expression of a gene (e.g., a reporter gene) operably linked to a transcription element normally associated with a gene whose expression is modulated by BOC activity (e.g., GLI-1)).

In another aspect, the present invention provides an agent that inhibits BOC expression or activity identified by the above-noted screening method.

Transgenic Non Human Mammal

As used herein, the terminology "transgenic non human mammal" refers to any non human mammal which harbors a nucleic acid sequence having been inserted into a cell and having become part of the genome of the mammal that develops from that cell. In one specific embodiment of the present invention, the genetic alteration of the transgenic non human mammal has been introduced in a germ-line cell, such that it enables the transfer of this genetic alteration to the offspring thereof. Such offspring, containing this genetic alteration are also transgenic non human mammals.

Techniques for the preparation of such transgenic mammals are well known in the art (e.g., a standard pronuclear microinjection; introduction of a transgene in embryonic stem (ES) cells; microinjecting the modified ES cells into blastocyst; or infecting a cell with a recombinant virus containing the transgene in its genome). Non-limiting examples of patents relating to a transgenic non human animal include U.S. Pat. Nos. 4,736,866; 5,087,571; 5,175,383; 5,175,384 and 5,175,385. Many animals may be used as host for the transgenes of the present invention, including all laboratory animals including mice, rats and rabbits. In a specific embodiment, the transgenic mammal is a mouse. In a more specific embodiment, the mouse strain is the C57BL/6J. Any other mouse strain however may be used in accordance with the present invention and identified as containing the BOC transgene. Other commonly used mouse strains for transgenic studies include C57Black, FVB, 129Sv, CD1 and ICR.

Diagnosis, Prognosis and Disease Monitoring Methods

The present inventors have shown in a mouse tumor model (medulloblastoma model) that BOC is overexpressed in 100% of medulloblastoma tumors analyzed compared to normal adjacent tissues, and thus that BOC may be used as a biological marker for the detection and characterization of tumors. Also, BOC overexpression was observed in preneoplasia, indicating that BOC is a marker of early stage invasive cancer and/or may be used to detect pre-malignant lesions.

The present inventors have also shown that BOC is expressed in human medulloblastoma tumor samples and that its high expression correlates with an increased risk for cancer progression.

Therefore, in another aspect, the invention relates to the diagnosis and prognostic of cancer, or of a susceptibility or predisposition to cancer. The invention thus provides a method for diagnosing cancer, or a predisposition to cancer, in a subject based on the expression and/or activity of BOC determined in a sample (e.g., a biopsy) from the subject. The expression and activity of BOC in the sample may be determined using the assays/methods described above.

In another aspect, the present invention provides a method for prognosis of a cancer patient, said method comprising: (a) determining the level and/or activity of BOC in a sample from said cancer patient, (b) comparing said level and/or activity to a corresponding reference level and/or activity; and (c) prognosing said cancer patient based on said comparison.

In another aspect, the present invention provides a method for prognosis of a cancer patient, said method comprising: (a) detecting an expression and/or activity of BOC in a sample (e.g., a tumor sample) from said cancer patient, and (b) prognosing said cancer patient based on said detection; wherein the detection (i.e., presence) of BOC expression and/or activity in said sample is indicative that said subject has a poor prognosis, and wherein the lack of detection (i.e., absence) of BOC expression and/or activity in said sample is indicative that said subject has a good prognosis.

In an embodiment, the above-mentioned prognosis is a good prognosis, wherein said good prognosis indicates that said individual has a high probability (e.g., at least 35%, 50%, 60%, 70% or 75%) of surviving after five, ten or fifteen years of initial diagnosis of cancer.

In an embodiment, the above-mentioned prognosis is a poor prognosis, and wherein said poor prognosis indicates that said individual has a low probability (e.g., less than 50% or 40%) of surviving after five, ten or fifteen years of initial diagnosis of cancer.

Poor prognosis may indicate that a tumor is relatively aggressive, while good prognosis may indicate that a tumor is relatively nonaggressive. Therefore, the invention provides for a method of determining a course of treatment of a cancer patient, comprising determining whether the level of expression of BOC correlates with the level of BOC expression in a reference sample representing a "good prognosis" expression level or a "poor prognosis" level; and determining a course of treatment, wherein if the expression correlates with the "poor prognosis" level, the tumor is treated as an aggressive tumor.

In another aspect, the present invention provides a method for performing a cancer follow-up or monitoring, for example to confirm the absence or removal of all tumor tissue following surgery, cancer chemotherapy and/or radiation therapy, or to monitor cancer chemotherapy and tumor reappearance. Such method comprising: (a) determining the expression and/or activity of BOC in a sample from said patient; (b) comparing said expression or activity to a corresponding expression and/or activity of BOC determined in a biological sample obtained from said patient at an earlier time (e.g., before surgery, just after surgery, at the start of treatment). For example, a decrease in said expression and/or activity relative to a corresponding expression and/or activity of BOC determined in a biological sample obtained from said patient at an earlier time (before surgery, at the start of treatment) is indicative that said patient is responsive to the treatment. Alternatively, an increase in BOC expression levels over time is indicative that the patient is not responsive to the treatment, or that this is a cancer recurrence (tumor reappearance).

In an embodiment, the method may comprise determining whether BOC activity and/or expression is modulated, e.g., upregulated or increased, relative to a control/reference activity or expression. In yet another embodiment, the control BOC expression or activity can be selected from an established standard, a corresponding BOC expression or activity determined in the subject (in a sample from the subject) at an earlier time; a corresponding BOC expression or activity determined in one or more control subject(s) known to not being predisposed to cancer, known to not having cancer, or known to have a good prognosis. In such cases, an increased or higher expression and/or activity in the sample from the subject relative to the control activity or expression is indicative that the subject has cancer, has a predisposition to cancer (e.g., has a higher risk of developing cancer and/or of experiencing cancer progression) or has a poor prognosis (e.g., lower survival probability, higher probability of cancer recurrence), while a comparable or lower expression or activity in a sample from the subject relative to the control expression or activity is indicative that the subject does not have cancer, is not predisposed to cancer or has a good prognosis (e.g., higher survival probability, lower probability of cancer recurrence).

In another embodiment, the reference/control BOC expression or activity is a corresponding expression or activity in a control subject known to have a predisposition to cancer, known to have cancer or known to have a poor prognosis. In such a case, a comparable or higher BOC expression and/or activity in a sample from the subject relative to the control expression or activity is indicative that the subject has cancer, has a predisposition to cancer or has a poor prognosis (e.g., lower survival probability, higher probability of cancer recurrence), while a lower expression or activity in a sample from the subject relative to the control expression or activity is indicative that the subject does not have cancer, is not predisposed to cancer or has a good prognosis (e.g., higher survival probability, lower probability of cancer recurrence).

In another embodiment, the reference/control BOC expression or activity is the average or median value obtained following determination of BOC expression or activity in a plurality of samples (e.g., samples obtained from several healthy and/or cancer patients).

BOC expression levels may in general be detected by either detecting mRNA from the cells and/or detecting expression products, such as polypeptides and proteins. Expression of the transcripts and/or proteins encoded by the nucleic acids described herein may be measured by any of a variety of known methods in the art. In general, the nucleic acid sequence of a nucleic acid molecule (e.g., DNA or RNA) in a sample can be detected by any suitable method or technique of measuring or detecting gene sequence or expression. Such methods include, but are not limited to, polymerase chain reaction (PCR), reverse transcriptase-PCR(RT-PCR), in situ PCR, SAGE, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization; and detection of a reporter gene.

Methods to measure protein expression levels of selected genes of this invention, include, but are not limited to: Western blot, tissue microarray, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence activated cell sorting (FACS), flow cytometry, and assays based on a property of the protein including but not limited to DNA binding, ligand binding, or interaction with other protein partners. In a further embodiment, the BOC expression level is measured by immunohistochemical staining, and the percentage and/or the intensity of immunostaining of immunoreactive cells in the sample is determined.

Methods for normalizing the level of expression of a gene are well known in the art. For example, the expression level of a gene of the present invention can be normalized on the basis of the relative ratio of the mRNA level of this gene to the mRNA level of a housekeeping gene, or the relative ratio of the protein level of the protein encoded by this gene to the protein level of the housekeeping protein, so that variations in the sample extraction efficiency among cells or tissues are reduced in the evaluation of the gene expression level. A "housekeeping gene" is a gene the expression of which is substantially the same from sample to sample or from tissue to tissue, or one that is relatively refractory to change in response to external stimuli. A housekeeping gene can be any RNA molecule other than that encoded by the gene of interest that will allow normalization of sample RNA or any other marker that can be used to normalize for the amount of total RNA added to each reaction. For example, the GAPDH gene, the G6PD gene, the actin gene, ribosomal RNA, 36B4 RNA, PGK1, RPLP0, or the like, may be used as a housekeeping gene.

Methods for calibrating the level of expression of a gene are well known in the art. For example, the expression of a gene can be calibrated using reference samples, which are commercially available. Examples of reference samples include, but are not limited to: Stratagene™ QPCR Human Reference Total RNA, Clontech™ Universal Reference Total RNA, and XpressRef™ Universal Reference Total RNA.

In an embodiment, the above-mentioned method comprises determining the level of a BOC nucleic acid (e.g., the nucleic acid of SEQ ID NO: 1) in the sample. In another embodiment, the above-mentioned method comprises determining the level of a BOC polypeptide (e.g., the polypeptide of SEQ ID NO: 2) in the sample. In an embodiment, the level of a BOC polypeptide is determined using an anti-BOC antibody. In a further embodiment, the anti-BOC antibody binds to the extracellular portion of BOC (e.g., the portion that is shedded from the cell surface in the extracellular fluid).

Alternatively, the above-mentioned diagnosis or prognosis may be performed based on the detection of BOC variants (e.g., the BOC variants described above), and more particularly BOC variants associated with either an increase or a decrease in BOC expression and/or activity. For example, the detection of a nucleic acid encoding a BOC variant (such as a nucleic acid comprising a polymorphism (e.g., SNP) in the coding region or a regulatory region) known to have increased BOC activity or known to provoke increased BOC expression in a sample from a subject may be used to determine that a subject has a cancer, is predisposed to (or at risk of developing) cancer, and/or has a poor cancer prognosis. Such BOC variants may be detected at the polypeptide or nucleic acid level using methods well known in the art, such as PCR-based methods as well as DNA sequencing, sequencing by hybridization, dot blotting, oligonucleotide array (DNA Chip) hybridization analysis and the like.

In an embodiment, the methods of diagnosis/prognostication noted above may be performed in conjunction with the therapeutic/prophylactic methods noted above, for preventing and/or treating cancer in a subject. Such a method thus comprises the diagnosis or prognostication of cancer in a subject and, in accordance with the diagnosis/prognosis, decreasing BOC levels in the subject (e.g., in a cell, tissue or organ of the subject) to prevent or treat cancer.

"Sample" or "biological sample" refers to any solid or liquid sample isolated from a live being. In a particular embodiment, it refers to any solid or liquid sample isolated from a human, such as a biopsy material, blood (e.g., plasma, serum or whole blood), saliva, synovial fluid, urine, amniotic fluid and cerebrospinal fluid. Such sample may be, for example, fresh, fixed (e.g., formalin-, alcohol- or acetone-fixed), paraffin-embedded or frozen prior to analysis of BOC expression level. In an embodiment, the above-mentioned sample is obtained from the central nervous system (e.g., a CNS cell, tissue or fluid). In a further embodiment, the CNS fluid is cerebrospinal fluid. In embodiments, the above-mentioned sample is a tumor cell/tissue sample (e.g., biopsy material).

The present invention also provides a kit or package comprising a reagent useful for determining BOC expression and activity (e.g., a ligand that specifically binds BOC polypeptide such as an anti-BOC antibody, or a ligand that specifically binds a BOC nucleic acid such as an oligonucleotide). Such kit may further comprise, for example, instructions for the prognosis and/or diagnosis of cancer, control samples, containers, reagents useful for performing the methods (e.g., buffers, enzymes), etc.

In an embodiment, the above-mentioned further comprises analyzing in the sample of the subject the activity and/or expression of at least another marker associated with medulloblastoma. Two main classes of medulloblastoma have been described, namely (a) medulloblastoma Shh generally associated with Gli1, Igf1, CXCR4, patch1 and/or sfrp1 expression and/or activity and (b) medulloblastoma Wnt, generally associated with tnc, epha4, Dkk1, Amhr2, and/or Emx2 expression and/or activity.

The above-mentioned methods may also be used for classifying or stratifying a subject into subgroups (based on BOC level and/or activity, for example or on a combination of BOC level and/or activity with that of another marker associated with medulloblastoma) having different phenotypes enabling a better characterization of cancer and eventually a better selection of treatment depending on the subgroup to which the subject belongs.

As used herein, a substantially similar level refers to a difference in the level of expression or activity between the level determined in a first sample (i.e. test sample) and the reference level which is about 10% or less; in a further embodiment, 5% or less; in a further embodiment, 2% or less.

As used herein, a "higher" or "increased" level refers to a level of expression or activity in a sample (i.e. test sample) which is at least 15% higher, in an embodiment at least 25% higher, in a further embodiment at least 40% higher; in a further embodiment at least 50% higher, in a further embodiment at least 100% higher (i.e. 2-fold), in a further embodiment at least 200% higher (i.e. 3-fold), in a further embodiment at least 300% higher (i.e. 4-fold), relative to the reference level (e.g., in a control sample, in corresponding normal adjacent tissue or alternatively, in the presence of an BOC inhibitor).

As used herein the term "subject" is meant to refer to any animal, such as a mammal including human, mice, rat, dog, cat, pig, cow, monkey, horse, etc. In a particular embodiment, it refers to a human.

A "subject in need thereof" or a "patient" in the context of the present invention is intended to include any subject that will benefit or that is likely to benefit from the decrease in the expression or activity of BOC. In an embodiment, a subject in need thereof is a subject diagnosed invasive disease overexpressing BOC.

As used herein, the term "a" or "the" means "at least one".

Although the present invention has been described hereinabove by way of specific embodiments thereof, it can be modified, without departing from the spirit and nature of the subject invention as defined in the appended claims.

The present invention is illustrated in further details by the following non-limiting examples.

Example 1

BOC is Involved in Cerebellum Development

Expression of BOC in GCP During the Cerebellum Development

Figure 3:
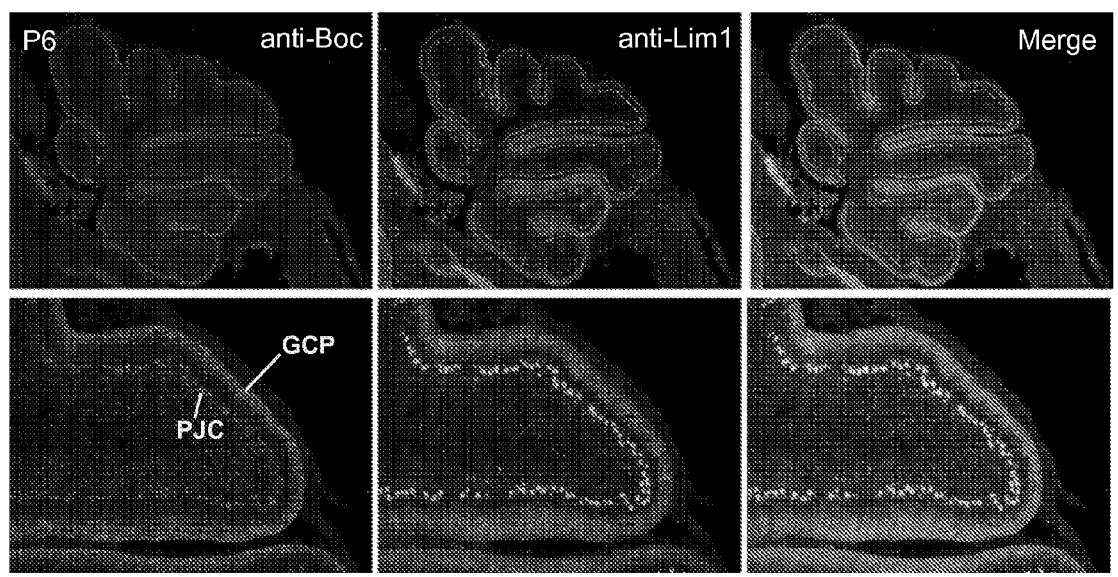
FIG. 3 shows the expression of BOC in a developing cerebellum as measured by immunohistochemistry using an anti-BOC antibody on sagittal cerebellum sections from post-natal day 6 mouse. Anti-Lim-1 is used to detect Lim1, a marker of Granule Cell Precursors (GCP) and Purkinje cells (PJC). In External germinal layer (EGL): proliferating Granule Cell Precursors co-express BOC and Lim1 (right panels)
Figure 4A:
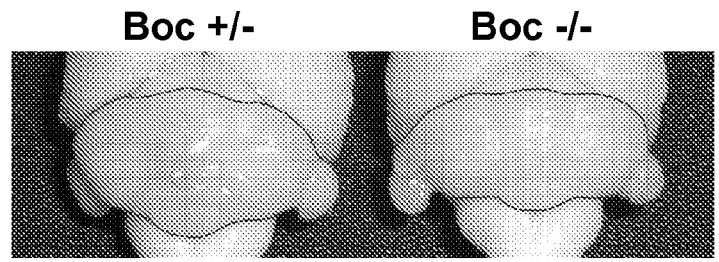
FIG. 4 shows a cerebellum analysis of $BOC^{-/-}$ mice compared to control $BOC^{+/-}$ mice. Photographs compare $BOC^{-/-}{}_{31}$ mice and control $BOC^{-/-31}$ whole cerebellums (FIG. 4A) and cerebellum cross sections (FIG. 4B). Measurements of cerebellum weight (FIG. 4C) and cerebellum surfaces on brain sections (FIG. 4D) revealed that $BOC^{-/-}$ animals have a smaller cerebellum than control mice.
Figure 4B:
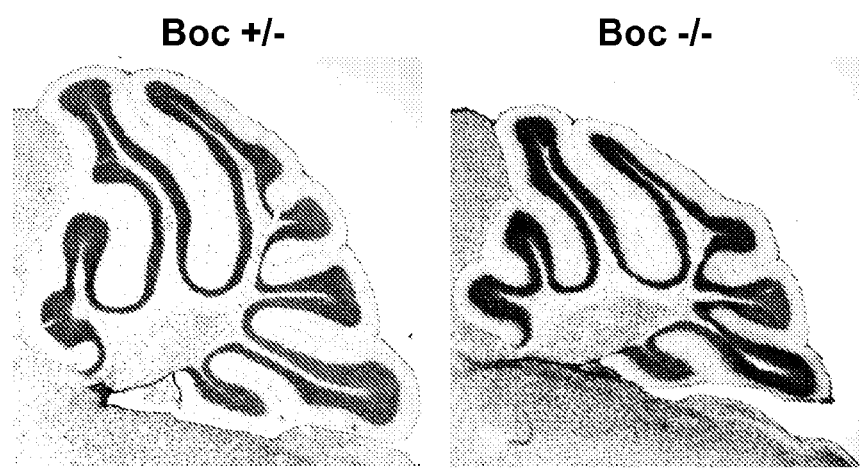
Figure 4C:
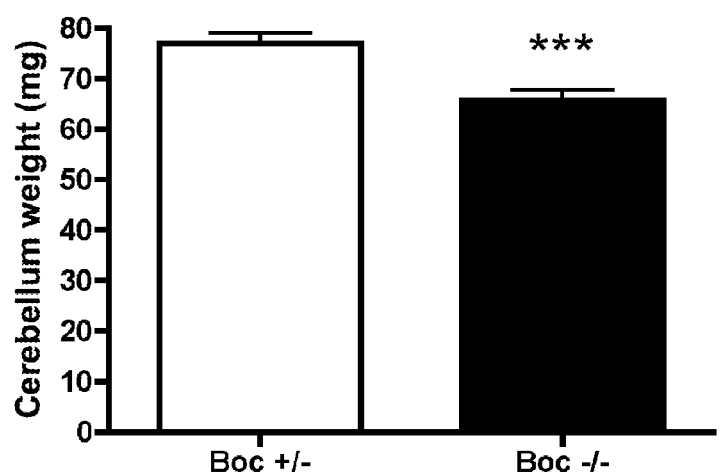
Figure 4D:
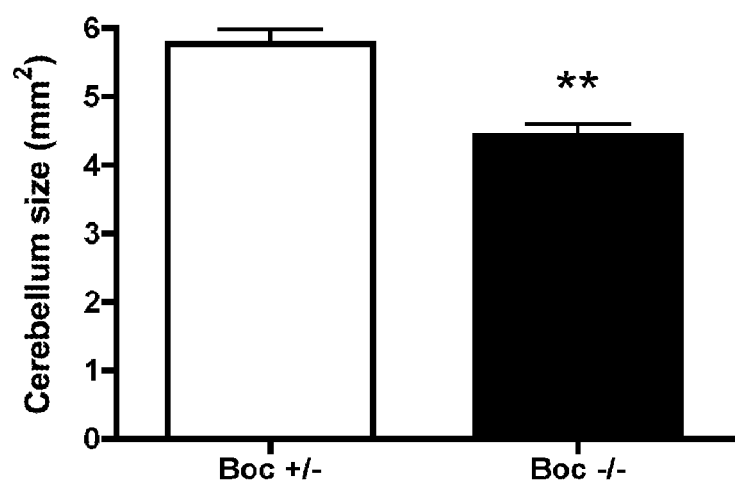

To explore the involvement of BOC in the cerebellum development, its expression was first examined through mouse cerebellum histological sections. Immunohistochemistry on sections of wild-type mice cerebelli showed a distribution of BOC labeling in the Granule Cell Precursors (GCP) (FIG. 3). BOC is expressed in proliferating GCP whereas CDON is not expressed in the cerebellum.

BOC$^{-/-}$ Mice Cerebellum Shows Less Cell Proliferation

Comparative analyses of size and weight of cerebellum from mice harbouring different BOC alleles were performed. Measurements have shown that mice completely lacking BOC gene (BOC$^{-/-}$ mice obtained from Dr S. K. McConnell at University of Stanford) possess significantly smaller cerebelli, both in term of weight and size, as compared to heterozygote BOC$^{+/-}$ or wild-type (BOC$^{+/+}$) control groups (FIG. 4).

Figure 5A:
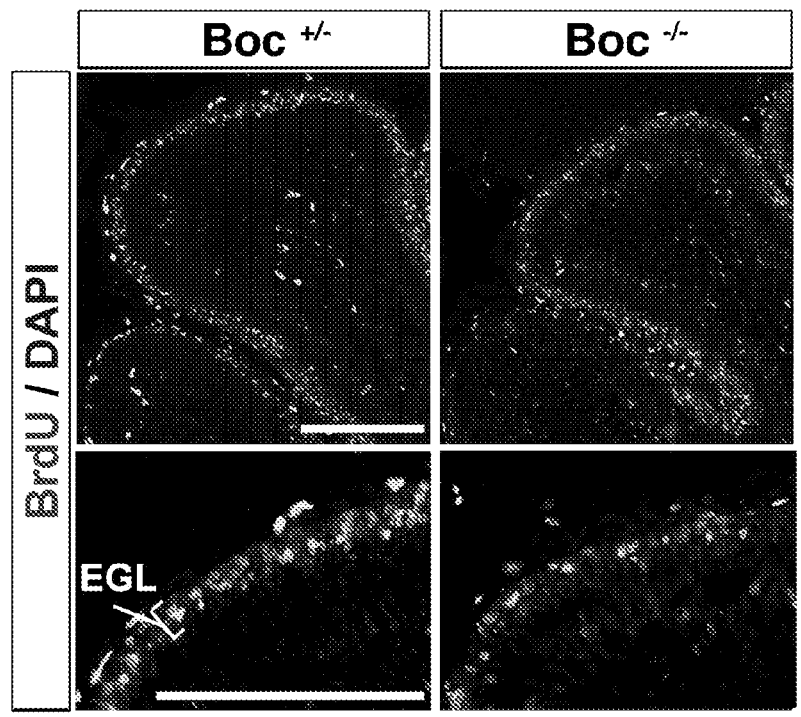
FIG. 5 shows apoptosis and proliferation measurements in developing cerebellum of $BOC^{-/-}$ and $BOC^{+/-}$ control mice at post-natal day 3. Cell proliferation was evaluated by BrdU incorporation (FIGS. 5A and 5B) and by immunostaining using the proliferation marker phosphohistone H3 (PhH3) (FIG. 5C) and apoptosis, by TUNEL assay (FIGS. 5D and 5E). No difference in the total number of apoptotic nuclei on matching cerebellum sections were observed between $BOC^{-/-}$ and $BOC^{+/-}$ animals (FIG. 5E). However, $BOC^{-/-}$ mice show a significant decrease in number of BrdU+ (FIG. 5B) and PhH3+ cells (FIG. 5C) in external granular layer, indicating a diminished proliferation compared to control $BOC^{+/-}$ mice. EGL: external germinal layer.
Figure 5B:
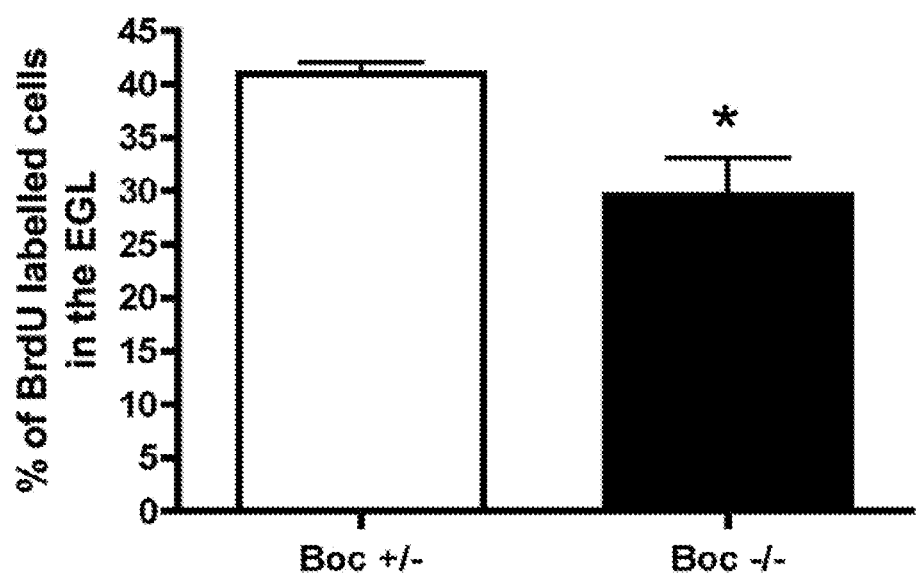
Figure 5C:
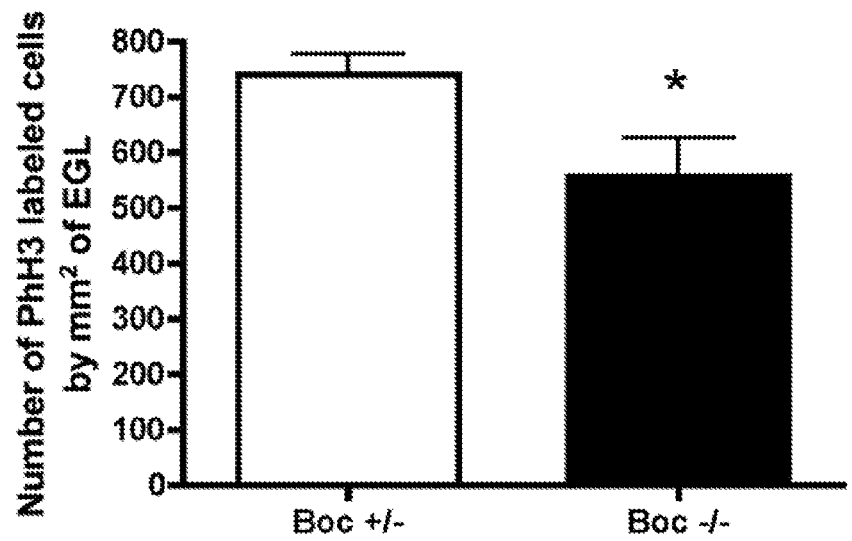

The reduction in size of BOC$^{-/-}$ cerebellum could be due either to a decrease in cell proliferation or to an increase of apoptosis. Sections of cerebellum obtained from BOC$^{-/-}$ and BOC$^{+/-}$ mice were analyzed and compared. GCP proliferation in the EGL was measured by immunostaining using an antibody specific for different cell proliferation markers such as phospho-histone H3 (PhH3) and BrdU. BOC$^{-/-}$ mouse cerebelli exhibited a significant decrease in the number of BrdU-positive cells as compared to control BOC$^{+/-}$ mice (FIGS. 5A and 5B). Similar results were obtained with another marker of cell proliferation, phospho-histone H3 (phH3) staining (FIG. 5C).

Figure 5D:
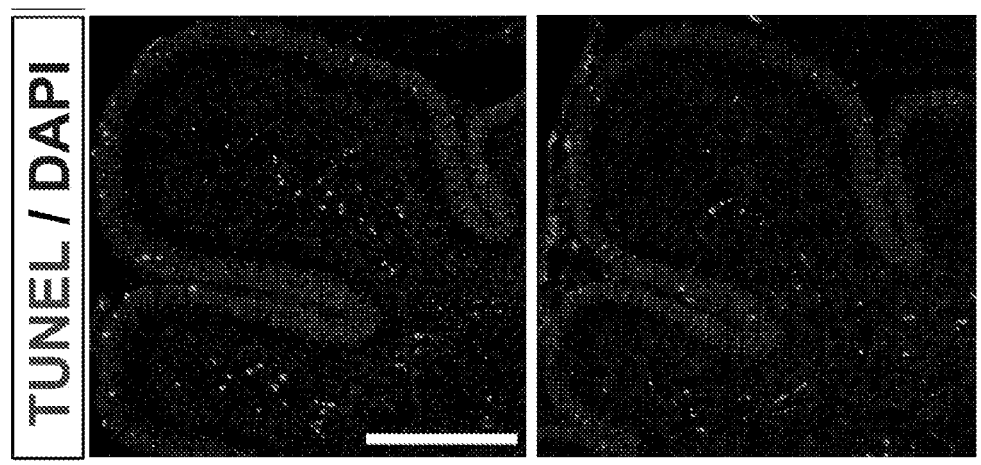
Figure 5E:
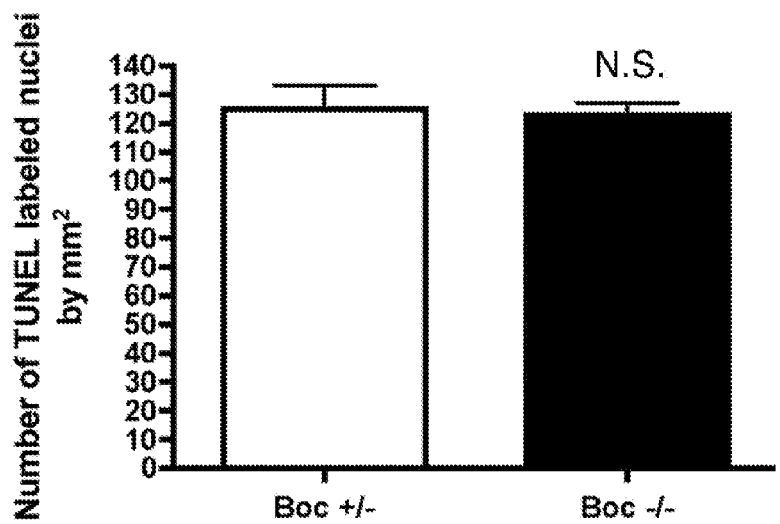

To measure the number of apoptotic cells, cerebellum sections obtained from BOC$^{-/-}$ and BOC$^{+/-}$ mice were stained with a marker of apoptosis, TUNEL (Terminal deoxynucleotidyl transferase dUTP nick end labeling) to detect DNA fragmentation. TUNEL-positive nuclei were counted on a series of cerebellum matching sections. No difference was observed in the number of TUNEL-positive cells on cerebellum sections of BOC$^{-/-}$ and BOC$^{+/-}$ mice (FIGS. 5D and 5E). The decrease in size of the cerebellum of BOC$^{-/-}$ mice is thus correlated with a decrease in cell proliferation of GCP.

Loss of BOC in GCP: Cell Autonomous Decrease of Cell Proliferation

Figure 6:
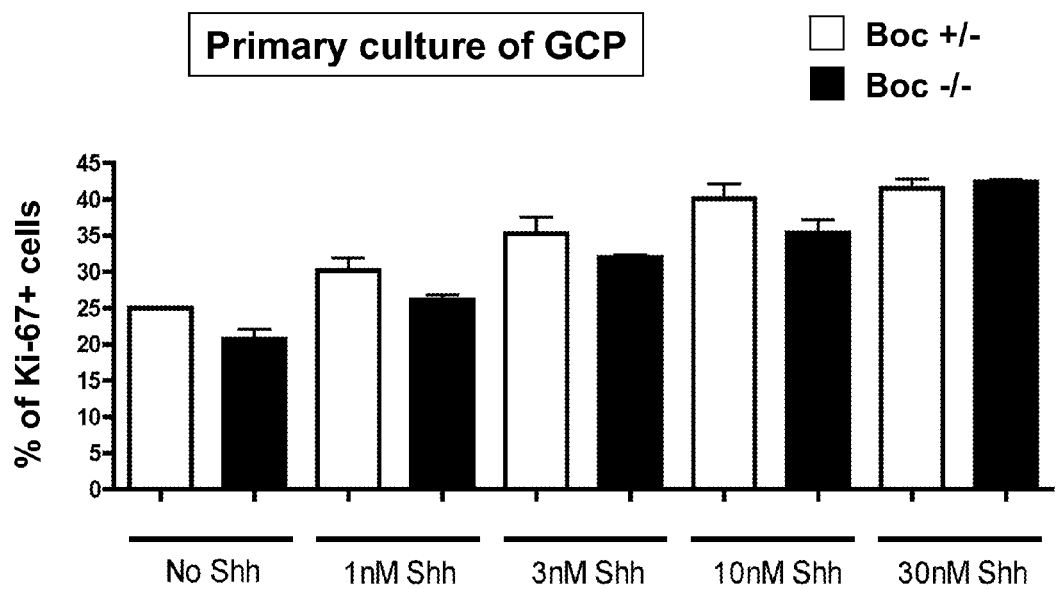
FIG. 6 shows a graph illustrating the cell autonomous decrease of GCP proliferation in the absence of BOC. The GCP derived from cerebellum of $BOC^{-/-}$ and $BOC^{+/-}$ mice were cultured in vitro in the presence of increasing concentration of Shh as indicated. The percentage of Ki-67 positive cells from 2 experiments was then measured and compared. While Boc null GCPs still respond to Shh stimulation, their proliferative response remains lower than wild type GCPs. Note that at high Shh doses, no difference is observed between $BOC^{+/-}$ and $BOC^{-/-}$ GCPs.

GCP purified from the cerebellum of both BOC$^{-/-}$ and BOC$^{+/-}$ mice were cultured in vitro in the presence of increasing concentrations of Shh before labeling with an anti-Ki-67 (Ki-67 protein is present during all active phases of the cell cycle ($G_1$, S, $G_2$, and mitosis), but is absent from resting cells ($G_0$), and is thus an excellent marker to determine the fraction of proliferating cells in a given cell population). GCP were extracted from newborn mice from post-natal age day 3 to 5. Cerebelli were dissected, chopped into small pieces and treated with trypsin. Cells were then dissociated using fire polished pipettes and spin in a 35%-65% Percoll™ gradient. Pure GCP were then collected at the 35%-65% Percoll™ interface and plated in a pre-coated PDL-coated dish. GCP were then treated with different concentrations of Shh and cultured for 48 h before being fixed and processed for Ki-67 immunostaining. Finally, the proportion of Ki-67-positive cell was analyzed. In the absence of Shh, the percentage of Ki-67-positive GCP cells was significantly reduced in GCP cells derived from BOC$^{-/-}$ mice as compared to those derived from BOC$^{+/-}$ mice (FIG. 6). In both cultures, increasing the concentration of Shh resulted in a dose-dependent increase in the number of Ki-67-positive cells. However, at 1 nM, 3 nM and 10 nM, a significant difference is still observed between GCP derived from BOC$^{-/-}$ and GCP derived from BOC$^{+/-}$ mice. These data show a cell autonomous decrease of GCP proliferation in the absence of BOC.

BOC Overexpression Increases GCP Proliferation in the Presence of Shh

Figure 7:
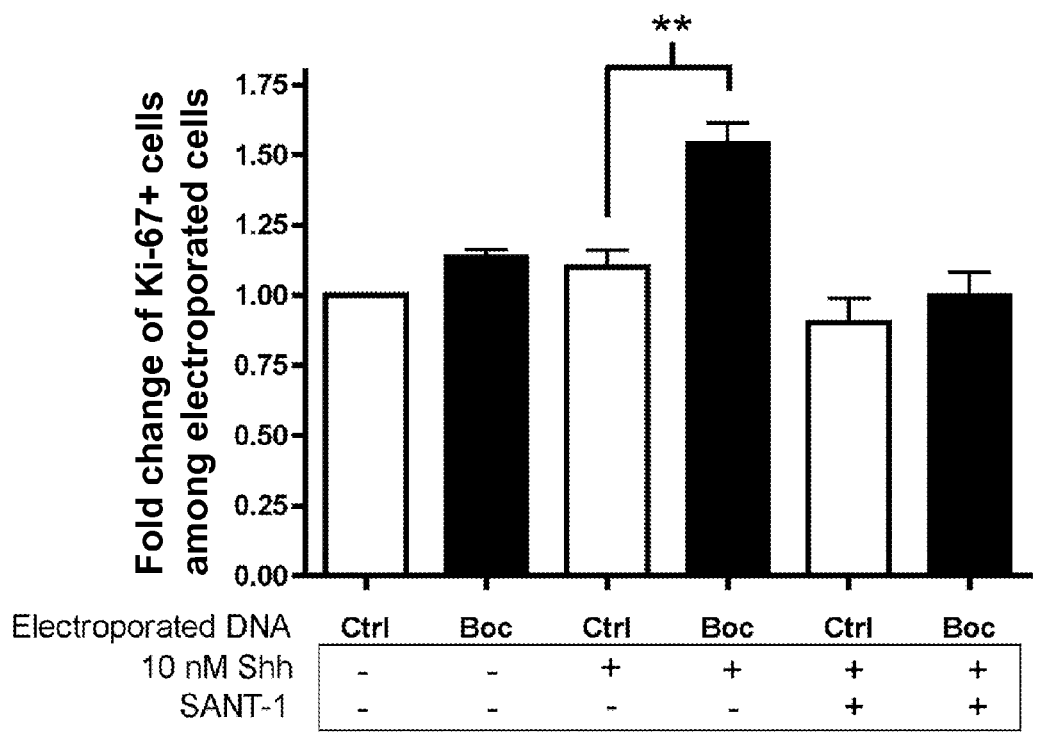
FIG. 7 shows a graph illustrating the Shh-dependent effect of overexpression of BOC on cell proliferation. GCP purified from post-natal day 4 rat cerebellum were co-electroporated with either a combination of BOC with a red fluorescence protein expressing plasmids (BOC) or with a control empty plasmid with a red fluorescence protein expressing plasmid (control). Proliferation was evaluated by measuring the percentage of Ki-67 positive cells among electroporated cells in absence or in presence of sonic hedgehog (Shh) and also in presence of Shh in combination with an inhibitor of Smo (SANT-1)

GCP purified from post-natal day 4 rat cerebellum were co-electroporated with either a combination of a plasmid containing a nucleic acid encoding murine BOC with a red fluorescent protein (RFP)-expressing plasmids (BOC) (both genes under the control of the chicken beta-actin promoter) or with a control empty plasmid with a red fluorescent protein-expressing plasmid (control). Proliferation was evaluated by measuring the percentage of Ki-67-positive cells among electroporated cells in the presence or absence of Shh. In addition, the role of the Hh signalling protein Smoothened (Smo) was tested using an inhibitor of Smo (SANT-1) in combination with Shh. The percentage of Ki-67-positive cells stimulated by the presence of 10 nM of Shh was markedly increased in GCP overexpressing BOC as compared to control electroporated cells treated in parallel (FIG. 7). The addition of SANT-1 prevents this increase, suggesting that Smo plays a role in the BOC-mediated increase in cell proliferation.

Example 2

Detection of BOC in Medulloblastoma

The Ptc1$^{+/-}$ Mouse Medulloblastoma Animal Model

Figure 8A:
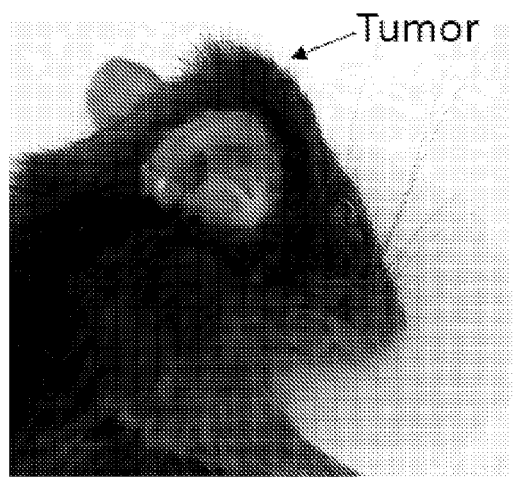
FIG. 8A shows a mouse having a medulloblastoma tumor. Cerebellum sections showing the presence of a medulloblastoma tumor (FIG. 8B, right panel) compared to normal cerebellum (FIG. 8B, middle panel).
Figure 8B:
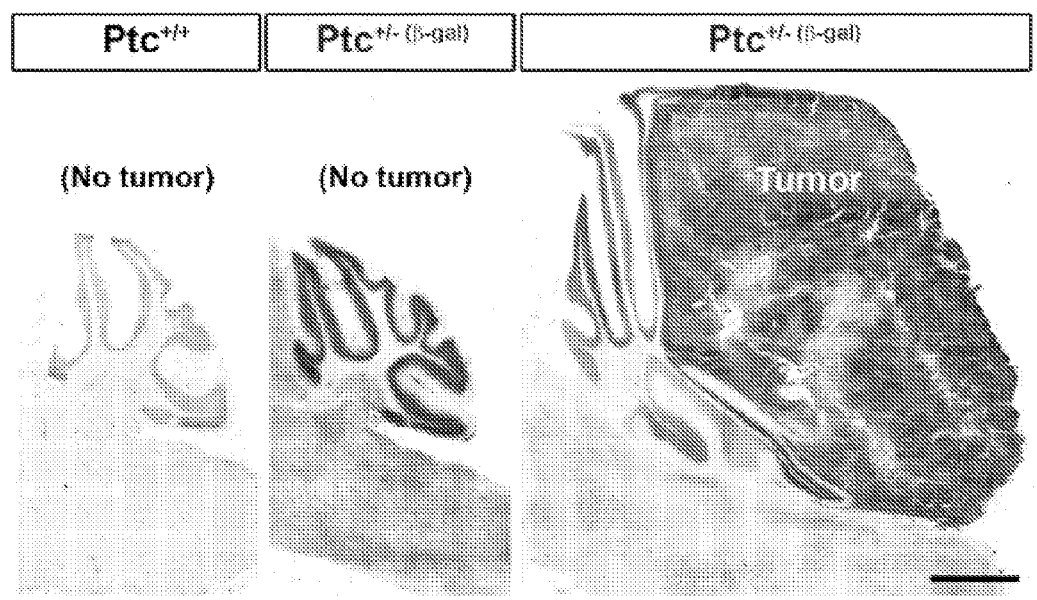
FIG. 8 presents the murine $Ptc1^{+/-}$ medulloblastoma model.
FIG. 8C: Survival curves, $Ptc1^{+/-}$: n=41, $Ptc1^{+/+}$: n=21.
Figure 8C:
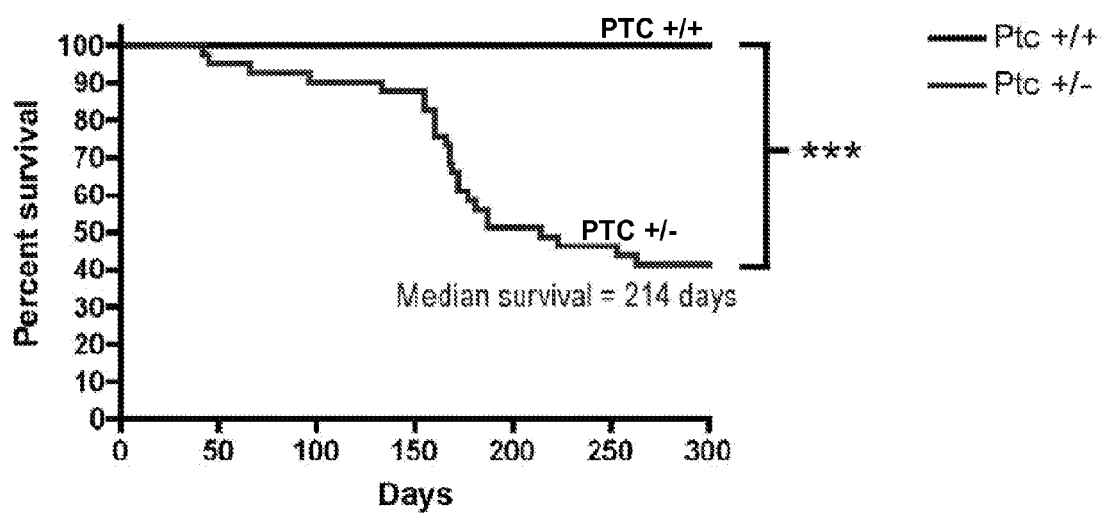

Activation of Sonic hedgehog signaling normally regulates granule cell precursor proliferation during cerebellum development. In humans, germline mutations of the Shh receptor gene PATCHED (PTCH) predispose to medulloblastoma. Mice with heterozygous patched mutation (Ptc1$^{+/-}$) also develop medulloblastoma tumors (Goodrich et al., 1997, *Science* 277(5329):1109-13). Survival analysis of Ptc1$^{+/-}$ mice revealed that about 55% of these mice developed large medulloblastoma tumor and generally died at about 6 months of age (FIG. 8).

BOC is Expressed in Mouse Medulloblastoma Tumors

Figure 9A:
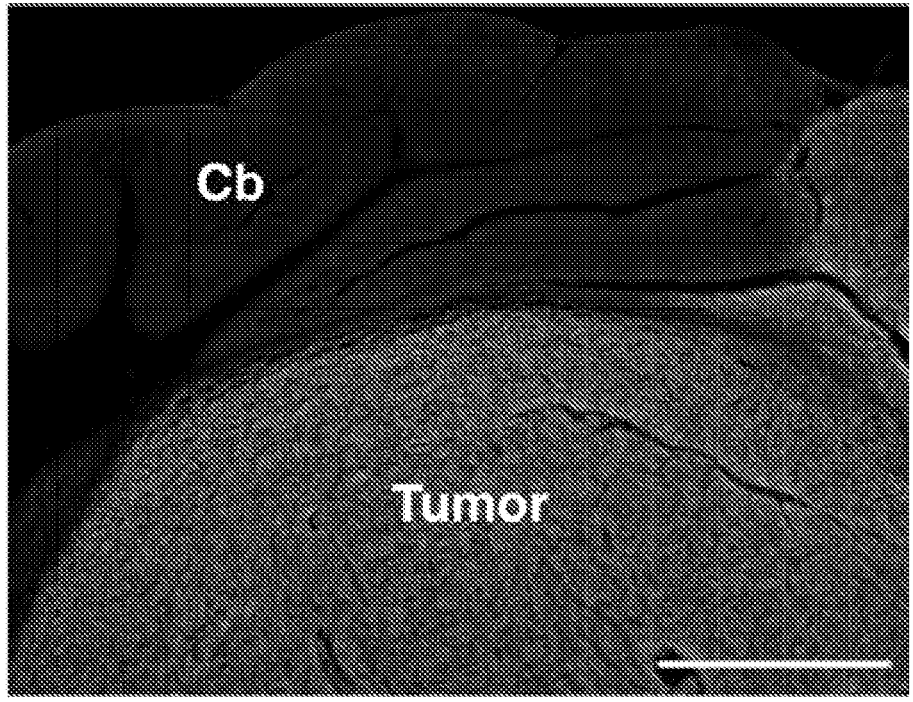
FIG. 9A shows BOC immunostaining on a medulloblastoma tumor using anti-BOC antibodies and showing that BOC is highly expressed in tumor tissue as compared to adjacent normal cerebellum (Cb).
Figure 9B:
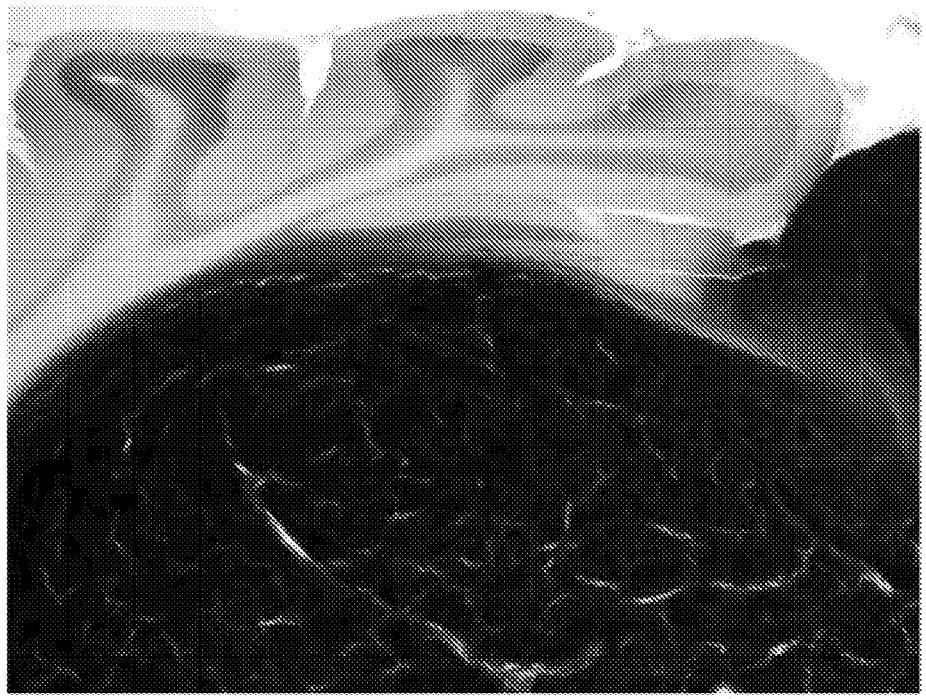
FIG. 9B shows BOC-promoter driven alkaline phosphatase (PLAP) reporter gene expression on an adjacent section of the same tumor. Note that BOC mutant mice were generated by targeting BOC with a genetrap cassette encoding β-galactosidase-neomycin fusion (β-gal) and human placental alkaline phosphatase (PLAP) reporter genes with the use of the 'targeted trapping' method (Friedel et al., 2005. Proc Natl Acad Sci USA 102: 13188-13193).
Figure 9C:
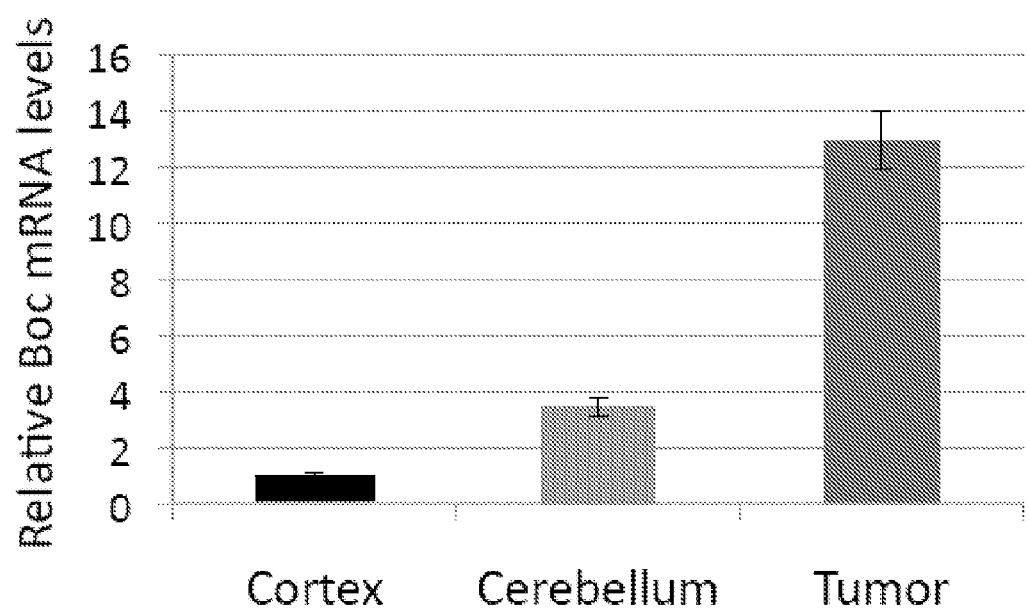
FIG. 9C shows BOC mRNA levels in cortex (left bar), normal cerebellum (middle bar) and medulloblastoma tumor (right bar) as measured by quantitative PCR.

Using the Ptc1$^{+/-}$ mouse model, double-mutant mice in which one or both BOC alleles have been deleted were generated. BOC-promoter driven alkaline phosphatase (PLAP) reporter gene expression and BOC immunostaining using anti-BOC antibodies (R&D Systems, Minneapolis, Minn., USA), in a medulloblastoma tumor obtained from the Ptc$^{+/-}$/BOC$^{+/-}$ mouse. FIG. 9A shows BOC immunostaining on a medulloblastoma tumor using anti-BOC antibodies and showing that BOC is highly expressed in tumor tissue as compared to adjacent normal cerebellum (Cb). FIGS. 9B and C shows BOC-promoter driven alkaline phosphatase (PLAP) reporter gene expression on an adjacent section of the same tumor. FIG. 9C shows BOC mRNA levels in cortex (left bar), normal cerebellum (middle bar) and medulloblastoma tumor (right bar) as measured by quantitative PCR. BOC is thus overexpressed in tumor tissue as compared to adjacent normal cerebellum (FIGS. 9A-9C), at both the protein and mRNA levels.

Figure 11:
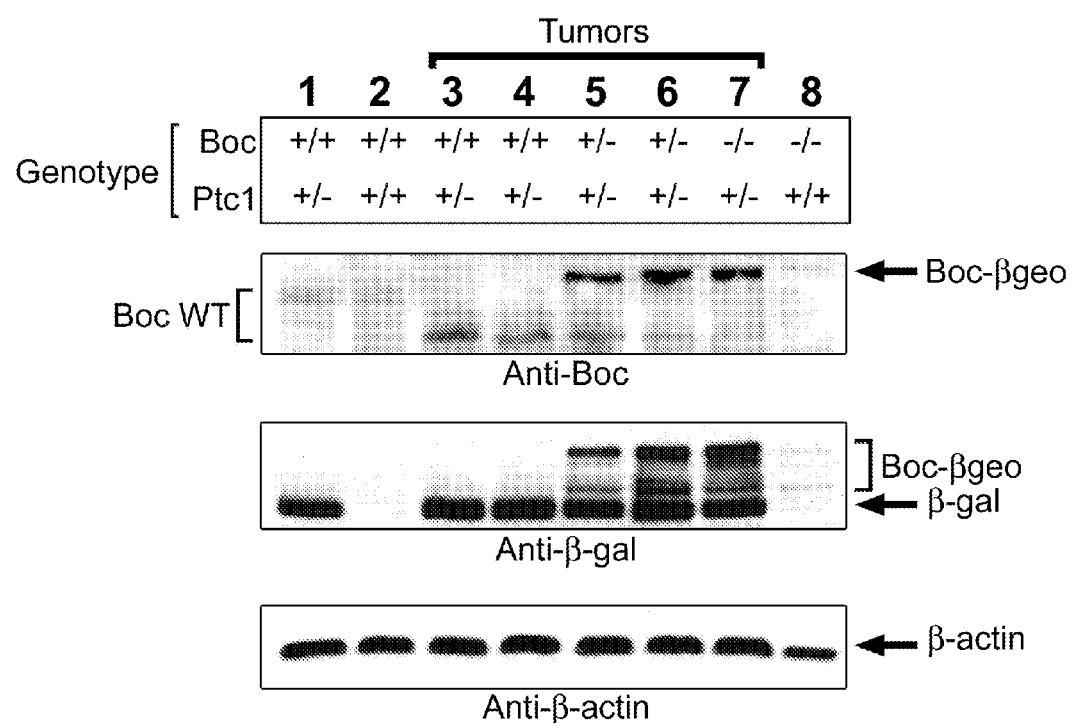
FIG. 11 shows BOC protein level in normal adult mice cerebellum and in medulloblastoma tumors. BOC was detected by western blotting on 100 μg of total protein extracts. Medulloblastoma tumors (lanes 3-7) and normal cerebellum (lanes 1, 2 and 8) were obtained from $BOC^{+/+}$; $Ptc1^{+/-}$, $BOC^{+/+}$; $Ptc1^{+/-}$, $BOC^{+/-}$; $Ptc1^{+/-}$, $BOC^{-/-}$; $Ptc1^{+/-}$ and $BOC^{-/-}$; $Ptc1^{+/+}$ mice as indicated. Anti-BOC antibody detects two major bands, corresponding to wild-type BOC and the mutant chimeric form of BOC (Boc-βgeo), respectively. Note that BOC mutant mice were generated by targeting BOC with a genetrap cassette encoding a β-galactosidase-neomycin fusion (βgeo) and human placental alkaline phosphatase (PLAP) reporter genes with the use of the 'targeted trapping' method (Friedel et al., 2005, supra). Ptc1-deficient mice were generated by replacing a part of exon 1 and exon 2 of the Ptc1 gene by the LacZ gene, so as to generate a chimeric Ptc protein. An anti-βgal antibody was used to confirm the specificity of the bands detected by anti-BOC.

This observation was further confirmed by Western blot analysis of total proteins purified from medulloblastoma tumors derived from different mouse genotypes (FIG. 11). These data show that BOC is a good marker of medulloblastoma tumors. The increase in BOC protein expression correlates with an increase of the reporter gene PLAP (placental alkaline phosphatase, knocked into the BOC gene). Therefore, an increase in BOC expression at both the protein and nucleic acid levels was observed in medulloblastoma tumors.

BOC in Overexpressed in Preneoplasia

Figure 10:
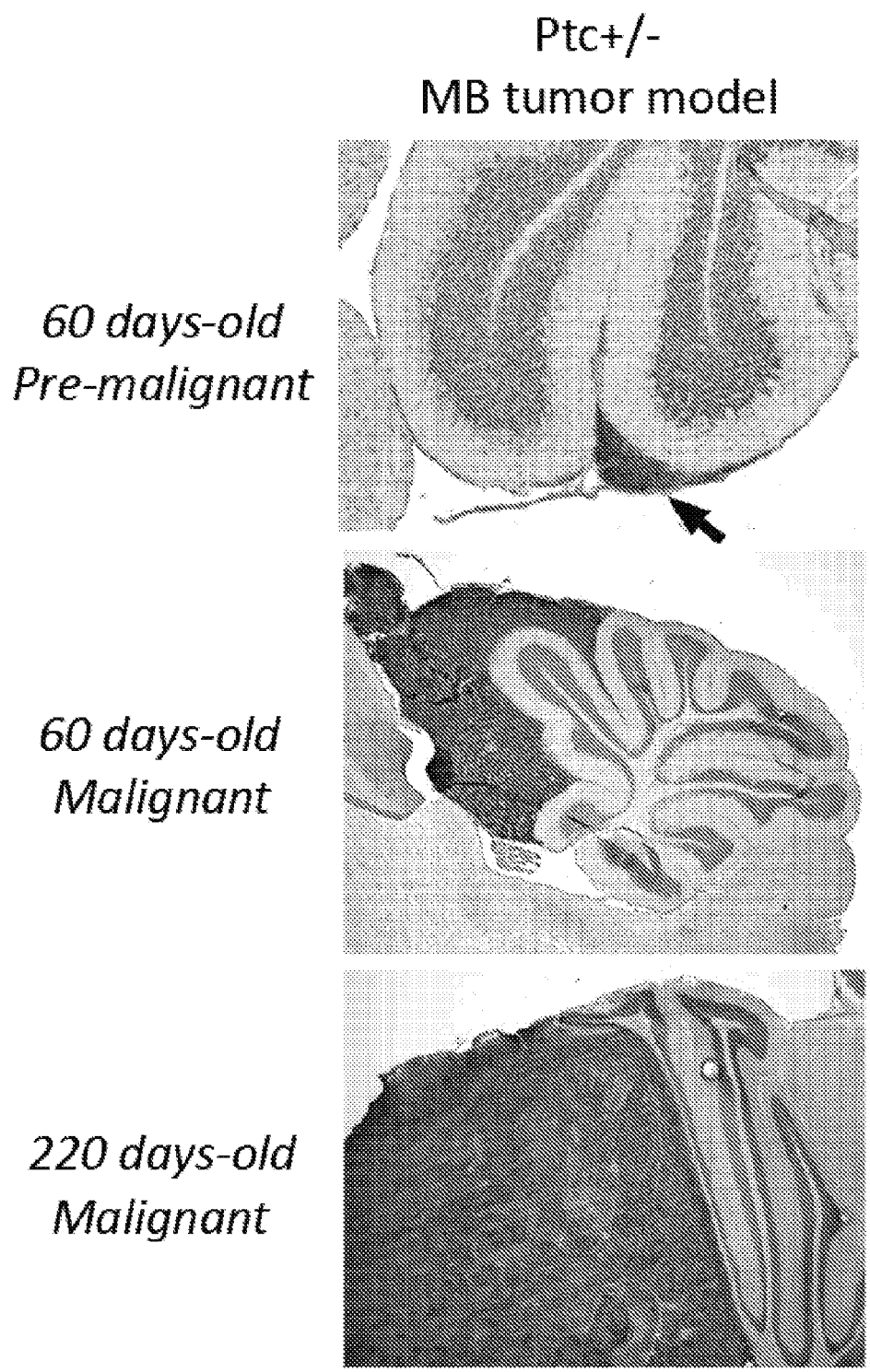
FIG. 10 shows BOC expression in the $Ptc^{+/-}$ medulloblastoma mice model. BOC is highly expressed in pre-malignant and malignant mouse medulloblastoma tumors. Anti-BOC immunohistochemistry on sections presenting different medulloblastoma malignancy stages, namely pre-malignant (upper panel), 60 days-old malignant (middle panel) and 220 days-old malignant (lower panel). All Ptc+/− mice develop premalignant lesions, but only 50% of the mice will develop malignant tumors (Oliver et al., Development 2005, 132: 2425)

While about 55% of Ptc1$^{+/-}$ mice develop medulloblastoma at 3 to 6 months of age, most of them have regions of ectopic cell in their cerebellum at 8 weeks of age (P60). These cells have been described as remnants of the external germinal layer (EGL) and have been reported to represent a preneoplastic stage of tumorigenesis. Immunostaining using an anti-BOC antibody applied on cerebellum section of P60 Ptc1$^{+/-}$ mice revealed that BOC is also highly expressed in all of these pre-neoplasia (FIG. 10, upper panel). BOC therefore represents a marker at early stage of medulloblastoma tumors.

Example 3

BOC is Associated with the Development of Medulloblastoma Tumors

BOC is Involved in Medulloblastoma Tumorigenesis

Figure 12:
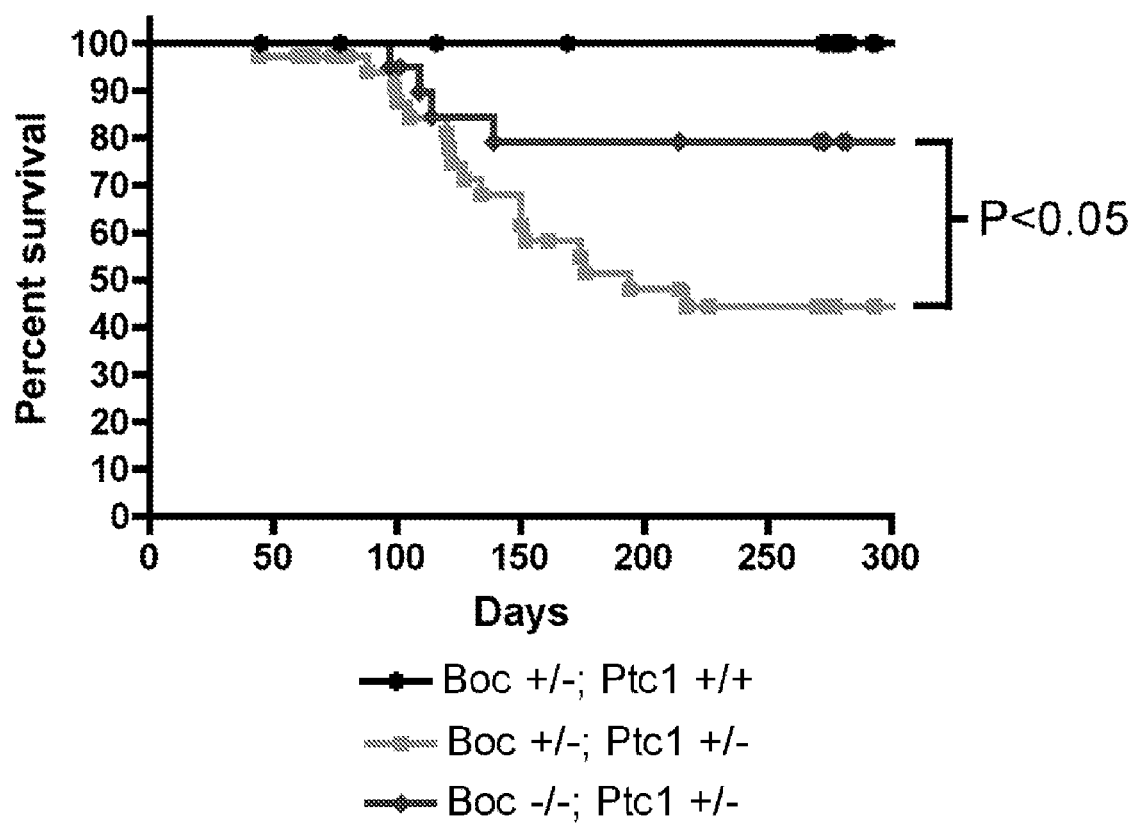
FIG. 12 shows a graph of the survival of mice harboring different combinations of BOC and Ptc1 alleles. Survival analyses were performed on $BOC^{+/-}$; $Ptc1^{+/-}$ (n=36, circles), $BOC^{+/-}$; $Ptc1^{+/-}$ (n=35, squares), and $BOC^{-/-}$; $Ptc1^{+/-}$ mice (n=21, diamonds). The absence of BOC is associated with an increase in survival.

Survival analyses were performed on BOC$^{-/-}$; Ptc1$^{+/-}$ mice and compared to BOC$^{+/-}$; Ptc1$^{+/-}$ and BOC$^{+/-}$; Ptc1$^{+/-}$ mice. In both groups of Ptc1$^{+/-}$ mice, the percentage of survival was significantly reduced as compared to that observed in Ptc1$^{+/+}$ mice (FIG. 12). However, a higher survival was observed in Ptc1$^{+/-}$ mice having an homozygous deletion of BOC (BOC) as compared to their heterozygous counterparts (BOC$^{+/-}$) (FIG. 12).

Overexpression of BOC In Vivo Using Retroviral Infection of GCP

Retroviral vector-mediated delivery of cDNA to mice in vivo is an effective way to overexpress a gene in animals. Using this approach, BOC is overexpressed in GCP of young rats. The virus is administrated by stereotaxic injection directly in developing cerebellum to infect dividing GCP cells, which are the most numerous proliferating cell type in developing cerebellum. The development of medulloblastoma tumors is analyzed in these mice and compared to that of control mice (infected with a control retroviral vector).

Inhibition of BOC Expression in Mouse and Human Medulloblastoma-Derived Cell Lines Inhibition of BOC expression in medulloblastoma-derived cell lines is performed using different RNA interfering (RNAi) compounds. Ptc1$^{+/-}$ (derived from Ptc1$^{+/-}$ mice medulloblastoma), Daoy (human), UW2 (human) and UW3 (human) cell lines are transfected with one of the 4 shRNA constructs. These shRNA are designed to include a hairpin of 21 base pair sense and antisense stem and a 6 base pair loop. Each hairpin sequence is cloned into the lentiviral vector (pLKO.1) and the sequence is verified (Seq B9: CCCAT-GAGAACAGACCAAGAT (SEQ ID NO: 5); Seq B10: CCCGTATACTATGGTGCCATT (SEQ ID NO: 6); Seq B11: CGACATTAAGATGCAGTGCTT (SEQ ID NO: 7); Seq C1: GAGGGAAACACAGCAGTCATT (SEQ ID NO: 8); Seq B12: CCTCTACAATGTCCAGGTGTT (SEQ ID NO: 9)); These multiple constructs are created to ensure adequate coverage of the BOC gene. Stable cell lines may be selected using the puromycin selectable marker. The efficiency of each shRNA is verified by Q-PCR. The effect of the inhibition of BOC is then measured by using a MTT Cell Proliferation Assay. The MTT [3-(4,5-dimethylthiazol-2-yl)-2,5-diphenyltetrazolium bromide] cell proliferation assay, first described by Mosmann (*J. Immunol. Methods*. 1983, 65(1-2): 55-63, incorporated by reference in its entirety) is based on the ability of active mitochondrial reductase enzymes from viable cells to cleave the tetrazolium rings of the pale yellow MTT. The cleavage reaction forms a purple formazan crystals which is largely impermeable to cell membranes resulting in its accumulation within healthy cells. Solubilization of the cells by addition of a detergent liberates and solubilizes the formazan crystals. The number of surviving cells is directly proportional to the level of the formazan product created. The color can then be quantified spectrophotometrically. The production of purple formazan in cells treated with a compound is measured relative to the production in control cells, and dose-response curves can be generated. This assay measures the cell proliferation rate and conversely, when metabolic events lead to apoptosis or necrosis, the reduction in cell viability, thus also allowing the evaluation of the cytotoxicity of tested compounds. The effect of the inhibition of BOC by the different shRNA constructs is tested in the Ptc1$^{+/-}$, Daoy, UW2 and UW3 cell lines using the MTT Cell Proliferation Assay.

The shRNAs inhibiting cell proliferation are compounds that inhibit expression of BOC. These compounds could serve as a basis for the development of a drug for preventing and/or treating cancer, such as medulloblastoma.

Example 4

BOC in Human Tumors

BOC is Overexpressed in Human Medulloblastoma

Figure 13A:
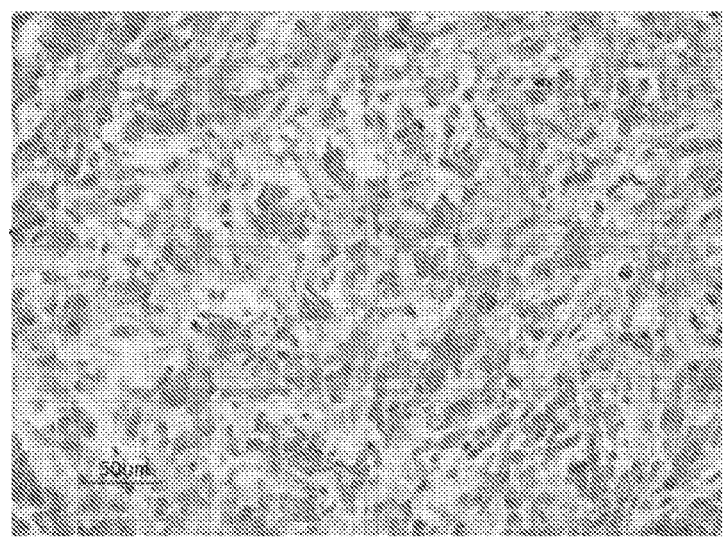
FIG. 13 shows a tissues microarray analysis of different human medulloblastoma tumors. Slides containing thin sections of 73 human medulloblastoma tissue samples were immunostained with anti-BOC antibody. Example of BOC-positive (FIG. 13A) and BOC-negative (FIG. 13B) tumor tissues are presented.
FIG. 13C shows a table summarizing the statistical analysis obtained from the tissues microarray analysis of 73 human medulloblastoma tumors.
Figures 13B, 13C:
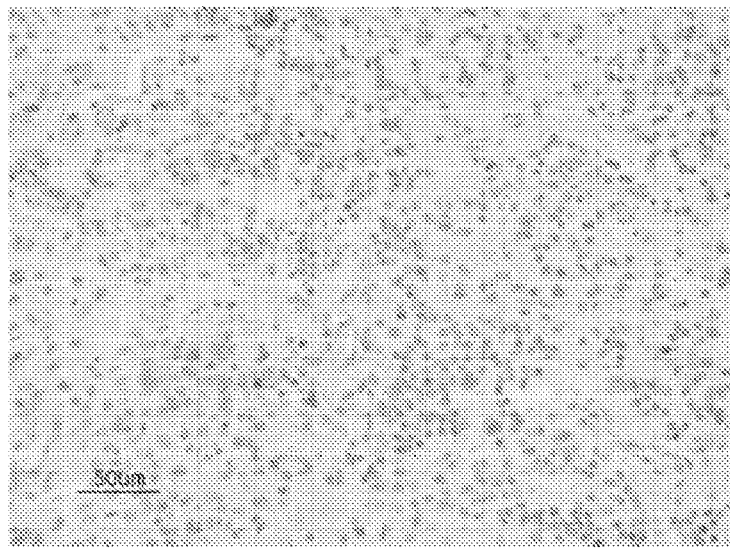

A tissue microarray was constructed from 73 different human medulloblastoma tumor samples, as well as from positive and negative control samples (Ray A. et al., *Clin Cancer Res*. 2004. 10(22): 7613-20). For each patient, all pathological blocks and corresponding slides were obtained and reviewed by neuropathology for diagnostic accuracy and tissue adequacy. Representative tumor areas were identified, and between three and four cores were obtained for each tumor. Clinical data collected for each patient included age and metastatic disease status at presentation, sex, extent of surgical resection, chemotherapy use, radiotherapy use, progression-free survival, and overall survival. The latter was the primary end point for this study. Metastatic disease was defined as either the presence of malignant cells on cerebrospinal fluid (CSF) cytology (obtained between 7 and 14 days after surgery) or definite radiographic evidence of spread before the onset of chemotherapy or radiotherapy. Equivocal CSF specimens were considered positive if the next follow-up CSF sample within 2 weeks was cytologically positive. Clumping of spinal roots on magnetic resonance imaging was not considered positive. The arrays were assayed for immunohistochemical expression of BOC (representative examples of immunohistochemical stainings are illustrated at FIG. 13A (positive BOC staining) and FIG. 13B (negative BOC staining), and results analyzed for correlation between BOC expression and the factors listed above (e.g., sex, survival). FIG. 13C summarized the data obtained, which revealed that 38 tumors out of the 73 analyzed (~52%) were positive for BOC expression.

A higher level of BOC in tissue microarray from human tumor samples as compared to that in a reference sample is indicative that modulation of BOC expression/activity may be useful for the treatment of medulloblastoma.

Tumor samples are also tested by tissues microarray with a series of antibodies for measuring the level of others markers characterizing medulloblastoma (e.g., Ptc, Shh, Gli-1, Igf1, CXCR4, sfrp1, tnc, epha4, Dkk1, Amhr2, Emx2). Statistical analyses also include characteristics such as age, sex, therapeutic treatment, presence of metastasis and survival of the patient.

Figure 19:
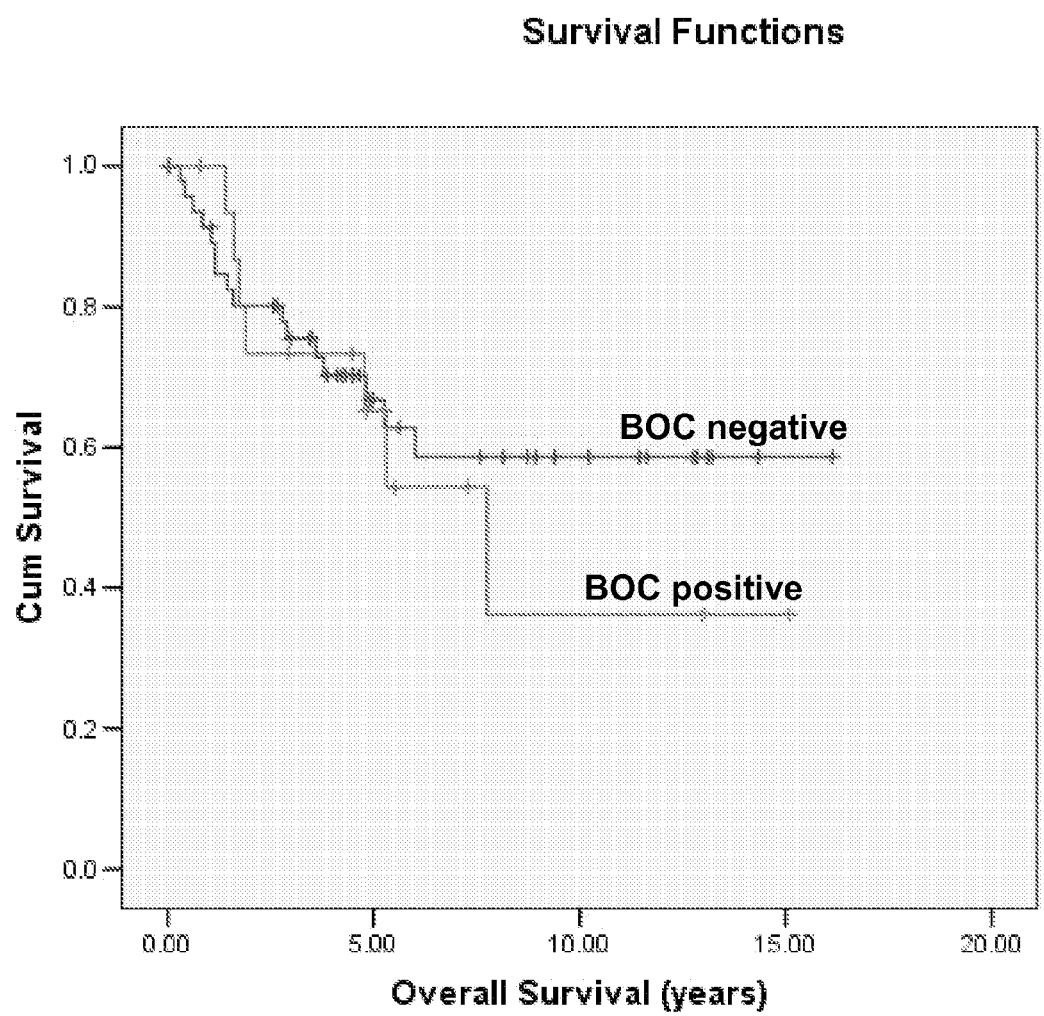
FIG. 19 shows a correlation between survival and BOC expression in human medulloblastoma samples (n=66). Patients having BOC positive medulloblastoma tumors have a worse prognosis than those having BOC negative tumors.

Survival correlation analysis indicated that patients with medulloblastoma tumors positive for BOC have a tendency to show a lower overall survival probability over years than patients with BOC negative tumors (FIG. 19). These results indicate that the presence of tumors expressing BOC correlates with a worse prognosis for some patients.

BOC Expression and Gene Profiling for Human Medulloblastoma Classification

Figures 14A, 14B:
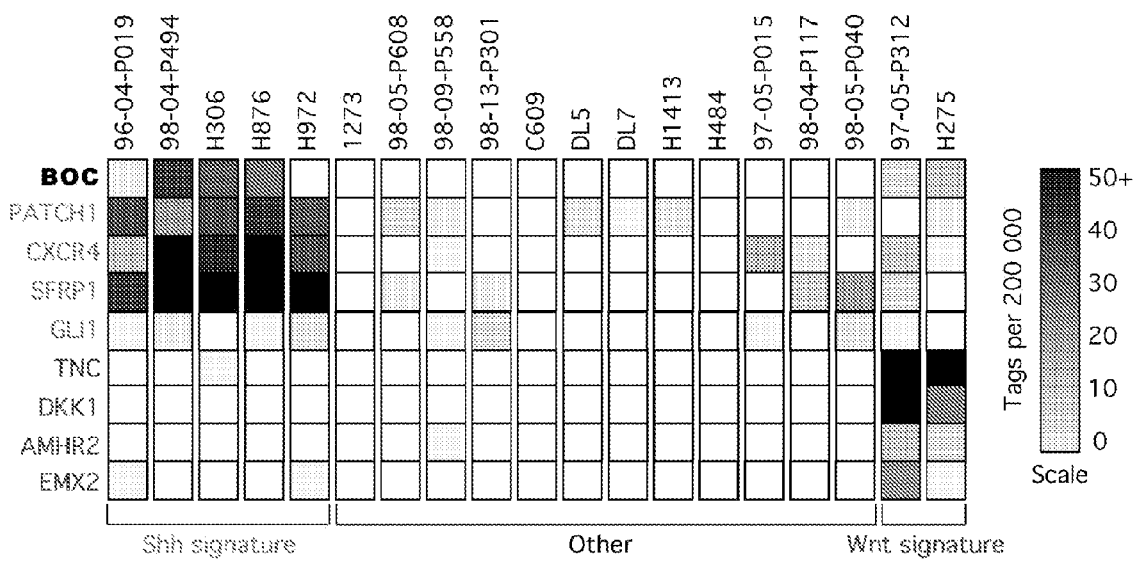
FIG. 14B shows a table summarizing the expression of BOC in Shh and Wnt medulloblastoma tumors.

Analysis of BOC expression in a variety of human medulloblastoma tissue samples was performed by Serial Analysis of Gene Expression (SAGE) using the available database of the Cancer Genome Anatomy Project (Lash A E et al., 2000. *Genome Res*, 10(7): 1051-1060). Overexpression of BOC was reported in six medulloblastoma among 19 samples (about 32%) (FIGS. 14A and B). The analysis was also performed for markers characterizing medulloblastoma Shh (e.g., Gli1, Igf1, CXCR4, Ptc1, sfrp1) and markers for medulloblastoma Wnt (e.g., tnc, epha4, Dkk1, Amhr2, Emx2). Data analysis revealed that BOC was overexpressed in 80% (4/5) of medulloblastoma Shh and 100% (2/2) of medulloblastoma Wnt (FIG. 14B).

BOC Expression in Various Human Cancers

Analysis of BOC expression in a variety of human tumor tissue samples was also performed by SAGE. As shown in Tables II and III below, overexpression of BOC was detected in several tumor tissues including brain ependynoma, ovary tumor, medulloblastoma, breast tumor, skin tumor, glioblastoma, meningioma, astrocytoma, chondrosarcoma, colon adenocarcinoma, liver cholangiocarcinoma, prostate carcinoma, bladder tumor, lung tumor, lymph node lymphoma, vascular endothelium hemangioma, kidney carcinoma and thyroid follicular adenoma.

TABLE II

SAGE analysis of BOC expression in tumor tissue libraries

| SAGE Library | Total Tags in library | Tag counts | Tag per 200,000 |
|---|---|---|---|
| Brain ependymoma B R353 | 73822 | 30 | 81 |
| Ovary adenocarcinoma B OVT-8 | 31987 | 10 | 62 |
| Brain ependymoma B 239 | 46653 | 12 | 51 |
| Brain medulloblastoma B 98-04-P494 | 43068 | 9 | 41 |
| Brain medulloblastoma B H306 | 60454 | 10 | 33 |
| Brain medulloblastoma B H876 | 67404 | 10 | 29 |
| Breast fibroadenoma MD | 55688 | 8 | 28 |
| Ovary carcinoma CL A2780 | 21369 | 3 | 28 |
| Brain ependymoma B R1023 | 122690 | 17 | 27 |
| Breast carcinoma B BWHT18 | 50701 | 6 | 23 |
| Skin Normal B hs0277 | 5269789 | 587 | 22 |
| Skin Cancer B hs0279 | 5703298 | 610 | 21 |

TABLE II-continued

SAGE analysis of BOC expression in tumor tissue libraries

| SAGE Library | Total Tags in library | Tag counts | Tag per 200,000 |
|---|---|---|---|
| Uterus normal B hs0195 | 3718463 | 373 | 20 |
| Brain ependymoma B R510 | 120431 | 12 | 49 |
| Breast carcinoma associated myofibroblast CD10+ AP IDC7 | 65091 | 6 | 18 |
| Breast carcinoma associated myoepithelium AP DCIS6 | 81452 | 7 | 17 |
| Brain ependymoma B R510 | 84073 | 7 | 16 |
| Skin Normal B hs0272 | 4397550 | 339 | 15 |
| Foreskin Normal B hs0305 | 3940350 | 279 | 14 |
| Brain ependymoma B R512 | 75379 | 5 | 13 |
| Brain glioblastoma B GBM1062 | 59762 | 4 | 13 |
| Brain medulloblastoma B H275 | 72318 | 5 | 13 |
| Breast carcinoma associated myofibroblast CD10+ AP T392303 | 73967 | 5 | 13 |
| Breast normal myoepithelium AP myoepithelial1 | 57222 | 4 | 13 |
| Brain meningioma grade II B SF2366 | 48711 | 3 | 12 |
| Skin Normal B hs0271 | 5807686 | 368 | 12 |
| Skin Normal B hs0278 | 3042221 | 190 | 12 |
| Brain ependymoma B R580 | 68614 | 4 | 11 |
| Eye lens B UIH10 | 85898 | 5 | 11 |
| Brain astrocytoma grade I B H1043 | 75922 | 4 | 10 |
| Brain meningioma grade III B SF2366 | 59786 | 3 | 10 |
| Brain glioblastoma control CL H247 | 60428 | 3 | 9 |
| GallBladder Normal B HN | 85706 | 4 | 9 |
| Pancrease normal B 1 | 21520 | 1 | 9 |
| Uterus Normal B hs0194 | 6452623 | 312 | 9 |
| Brain medulloblastoma B 97-05-P312 | 74295 | 3 | 8 |
| Brain meningioma grade I B 5F4271 | 69253 | 3 | 8 |
| Brain normal thalamus B 1 | 24015 | 1 | 8 |
| Skin Normal B hs0282 | 4411636 | 180 | 8 |
| Brain astrocytoma grade III B 407 | 108312 | 4 | 7 |
| Brain astrocytoma grade III B 584 | 103008 | 4 | 7 |
| Brain ependymoma B 1394 | 56314 | 2 | 7 |
| Brain ependymoma B R455 | 51825 | 2 | 7 |
| Brain ependymoma B R582 | 52189 | 2 | 7 |
| Brain fetal normal B 51 | 305546 | 12 | 7 |
| Brain glioblastoma control B pooled | 56428 | 2 | 7 |
| Brain glioblastoma CL 28d | 110624 | 4 | 7 |
| Breast carcinoma associated stroma B DCIS6 | 57049 | 2 | 7 |
| Breast carcinoma epithelium CD44+ AP PE2 | 52342 | 2 | 7 |
| Breast normal epithelium CD44+ AP N1 | 56008 | 2 | 7 |
| Breast normal stroma AP 1 | 79152 | 3 | 7 |
| Breast normal stroma B IDC8 | 50485 | 2 | 7 |
| Cartilage chondrosarcoma grade 2 CL UIFUO | 75019 | 3 | 7 |
| Cartilage dedifferentiated chondrosarcoma metastasis CL UIGPO | 108319 | 4 | 7 |
| Esophagus normal B CN01 | 75634 | 3 | 7 |
| Peritoneum normal B 13 | 53527 | 2 | 7 |
| Skin Normal B hs0281 | 6517089 | 243 | 7 |
| Spinal cord normal B 1 | 54785 | 2 | 7 |
| Vascular endothelium normal breast associated AP 1 | 57023 | 2 | 7 |
| Brain astrocytoma grade III B 828 | 99939 | 3 | 6 |
| Brain ependymoma B 1150 | 62373 | 2 | 6 |
| Brain glioblastoma CL 4d | 115212 | 4 | 6 |
| Breast carcinoma B IDC-4 | 64095 | 2 | 6 |
| Breast carcinoma associated myofibroblast CD10+ AP T112603 | 63539 | 2 | 6 |
| Breast normal myoepithelium CD10+ AP N15 | 63994 | 2 | 6 |
| Brain astrocytoma grade III B 439 | 107824 | 3 | 5 |
| Brain astrocytoma grade III B R927 | 107344 | 3 | 5 |
| Brain astrocytoma grade II B H516 | 108116 | 3 | 5 |
| Brain astrocytoma grade II B H518 | 116022 | 3 | 5 |
| Brain astrocytoma grade II B H530 | 102439 | 3 | 5 |
| Brain glioblastoma B H1110 | 68986 | 2 | 5 |
| Brain glioblastoma CL stem cells | 108414 | 3 | 5 |
| Brain glioblastoma hypoxia CL H247 | 71765 | 2 | 5 |
| Breast carcinoma B 95-259 | 39364 | 1 | 5 |
| Breast carcinoma B IDC-3 | 68891 | 2 | 5 |

TABLE II-continued

SAGE analysis of BOC expression in tumor tissue libraries

| SAGE Library | Total Tags in library | Tag counts | Tag per 200,000 |
|---|---|---|---|
| Breast carcinoma myoepithelium X ITGB6+ AP | 78785 | 2 | 5 |
| Breast normal FS NER | 34565 | 1 | 5 |
| Breast normal myoepithelium AP IDC7 | 69006 | 2 | 5 |
| Breast normal myoepithelium CD10+ AP N5 | 76173 | 2 | 5 |
| Skin Melanoma B hs0275 | 4128221 | 110 | 5 |
| Skin normal B NS | 36615 | 1 | 5 |
| Brain astrocytoma grade III B H272 | 96059 | 2 | 4 |
| Brain astrocytoma grade II B H501 | 128309 | 3 | 4 |
| Brain glioblastoma B H1425C | 88990 | 2 | 4 |
| Brain normal cerebellum B BB542 | 40500 | 1 | 4 |
| Breast carcinoma MD DCIS | 40783 | 1 | 4 |
| Breast normal epithelium AP 1 | 48729 | 1 | 4 |
| Breast normal epithelium CD24+ AP N1 | 41551 | 1 | 4 |
| Leukocytes normal B 1 | 47873 | 1 | 4 |
| Ovary adenocarcinoma B OVT-6 | 41443 | 1 | 4 |
| Retinal Pigment Epithelium normal B 4PeriRPE | 90199 | 2 | 4 |
| Skin cancer B hs0283 | 3692239 | 74 | 4 |
| Brain astrocytoma grade III B H1055 | 109886 | 2 | 3 |
| Brain astrocytoma grade III B R140 | 118733 | 2 | 3 |
| Brain glioblastoma B R20 | 101053 | 2 | 3 |
| Brain glioblastoma CL H54,EGFRvIII | 56982 | 1 | 3 |
| Brain medulloblastoma B 96-04-P019 | 52645 | 1 | 3 |
| Brain meningioma grade I B SF4465 | 54647 | 1 | 3 |
| Breast carcinoma B IDC-5 | 60451 | 1 | 3 |
| Breast carcinoma epithelium CD44+ AP ASC3 | 52478 | 1 | 3 |
| Breast normal epithelium AP Br N | 50512 | 1 | 3 |
| Breast normal organoid B | 58181 | 1 | 3 |
| Colon adenocarcinoma CL HCT116 | 55641 | 1 | 3 |
| Embryonic stem cell H13 normal p22 CL SHE15 | 221101 | 4 | 3 |
| Liver cholangiocarcinoma B K1 | 60319 | 1 | 3 |
| Prostate carcinoma CL LNCaP | 60250 | 1 | 3 |
| Prostate normal B 2 | 64058 | 1 | 3 |
| Prostate normal MD PR317 | 59277 | 1 | 3 |
| Retina Pigment Epithelium normal B 1 | 53666 | 1 | 3 |
| Thyroid normal B 001 | 115938 | 2 | 3 |
| Vascular normal Cs control | 51642 | 1 | 3 |
| White blood cells monocyte depleted mononuclear cells normal AP P1 | 51634 | 1 | 3 |
| Bone marrow normal AP CD34+/CD38+/lin+ | 81595 | 1 | 2 |
| Brain medulloblastoma CL UW228-N | 94937 | 1 | 2 |
| Brain astrocytoma grade II B H563 | 88568 | 1 | 2 |
| Brain normal leptomeninges B AL2 | 72473 | 1 | 2 |
| Breast carcinoma MD LCIS | 67834 | 1 | 2 |
| Breast carcinoma associated stroma B IDC7 | 68024 | 1 | 2 |
| Breast carcinoma epithelium AP DCIS6 | 72857 | 1 | 2 |
| Breast carcinoma epithelium AP IDC7 | 73410 | 1 | 2 |
| Breast carcinoma epithelium X MUC1+ AP | 75147 | 1 | 2 |
| Breast normal epithelium CD24+ AP N5 | 76469 | 1 | 2 |
| Embryonic stem cell H9 normal p38 CL SHES2 | 401432 | 6 | 2 |
| Embryonic stem cell HSF6 normal p50 CL SHES9 | 224488 | 3 | 2 |
| GallBladder adenocarcinoma B HAIIb | 66988 | 1 | 2 |
| Heart normal B 1 | 83063 | 1 | 2 |
| Lung normal B 1 | 88708 | 1 | 2 |
| Lung tumor associated chronic inflammation B UihMO | 98962 | 1 | 2 |
| Lymph Node Lymphoma B 1 | 72008 | 1 | 2 |
| Ovary endometriosis CL E12 | 76097 | 1 | 2 |
| Skin cancer B hs0280 | 3618498 | 48 | 2 |
| Vascular endothelium hemangioma B 146 | 75680 | 1 | 2 |
| Bladder cancer B hs0241 | 3335801 | 17 | 1 |
| Brain astrocytoma grade III B H970 | 106982 | 1 | 1 |
| Brain astrocytoma grade II B H127 | 114489 | 1 | 1 |
| Embryonic stem cell H14 normal p22 CL SHE14 | 212170 | 2 | 1 |
| Embryonic stem cell H9 normal p38 CL SHES1 | 151735 | 1 | 1 |
| Kidney carcinoma B D2 | 100281 | 1 | 1 |
| Retina Macula normal B 4Mac | 101417 | 1 | 1 |
| Retina Peripheral normal B 2 | 105312 | 1 | 1 |
| Retina macula normal B HMAC2 | 102417 | 1 | 1 |
| Retina normal B 4cRet | 103701 | 1 | 1 |
| Skin cancer B has0284 | 3892507 | 38 | 1 |
| Thyroid follicular adenoma B TT005 | 101578 | 1 | 1 |

TABLE III

Summary of BOC expression in tumor tissues

| Organ/Tissue | Tumor type | # of Boc positive |
|---|---|---|
| Brain | Brain ependynoma | 11 |
|  | Glioblastoma | 11 |
|  | Meningioma | 4 |
|  | Astrocytoma | 16 |
| Ovary | Ovary carcinoma | 1 |
|  | Ovary endometriosis | 1 |
|  | Ovary adenocarcinoma | 2 |
| Breast | Breast fibroadenoma | 1 |
|  | Breast carcinoma | 19 |
| Skin | Skin cancer | 4 |
|  | Skin melanoma | 1 |
| Liver | Liver cholangiocarcinoma | 1 |
| Prostate | Prostate carcinoma | 1 |
| Bladder | Bladder adenocarcinoma | 1 |
|  | Bladder cancer | 1 |
| Lung | Lung tumor | 1 |
| Lymph node | Lymph node lymphoma | 1 |
| Vascular endothelium | Vascular endothelium hemangioma | 1 |
| Kidney | Kidney carcinoma | 1 |
| Thyroid gland | Thyroid follicular adenoma | 1 |

Example 5

Detection of BOC Protein by Enzyme-Linked Immunosorbant Assay (ELISA)

Figure 20A:
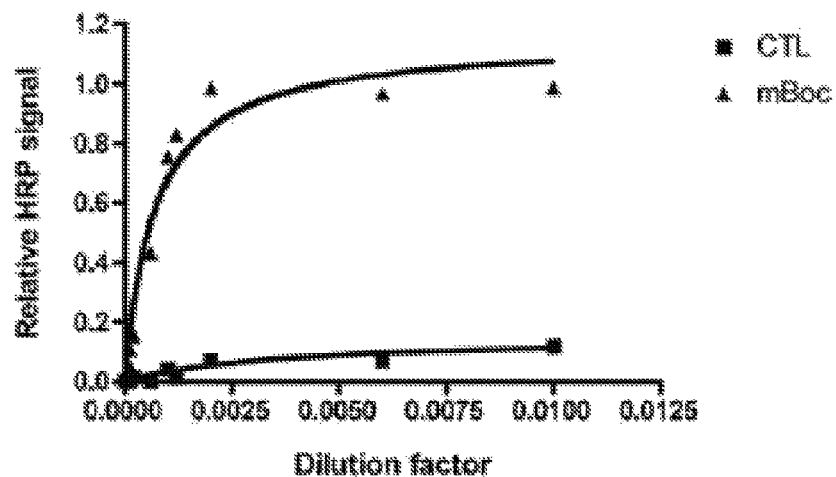
FIG. 20 shows direct ELISA performed with anti-BOC antibodies for detection. The anti-BOC antibodies recognize either the cytoplasmic tail of BOC (FIG. 20A) or its extracellular portion (FIG. 20B). ELISA quantifications were performed on extracts of COS7 cells transfected with a control plasmid (CTL, squares) or mouse BOC (mBOC, triangles). Saturation curves show that both antibodies (intracellular and extracellular) can specifically detect mBOC in cellular extracts.
Figure 20B:
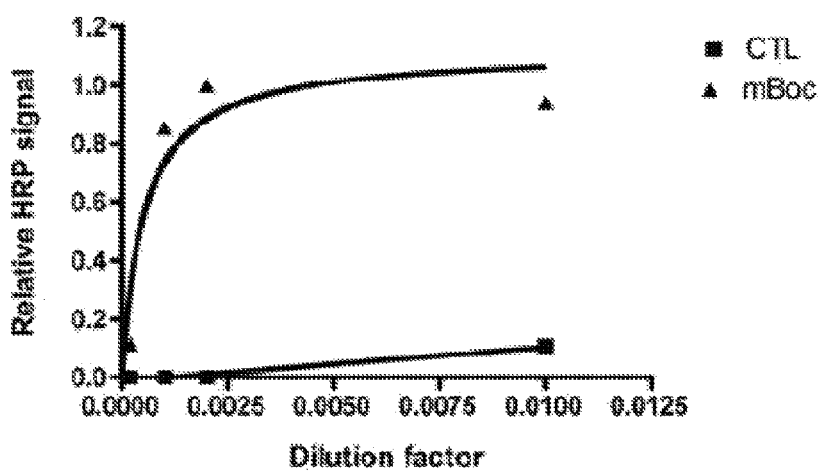
Figure 21A:
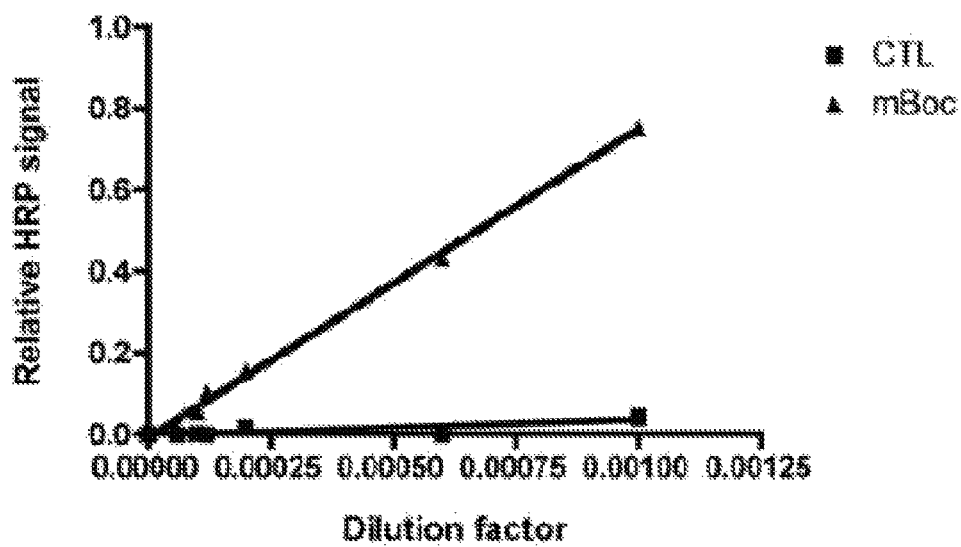
FIG. 21 shows a direct-ELISA using anti-BOC antibodies for detection. Antibodies recognize either the cytoplasmic tail (FIGS. 21A and C) or the extracellular portion (FIGS. 21B and D) of BOC were used. ELISA quantifications were performed on cellular extracts (FIGS. 21A and B) or tissue-culture media harvested (FIGS. 21C and D) from COS7 cells transfected with a control plasmid (CTL, squares) or mouse BOC (mBOC, triangles). The linear range of detection is represented in each graph and shows that the anti-BOC antibody binding to the extracellular portion can detect mBOC both in cellular extracts and tissue-culture media, whereas the anti-BOC antibody recognizing the cytoplasmic region can only detect mBOC in cellular extracts.
Figure 21B:
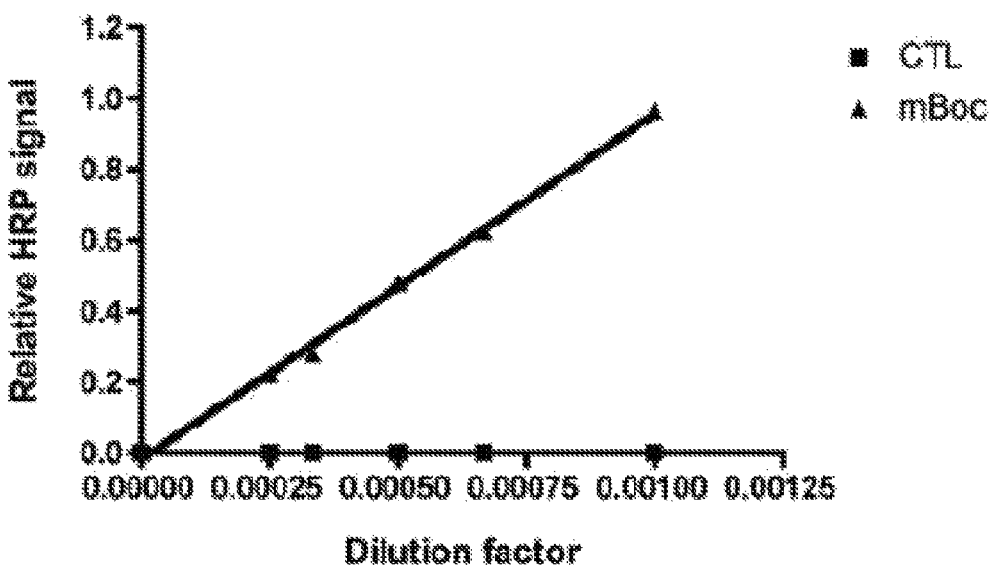
Figure 22A:
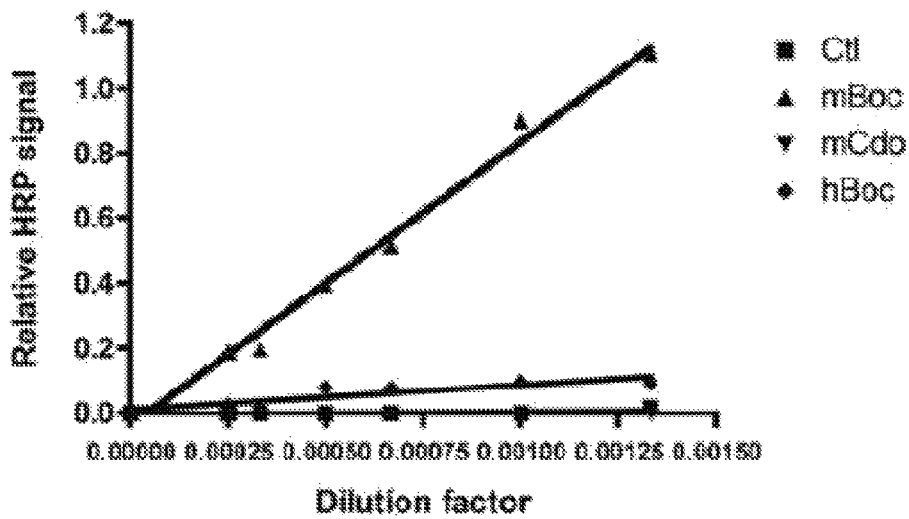
FIG. 22 shows a direct-ELISA performed with anti-BOC antibodies which recognize either the extracellular portion of BOC (FIGS. 22A and B) or its cytoplasmic tail (FIG. 22C). ELISA quantifications were performed on cellular extracts (FIGS. 22A and C) or tissue-culture media (FIG. 22B) harvested from COS7 cells transfected with a control plasmid (CTL, squares), mouse BOC (mBOC, triangles), mouse Cdo (mCdo, inverted triangles) or human BOC (hBOC, diamonds). Each graph represents the linear range of detection, showing that both anti-BOC antibodies are specific for mBOC.
Figure 22B:
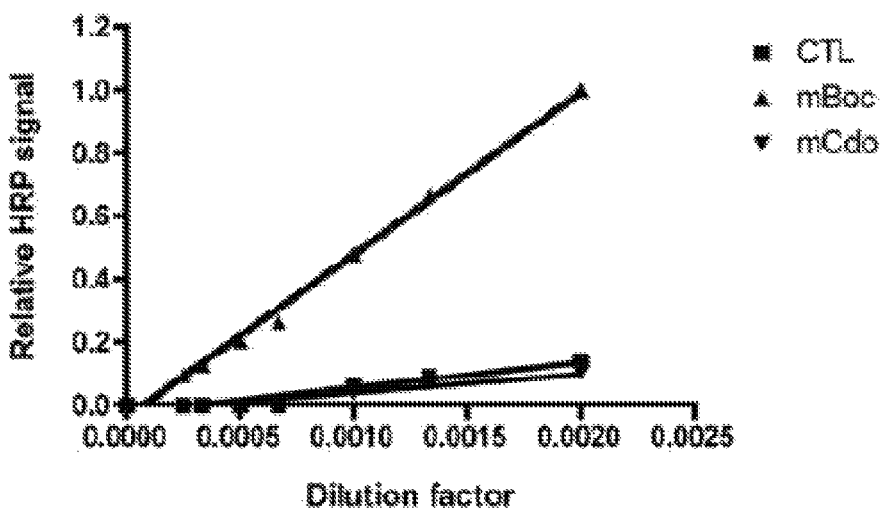
Figure 22C:
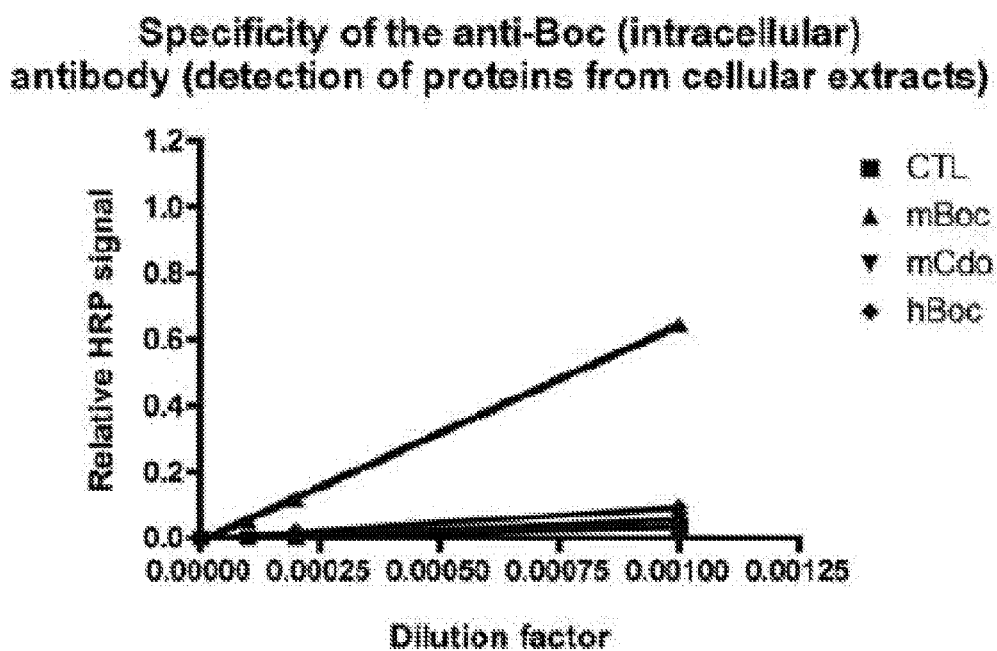

An enzyme-linked immunosorbant assay (ELISA) that allows the specific detection of mouse BOC was developed (FIGS. 20 to 22). Two different antibodies, one targeting the extracellular (R&D Systems, Cat. No. AF2385) and one targeting the intracellular domain of mouse BOC (mouse Boc polyclonal rabbit antiserum generated against a Boc cytoplasmic domain synthetic peptide, RRTSESPGLESSWDPPYH (SEQ ID NO: 15), Okada et al., Nature (2006) 444: 369-373), can detect mouse BOC with high sensitivity (FIGS. 20 and 21), with a detection threshold of about 10 to 100 pg, depending on the type of sample analyzed. Moreover, these assays are specific for mouse BOC, with minimal or no cross-reaction with the highly-related homologous family member Cdo (mCdo) or the highly-conserved ortholog human BOC (hBOC; FIGS. 22A to C). Additionally, the antibody directed against the extracellular portion of BOC can detect BOC in the tissue culture media, while the antibody targeting the intracellular portion of BOC cannot (FIG. 21). These results indicate that a significant portion of BOC comprising an extracellular domain is shed from the cell surface. Similar observations were made by Western blots in different cell types tested (COS, 293 and NIH 3T3 cells).

Figure 23A:
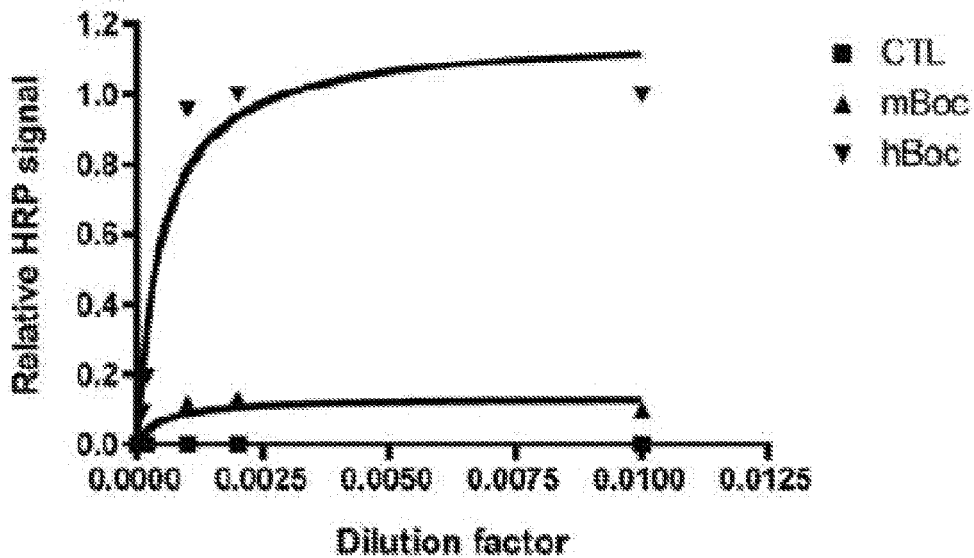
FIG. 23 shows direct-ELISA performed with an anti-human BOC as detection antibody. ELISA quantifications were performed on cellular extracts from COS7 cells transfected with a control plasmid (CTL, squares), mouse BOC (mBOC, triangles) or human BOC (hBOC, inverted triangles). Saturation curve (FIG. 23A) and linear range of detection (FIG. 23B) both show that the anti-human BOC antibody is specific for hBOC.
Figure 23B:
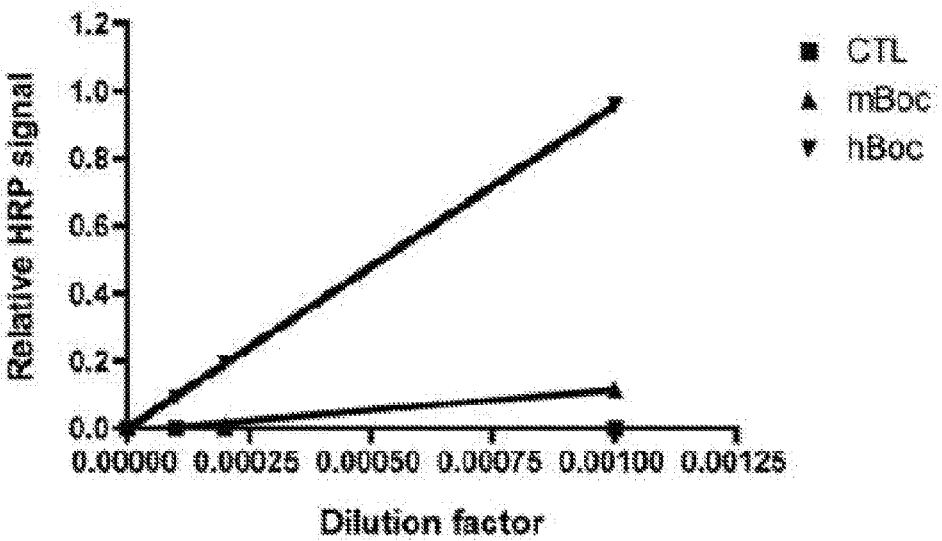

Similarly to the assay described above, an ELISA was developed using an antibody (R&D Systems, Cat No. AF2036) that detects the extracellular domain of human BOC (hBOC; FIG. 23). This antibody had minimal cross-reaction with the highly-conserved ortholog mouse BOC (mBOC; FIG. 23). The detection threshold for this assay was between about 10 to 100 pg.

Example 7

Detection of BOC Protein and RNA Present in the Cerebrospinal Fluid and Blood

BOC protein could be present in the CSF as a shed extracellular domain of BOC or expressed by tumor cells detached from the tumor and found in the CSF. After CSF collection, the cells are separated from the liquid phase by centrifugation. Proteins and RNAs are isolated from the CSF cells. The presence of BOC protein in the CSF liquid phase (e.g., due to shed extracellular domain) and CSF cells (due to detached tumor cells) are determined by known techniques such as ELISA (as described above as well as any ELISA-related technologies), immunoprecipitation followed by Western blotting or quantitative mass spectrometry. The presence of BOC mRNA in CSF cells is determined by known techniques such as quantitative reverse-transcriptase PCR (qPCR).

In parallel, as brain tumor proteins are also sometimes found in the blood or expressed by tumor cells that have escaped from the tumor and entered the circulation (Hormigo, A. et al., Clin Cancer Res 12(19): 5698 (2006); Tanwar, M. K. et al., Cancer Res 62(15): 4364 (2002)), the presence of BOC protein in the blood at this late tumorigenic stage is determined. This is done by known techniques such as ELISA (as described above), Sandwich immunoprecipitation followed by Western blotting or quantitative mass spectrometry performed on blood serum. In addition, ELISA and qPCR are performed on cells isolated from the blood.

The measurement is used as a diagnostic tool for the tailor-made therapeutic approach applicable to each patient (e.g., patient stratification). For example, a higher level of BOC protein or RNA in the tested sample than in a reference sample may be indicative of a predisposition to medulloblastoma. A higher level of BOC protein or RNA may also be indicative of a need for a treatment targeting BOC activity, or a more aggressive treatment.

The invention claimed is:

1. A method for diagnosing a cancer or a predisposition to cancer in a first subject comprising:
   (a) determining a level and/or activity of BOC in a sample from said first subject;
   (b) comparing said level and/or activity to a corresponding reference level and/or activity; and
   (c) diagnosing said cancer or predisposition to cancer based on said comparison,
wherein said cancer is a brain tumor, an ovary tumor, a breast tumor, a glioblastoma, a skin tumor, a meningioma, an astrocytoma, a liver tumor, a prostate carcinoma, a bladder tumor, a lung tumor, a lymph node lymphoma, a vascular endothelium hemangioma, a kidney carcinoma or a thyroid follicular adenoma; and
wherein a higher level and/or activity of said BOC in said sample from said first subject as compared to said reference level and/or activity is indicative that said first subject has cancer or a predisposition to cancer.

2. The method of claim 1, wherein said reference level and/or activity corresponds to a level and/or activity determined in a sample from a control subject known to not being predisposed to cancer and not having cancer.

3. The method of claim 1, wherein said brain tumor is a neuroectodermal tumor.

4. The method of claim 1, wherein said neuroectodermal tumor is a medulloblastoma.

5. The method of claim 1, wherein said sample is cerebrospinal fluid.

6. The method of claim 1, wherein the level of BOC is determined by determining the level of a nucleic acid encoding the polypeptide comprising the sequence of SEQ ID NO: 2.

7. The method of claim 6, wherein said nucleic acid comprises the coding sequence of the nucleotide sequence of SEQ ID NO: 1.

8. The method of claim 1, wherein the level of BOC is determined by determining the level of a polypeptide comprising the sequence of SEQ ID NO: 2, or of a fragment thereof.

9. The method of claim 8, wherein said fragment is an extracellular fragment.

10. The method of claim 1, wherein said cancer is a liver tumor.

11. The method of claim 1, wherein said cancer is an ovary tumor.

12. The method of claim 1, wherein said cancer is a breast tumor.

13. The method of claim 1, wherein said cancer is a glioblastoma.

14. The method of claim 1, wherein said cancer is a skin tumor.

15. The method of claim 1, wherein said cancer is a meningioma.

16. The method of claim 1, wherein said cancer is an astrocytoma.

17. The method of claim 1, wherein said cancer is a prostate carcinoma.

18. The method of claim 1, wherein said cancer is a bladder tumor.

19. The method of claim 1, wherein said cancer is a lung tumor.

20. The method of claim 1, wherein said cancer is a lymph node lymphoma.

21. The method of claim 1, wherein said cancer is a vascular endothelium hemangioma.

22. The method of claim 1, wherein said cancer is a kidney carcinoma.

23. The method of claim 1, wherein said cancer is a thyroid follicular adenoma.

* * * * *